(12) United States Patent
Hillebrand et al.

(10) Patent No.: US 9,914,728 B2
(45) Date of Patent: Mar. 13, 2018

(54) HETEROARYL PIPERIDINE AND HETEROARYL PIPERAZINE DERIVATIVES AS FUNGICIDES

(71) Applicant: BAYER INTELLECTUAL PROPERTY GMBH, Monheim am Rhein (DE)

(72) Inventors: Stefan Hillebrand, Neuss (DE); Pierre Cristau, Lyons (FR); Sebastian Hoffmann, Neuss (DE); Joachim Kluth, Langenfeld (DE); Pierre Wasnaire, Duesseldorf (DE); Tomoki Tsuchiya, Lyons (FR); Juergen Benting, Leichlingen (DE); Ulrike Wachendorff-Neumann, Neuwied (DE); Thomas Seitz, Langenfeld (DE)

(73) Assignee: BAYER INTELLECTUAL PROPERTY GMBH, Monheim (DE)

(*) Notice: Subject to any disclaimer, the term of this patent is extended or adjusted under 35 U.S.C. 154(b) by 0 days.

(21) Appl. No.: 15/339,595

(22) Filed: Oct. 31, 2016

(65) Prior Publication Data

US 2017/0044154 A1 Feb. 16, 2017

Related U.S. Application Data

(63) Continuation of application No. 14/598,895, filed on Jan. 16, 2015, now Pat. No. 9,512,117, which is a continuation of application No. 13/879,876, filed as application No. PCT/EP2011/068592 on Oct. 25, 2011, now abandoned.

(60) Provisional application No. 61/407,200, filed on Oct. 27, 2010.

(30) Foreign Application Priority Data

Oct. 27, 2010 (EP) ..................................... 10189067

(51) Int. Cl.
  C07D 417/04 (2006.01)
  A01N 43/80 (2006.01)
  C07D 417/14 (2006.01)

(52) U.S. Cl.
  CPC ........... *C07D 417/14* (2013.01); *A01N 43/80* (2013.01)

(58) Field of Classification Search
  None
  See application file for complete search history.

(56) References Cited

U.S. PATENT DOCUMENTS

| 4,245,432 A | 6/1981 | Dannelly |
| 4,272,417 A | 6/1981 | Barke |
| 4,808,430 A | 2/1989 | Kouno |
| 5,876,739 A | 3/1999 | Turnblad |
| 8,524,743 B2 | 9/2013 | Cristau et al. |
| 8,759,527 B2 | 6/2014 | Tsuchiya et al. |
| 9,006,266 B2 | 4/2015 | Tsuchiya et al. |
| 9,090,604 B2 | 7/2015 | Pasteris et al. |
| 9,150,565 B2 | 10/2015 | Tsuchiya et al. |
| 9,512,117 B2 * | 12/2016 | Hillebrand ............. A01N 43/80 |
| 2003/0176428 A1 | 9/2003 | Schneidersmann |
| 2010/0137245 A1 | 6/2010 | Cristau et al. |
| 2010/0190828 A1 | 7/2010 | Cristau et al. |
| 2011/0046178 A1 | 2/2011 | Cristau et al. |
| 2011/0105429 A1 | 5/2011 | Cristau et al. |
| 2011/0124501 A1 | 5/2011 | Cristau et al. |
| 2011/0224257 A1 | 9/2011 | Cristau et al. |
| 2011/0301197 A1 | 12/2011 | Cristau et al. |
| 2011/0306620 A1 | 12/2011 | Cristau et al. |
| 2011/0312999 A1 | 12/2011 | Cristau et al. |
| 2013/0296272 A1 | 11/2013 | Tsuchiya et al. |

FOREIGN PATENT DOCUMENTS

| EP | 2563786 A1 | 3/2013 |
| EP | 2571873 A1 | 3/2013 |
| JP | 60156601 | 8/1985 |
| WO | 1989010396 | 11/1989 |
| WO | 1996033270 | 10/1996 |
| WO | 2002028186 | 4/2002 |
| WO | 2002080675 | 5/2004 |
| WO | 2005040159 | 5/2005 |
| WO | 2006084015 | 10/2006 |

(Continued)

OTHER PUBLICATIONS

Form 237, PCT/EP2011/068592, p. 1-16 (2013).
Bayer CropSci. "Heteroarylpiperidine . . . "CA156:311075 (2012).
Cristau et al., "Bis(difluoromethyl)pyrazoles . . . "CA155:123398 (2011).
Bach Thorsten, "Regioselective Cross-Coupling Reactions as an Entry into Biologically Relevant Bithiazoles: First Total Synthesis of Cystothiazole E**", Angew. Chem. Int. Ed. vol. 40, No. 17, 2001, 3184-3185.

(Continued)

*Primary Examiner* — Zinna Northington Davis
(74) *Attorney, Agent, or Firm* — McBee Moore Woodward & Vanik IP, LLC

(57) ABSTRACT

Heteroarylpiperidine and -piperazine derivatives of the formula (I)

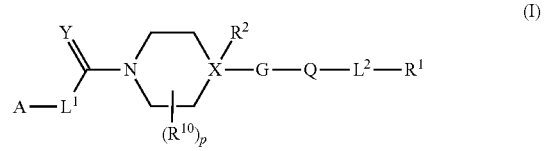

in which the symbols A, X, Y, $L^1$, $L^2$, G, Q, p, $R^1$, $R^2$ and $R^{10}$ are each as defined in the description, and salts, metal complexes and N-oxides of the compounds of the formula (I), and the use thereof for controlling phytopathogenic harmful fungi and processes for preparing compounds of the formula (I).

11 Claims, No Drawings

(56) References Cited

FOREIGN PATENT DOCUMENTS

| WO | 2006106423 | 10/2006 |
| WO | 2006117521 | 11/2006 |
| WO | 07/014290 A1 | 2/2007 |
| WO | 2007024 782 | 3/2007 |
| WO | 2007027777 | 7/2007 |
| WO | 2007103187 | 9/2007 |
| WO | 2007147336 | 12/2007 |
| WO | 2008/013622 A2 | 1/2008 |
| WO | 2008/013925 A2 | 1/2008 |
| WO | 2008062276 | 5/2008 |
| WO | 08/091580 A2 | 7/2008 |
| WO | 08/091594 A2 | 7/2008 |
| WO | 2008104077 | 9/2008 |
| WO | 2008147831 | 12/2008 |
| WO | 2008157500 | 12/2008 |
| WO | 2009/014290 A1 | 1/2009 |
| WO | 2009/055514 A2 | 4/2009 |
| WO | WO 2009/055514 A2 * | 4/2009 |
| WO | 2009/094407 A2 | 7/2009 |
| WO | 2009/094445 A2 | 7/2009 |
| WO | 09/132785 A1 | 11/2009 |
| WO | 10/037479 A1 | 4/2010 |
| WO | 2010/065579 A2 | 6/2010 |
| WO | 2010/066353 A1 | 6/2010 |
| WO | 2010/149275 A1 | 12/2010 |
| WO | 2011/018401 A1 | 2/2011 |
| WO | 2011/018415 A2 | 2/2011 |
| WO | 2011/051243 A1 | 5/2011 |
| WO | 2011/051244 A1 | 5/2011 |
| WO | 2011/076510 A1 | 6/2011 |
| WO | 2011/076699 A1 | 6/2011 |

OTHER PUBLICATIONS

Ballard Peter, "Neutral 5-Substituted 4-Anilinoquinazolines as Potent, Orally Active Inhibitors of erbB2 Receptor Tyrosine Kinase", Bioorganic & Medicinal Chemistry Letters vol. 17, 2007, 6326-6329.

Barany George, "A general Strategy for Elaboration of the Dithiocarbonyl Functionality,—(C=O)SS-: Application to the Synthesis of Bis(chlorocarbonyl)disulfane and Related Derivatives of Thiocarbonic Acids", J. Ora. Chem. vol. 48, 1983, 4750-4761.

Chen Wei, "The Design and Sythesis of Bis(thiourea) Ligands and Their Application in Pd- Catalyzed Heck and Suzuki Reactions Under Aerobic Conditions", Eur. J. Org. Chem., 2006, 1177-1184.

Clausen Thomsen, "Thiation With 2,4-Bis(4-Methoxyphenyl)-1,3,2,4-Dithiadiphophetane 2,4-Disulfide: N-Methylthiopyrrolidone", Organic Syntheses, Coll. vol. 7, p. 372, 1990; vol. 62, p. 158 (1984), 1-4.

Coleridge Brian, "General and User-Friendly Protocol for the Synthesis of Functionalized Aryl- and Heteroaryl-cyclopropanes by Negishi Cross-Coupling Reactions", Tetrahedron Letters vol. 50, 2009, 4475-4477.

Collins, David J., "Organophosphorus Compounds XVIII: Synthesis of 2-Pheyl-2,3-dihydro- 1H-1,2-benzazaphosphole 2-Sulfide by Pyrolysis of (2-Aminobenzyl)phenyldithiophosphinic Acid", Aust. J. Chem vol. 36, 1983, 2095-2110.

Dondoni Allesandro, "A New Convenient Preparation of 2-, 4-, and 5- Thiazolecarboxaldehydes and Their Conversion into the Corresponding Carbonitrile N- Oxides: Sythesis of 3-Thiazolylisoxazoles and 3-Thiazolylisoxazolines", Sythesis Papers, Nov. 1987, 998-1001.

"European Search Report for Eurpoean Patent Application No. 10189067.1, dated Apr. 8, 2011", 1-7.

Grzyb J., "Achieving Functional Group Diversity in Parallel Synthesis: Solution-phase Synthesis of a Library of Ureas, Carbamates, Thiocarbamates, and Amides Using Carbamovlimidazolium Salts", Tetrahedron Letters vol. 49, 2008, 5279-5282.

Grzyb Justyna, "Carbamoylimidazolium and Thiocarbamoylimidazolium Salts: Novel Reagents for the Synthesis of Ureas, Thioureas, Carbamates, Thiocarbamates and Amides", Tetrahedron vol. 61, 2005, 7153-7175.

Haberman Jannine, "Dehydrative Sialylation with C2-Hemiketal Sialyl Donors", Organic Letters vol. 5, No. 14, 2003, 2539-2541.

"International Search Report for International Application No. PCT/EP2011/068592, dated Oct. 25, 2011", 1-16.

Julia Marc, "Syntheses A L'aide de Sulfones V(+)—Methode de Synthese Generale De Double Liaisons", Tetrahedron Letters No. 49, 1973, 4833-4836.

Kanemasa Shuji, "Sythesis of Hydroximoyl Chlorides from Aldoximes and Benzyltrimethylammonium Tetrachloroiodate (BTMA ICI4)", Tetrahedron Vole. 56, 2000, 1057-1064.

Li Chun Sing, "Thiazole Analog as Stearoyl-CoA Desaturase 1 Inhibitor", Bioorganic & Medicial Chemistry Letters, vol. 19, 2009, 5214-5217.

Maryanoff Bruce, "The Wittig Olefination Reaction and Modifications Involving Phosphoryl- Stabilized Carbanions. Stereo Chemistry, Mechanism, and Selected Synthetic Aspects", Chem. Rev. vol. 89, 1989, 863-927.

Vlontalbetti Christian, "Amide Bond Formation and Peptide Coupling", Tetrahedron vol. 61, 2005, 10827-10852.

Pastemak Alexander, "Potent Heteroarylpiperidine and Carboxyphenylpiperidine 1-alkyl- cyclopentane-carboxamide CCR2 Antagonists", Bioorganic & Medicinal Chemistry Letters, vol. 18, 2008, 994-998.

Peterson, Donald J., "A Carbonyl Olefination Reaction Using Silyl-Substituted Organometallic Compounds", J. Org. Chem. vol. 33, No. 2, Feb. 1968, 780-784.

Qiao Jennifer, "Highly Efficacious Factor Xa Inhibitors Containing alpha-Substituted Phenylcycloalkyl P4 Moieties", Bioorganic & Medicinal Chemistry Letters vol. 19, 2009, 462-468.

Roth Gerald, "Further Improvements of the Synthesis of Alkynes from Aldehydes", Synthesis papers No. 1, 2004, 0059-0062.

Rouden Jacques, "Studies Toward Labeling Cytisine with [11c]Phsogene: Rapid Sythesis of a delta-Lactam Involving a New Chemoselective Lithiation-Annulation Method", J. Org. Chem. vol. 69, 2004, 3787-3793.

Schweifer Anna, "Formal and Improved Synthesis of Enantiopure Chiral Methanol", Tetrahedron vol. 64, 2008, 7605-7610.

Shakespeare William, "SAR of Carbon-Linked, 2-Substituted Purines: Synthesis and Characterization of AP23451 as a Novel Bone-Targeted Inhibitor of Src Tyrosine Kinase with In Vivo Anti-Resorptive Activity", Checm Biol Druq Des vol. 71, 2008, 97-105.

"Website: gmoinfo.jrc.ec.europa.eu accessed Aug. 7, 2013", 1.

"Website: www.cera-gmc.org/?action=gm_crop_database accessed Aug. 7, 2013", 1.

Yeh Vince, "Practical Cu-Catalyzed Amination of Functionalized Heteroaryl Halides", Tetrahedron Letters vol. 47, 2006, 6011-6016.

Hillebrand et al. "Heteroarylpiperidine . . . " CA156:588353 (2012). Form 237, PCT/EP2011/068592 p. 1-16 (2013).

Pasteris et al. "Fungicidal azacyclic amides" CA148:185135 (2008).

International Search Report of PCT/EP2011/068592 dated Jan. 30, 2012.

* cited by examiner

HETEROARYL PIPERIDINE AND HETEROARYL PIPERAZINE DERIVATIVES AS FUNGICIDES

CROSS REFERENCE TO RELATED APPLICATIONS

This application is a continuation application of U.S. application Ser. No. 14/598,895, filed Jan. 16, 2015, which is a continuation application of U.S. application Ser. No. 13/879,876, filed Sep. 23, 2013, which is a § 371 National Stage Application of PCT/EP2011/068592, filed Oct. 25, 2011, which claims priority to European Application No. 10189067.1, filed Oct. 27, 2010 and U.S. Provisional Application 61/407,200, filed Oct. 27, 2010, the contents of which are incorporated herein by reference in their entireties.

BACKGROUND OF THE INVENTION

Field of the Invention

The invention relates to heteroarylpiperidine and -piperazine derivatives, to agrochemically active salts thereof, to use thereof and to methods and compositions for controlling phytopathogenic harmful fungi in and/or on plants or in and/or on seed of plants, to processes for producing such compositions and treated seed, and to use thereof for controlling phytopathogenic harmful fungi in agriculture, horticulture and forestry, in animal health, in the protection of materials and in the domestic and hygiene sector. The present invention further relates to a process for preparing heteroarylpiperidine and -piperazine derivatives.

Description of Related Art

It is already known that particular heterocyclically substituted thiazoles can be used as fungicidal crop protection agents (see patent applications with publication numbers: WO 07/014290, WO 08/013925, WO 08/013622, WO 08/091594, WO 08/091580, WO 09/055514, WO 09/094407, WO 09/094445, WO 09/132785, WO 10/037479, WO10/065579, WO2010/066353, WO2010/149275, WO2011/051243, WO2011/051244, WO 2011/076510, WO 2011/018415, WO 2011/018401, WO 2011/076699; see also patent applications with application numbers: DE102010000662.9, PCT/EP2011/056594, PCT/EP2011/057912, PCT/EP2011/058330, PCT/EP2011/063783, PCT/EP2011/064527). However, specifically at relatively low application rates, the fungicidal efficacy of these compounds is not always adequate.

Since the ecological and economical demands made on modern crop protection agents are increasing constantly, for example with respect to activity spectrum, toxicity, selectivity, application rate, formation of residues and favourable manufacture, and there can furthermore be problems, for example, with resistances, there is a constant need to develop novel crop protection agents, in particular fungicides, which, at least in some areas, have advantages over the known ones.

It has now been found that, surprisingly, the present heteroarylpiperidine and -piperazine derivatives achieve at least some aspects of the objects mentioned and are suitable for use as crop protection agents, especially as fungicides.

SUMMARY

The invention provides compounds of the formula (I)

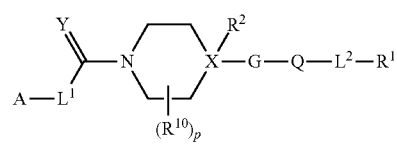

in which the radicals are each defined as follows:
A is phenyl which may contain up to five substituents, where the substituents are each independently selected from $Z^{A-1}$,
or
A is an optionally benzofused, unsubstituted or substituted 5- or 6-membered heteroaryl which may contain up to four substituents, where the substituents on carbon are each independently selected from $Z^{A-2}$ and the substituents on nitrogen are each independently selected from $Z^{A-3}$, $Z^{A-1}$ are the same or different and are each independently hydrogen, halogen, hydroxyl, thioxy, nitro, cyano, —C(=O)H, —C(=O)OH, alkyl, alkenyl, alkynyl, haloalkyl, haloalkenyl, haloalkynyl, cycloalkyl, cycloalkenyl, halocycloalkyl, halocycloalkenyl, hydroxyalkyl, cyanoalkyl, formylalkyl, alkoxyalkyl, haloalkoxyalkyl, cycloalkoxyalkyl, alkynyloxyalkyl, alkylthioalkyl, alkylsulphinylalkyl, alkyl aminoalkyl, haloalkylaminoalkyl, cycloalkylaminoalkyl, dialkylaminoalkyl, alkylcarbonylalkyl, alkylsulphonylalkyl, alkylcycloalkyl, alkylcycloalkenyl, alkoxy, alkylcycloalkylalkyl, halocycloalkoxy, alkylthio, haloalkylthio, cycloalkylthio, alkynylthio, alkenyloxy, alkynyloxy, haloalkoxy, haloalkenyloxy, haloalkynyloxy, cycloalkoxy, alkoxyalkoxy, cycloalkylalkoxy, alkylcarbonyloxy, haloalkylcarbonyloxy, cycloalkylcarbonyloxy, cycloalkylamino, alkylcarbonylamino, cycloalkylcarbonylamino, alkoxycarbonylamino, alkylsulphonylamino, haloalkylsulphonylamino, phenylsulphonylamino, cycloalkylalkyl, halocycloalkylalkyl, cycloalkylcycloalkyl, alkoxyalkoxyalkyl, alkylaminocarbonyloxy, alkylcarbonylalkoxy, cycloalkylaminocarbonyl, cycloalkylalkoxycarbonyl, alkylsulphinyl, haloalkylsulphinyl, alkylsulphonyl, haloalkylsulphonyl, cycloalkylsulphonyl, alkylcarbonyl, haloalkylcarbonyl, cycloalkylcarbonyl, alkoxycarbonyl, cycloalkoxycarbonyl, trialkylsilyl, —SF$_5$, phenyl, —C(=O)NR$^3$R$^4$ or —NR$^3$R$^4$, $Z^{A-2}$ and R$^{G1}$ are the same or different and are each independently hydrogen, halogen, hydroxyl, thioxy, nitro, cyano, —C(=O)H, —C(=O)OH, alkyl, alkenyl, alkynyl, haloalkyl, haloalkenyl, haloalkynyl, cycloalkyl, halocycloalkyl, hydroxyalkyl, formylalkyl, alkoxyalkyl, alkylcarbonylalkyl, alkylcycloalkyl, alkoxy, alkylcycloalkylalkyl, alkylthio, haloalkylthio, alkynylthio, alkenyloxy, alkynyloxy, haloalkoxy, alkoxyalkoxy, alkylcarbonyloxy, haloalkylcarbonyloxy, cycloalkylcarbonylamino, alkylsulphonylamino, haloalkylsulphonylamino, phenylsulphonylamino, cycloalkylalkyl, halocycloalkylalkyl, cycloalkylcycloalkyl, alkoxycarbonyloxy, alkylcarbonylthio, alkylsulphinyl, haloalkylsulphinyl, alkylsulphonyl, haloalkylsulphonyl, alkylcarbonyl, haloalkylcarbonyl, alkoxycarbonyl, alkylaminocarbonyloxy, —C(=O)NR³R⁴ or —NR³R⁴, $Z^{4-3}$, $R^{G2}$ and $Z^2$ are the same or different and are each independently hydrogen, —C(=O)H, —C(=O)NR³R⁴, alkyl, alkenyl, alkynyl, haloalkyl, haloalkenyl, haloalkynyl, cycloalkyl, halocycloalkyl, alkylcycloalkyl, cycloalkylalkyl, alkoxyalkyl, alkylsulphonyl, haloalkylsulphonyl, cycloalkylsulphonyl, phenylsulphonyl, alkylcarbonyl, haloalkylcarbonyl, alkoxycarbonyl, haloalkoxycarbonyl, cycloalkoxycarbonyl, phenyl or benzyl, R³ and R⁴ are the same or different and are each independently hydrogen, alkyl, alkenyl, alkynyl, haloalkyl, cycloalkyl, benzyl or phenyl, $L^1$ is $NR^{L12}$ or $C(R^{L11})_2$, $R^{L11}$ is the same or different and is independently hydrogen, halogen, hydroxyl, cyano, —C(=O)H, —C(=O)OH, alkyl, alkenyl, alkynyl, haloalkyl, haloalkenyl, haloalkynyl, alkoxyalkyl, alkylthioalkyl, alkylaminoalkyl, dialkylaminoalkyl, alkoxy, alkylthio, haloalkylthio, haloalkoxy, alkylcarbonyloxy, alkylcarbonylamino, alkylcarbonylthio, alkylsulphonyl, haloalkylsulphonyl, alkylcarbonyl, haloalkylcarbonyl, alkoxycarbonyl, trialkylsilyloxy, —NR³R⁴ or —C(=O)NR³R⁴, or the two $R^{L11}$ radicals, together with the carbon atom to which they are bonded, form a cyclopropyl ring, or the two $R^{L11}$ radicals are =CH₂, =COR³, =NOR³ or =CHN(R⁷)₂, $R^{L12}$ is hydrogen, —C(=O)H, alkyl, alkenyl, alkynyl, haloalkyl, haloalkenyl, haloalkynyl, cycloalkyl, halocycloalkyl, alkylcycloalkyl, cycloalkylalkyl, cycloalkylaminocarbonyl, haloalkylaminocarbonyl, alkylsulphonyl, haloalkylsulphonyl, cycloalkylsulphonyl, alkylcarbonyl, haloalkylcarbonyl, alkoxycarbonyl, haloalkoxycarbonyl, cycloalkoxycarbonyl, alkylaminocarbonyl, dialkylaminocarbonyl, phenyl or benzyl, R⁷ is alkyl, alkenyl, alkynyl, haloalkyl, cycloalkyl, benzyl or phenyl, Y is sulphur or oxygen, X is carbon or nitrogen, R² is hydrogen, alkyl, alkenyl, haloalkyl, alkoxy, halogen, cyano or hydroxyl, R¹⁰ is oxo, alkyl, alkenyl, haloalkyl, alkoxy, halogen, cyano or hydroxyl, p is 0, 1 or 2, G is 5-membered heteroaryl which is substituted by Q and may otherwise be unsubstituted or substituted, where the substituents on carbon are each independently selected from $R^{G1}$ and the substituents on nitrogen are each independently selected from $R^{G2}$, Q is saturated or partly or fully unsaturated 5-membered heterocyclyl which is substituted by $L^2-R^1$ and may otherwise be unsubstituted or substituted, where the substituents are each independently selected from R⁵, R⁵ is the same or different and is independently:

bonded to carbon of the 5-membered heterocyclyl of Q: hydrogen, oxo, halogen, cyano, hydroxyl, nitro, —CHO, —C(=O)OH, —C(=O)NH₂, —C(=O)NR³R⁴, —NR³R⁴, alkyl, alkenyl, alkynyl, haloalkyl, haloalkenyl, haloalkynyl, cycloalkyl, halocycloalkyl, alkylcycloalkyl, cycloalkylalkyl, cycloalkylcycloalkyl, halocycloalkylalkyl, alkylcycloalkylalkyl, cycloalkenyl, halocycloalkenyl, alkoxyalkyl, haloalkoxyalkyl, cycloalkoxyalkyl, alkoxyalkoxyalkyl, alkylthioalkyl, formylalkyl, alkylcarbonylalkyl, alkylsulphinylalkyl, alkylsulphonylalkyl, alkylaminoalkyl, dialkylaminoalkyl, haloalkylaminoalkyl, cycloalkylaminoalkyl, alkylcarbonyl, haloalkylcarbonyl, cycloalkylcarbonyl, alkoxycarbonyl, cycloalkoxycarbonyl, cycloalkylalkoxycarbonyl, cycloalkylaminocarbonyl, hydroxyalkyl, alkoxy, haloalkoxy, cycloalkoxy, halocycloalkoxy, cycloalkylalkoxy, alkenyloxy, haloalkenyloxy, alkynyloxy, haloalkynyloxy, alkoxyalkoxy, alkylcarbonyloxy, haloalkylcarbonyloxy, cycloalkylcarbonyloxy, alkylcarbonylalkoxy, alkylthio, haloalkylthio, cycloalkylthio, alkylsulphinyl, haloalkylsulphinyl, alkylsulphonyl, haloalkylsulphonyl, cycloalkylsulphonyl, trialkylsilyl, alkylsulphonylamino, haloalkylsulphonylamino, bonded to nitrogen of the 5-membered heterocyclyl of Q: hydrogen, alkyl, alkenyl, alkynyl, haloalkyl, haloalkenyl, haloalkynyl, cycloalkyl, halocycloalkyl, alkylcycloalkyl, cycloalkylalkyl, phenyl, benzyl, alkylsulphonyl, —C(=O)H, alkoxycarbonyl or alkylcarbonyl, $L^2$ is a direct bond, O, C(=O), $S(O)_m$, $CHR^{20}$ or $NR^{21}$, m is 0, 1 or 2, R²⁰ is hydrogen, alkyl or haloalkyl, R²¹ is hydrogen, alkyl, haloalkyl, cycloalkyl, alkylcarbonyl, haloalkylcarbonyl, alkoxycarbonyl or haloalkoxycarbonyl, R¹ is phenyl which is substituted once by a $Z^4$ substituent and may additionally optionally have further substitution, where these additional substituents are each independently selected from $Z^4$ and $Z^1$, or R¹ is naphthyl, dihydronaphthalenyl, tetrahydronaphthalenyl, hexahydronaphthalenyl, octahydronaphthalenyl or indenyl which is substituted once by a $Z^5$ substituent and may additionally optionally have further substitution, where these additional substituents are each independently selected from $Z^5$ and $Z^1$, or R¹ is an optionally benzofused, substituted 5- or 6-membered heteroaryl which is substituted once, either on a carbon by a $Z^6$ substituent or on the nitrogen by a $Z^7$ substituent, and may additionally optionally be substituted by further substituents, where the additional substituents on the carbon are each independently selected from $Z^1$ and $Z^6$, and the additional substituents on the nitrogen are each independently selected from $Z^2$ and $Z^7$, $Z^1$ is hydrogen, halogen, hydroxyl, nitro, cyano, alkyl, alkenyl, alkynyl, haloalkyl, haloalkenyl, haloalkynyl, cycloalkyl, halocycloalkyl, alkoxy, alkoxyalkyl, hydroxyalkyl, haloalkoxy, alkylcarbonyl, alkoxycarbonyl, alkylcycloalkyl, cycloalkoxyalkyl, cycloalkylamino, alkylthio, haloalkylthio, cycloalkylthio, cycloalkylalkyl, alkylcarbonyloxy, alkylcarbonylamino, haloalkylcarbonylamino, alkylcarbonylthio, alkylsulphinyl, haloalkylsulphinyl, alkylsulphonyloxy, haloalkylsulphonyloxy, alkylcycloalkylalkyl, —C(=O)NR³R⁴, —NR³R⁴, or -L³Z³, $L^3$ is a direct bond, —CH₂—, —C(=O)—, sulphur, oxygen, —C(=O)O—, —C(=O)NH—, —OC(=O)— or —NHC(=O)—, $Z^3$ is a phenyl radical, naphthalenyl radical or a 5- or 6-membered heteroaryl radical, each of which may contain 0, 1, 2 or 3 substituents, where the substituents are each independently selected from the following list:

substituents on carbon: halogen, cyano, nitro, hydroxyl, amino, —SH, alkyl, alkenyl, alkynyl, haloalkyl, haloalkenyl, haloalkynyl, cycloalkyl, halocycloalkyl, alkoxyalkyl, alkylcarbonyl, haloalkylcarbonyl, alkoxycarbonyl, alkoxy, haloalkoxy, cycloalkoxy, halocycloalkoxy, alkenyloxy, alkynyloxy, alkoxyalkoxy, alkylamino, dialkylamino, alkylthio, haloalkylthio, alkylsulphinyl, haloalkylsulphinyl, alkylsulphonyl, haloalkylsulphonyl, trisilylalkyl or phenyl, substituents on nitrogen: hydrogen, —C(=O)H, alkyl, alkenyl, alkynyl, haloalkyl, haloalkenyl, haloalkynyl, cycloalkyl, halocycloalkyl, alkylcycloalkyl, cycloalkylalkyl, alkoxyalkyl, alkylsulphonyl, haloalkylsulphonyl, cycloalkylsulphonyl, phenylsulphonyl, alkylcarbonyl, haloalkylcarbonyl, alkoxycarbonyl, haloalkoxycarbonyl, cycloalkoxycarbonyl, —C(=O)NR$^3$R$^4$, phenyl or benzyl, $Z^4$ is SH, C(=O)H, $C_7$-$C_8$-cycloalkyl, $C_7$-$C_8$-halocycloalkyl, cycloalkylcycloalkyl, halocycloalkylalkyl, cycloalkenyl, halocycloalkenyl, $C_4$-$C_6$-alkoxy-$C_1$-$C_4$-alkyl, $C_3$-alkoxy-$C_2$-$C_4$-alkyl, alkoxyalkoxyalkyl, alkylthioalkyl, alkylsulphinylalkyl, alkylsulphonylalkyl, alkylaminoalkyl, dialkylaminoalkyl, haloalkylaminoalkyl, cycloalkylaminoalkyl, $C_4$-$C_6$-alkylcarbonyl, haloalkylcarbonyl, cycloalkylcarbonyl, cycloalkoxycarbonyl, cycloalkylalkoxycarbonyl, cycloalkylaminocarbonyl, haloalkoxyalkyl, $C_5$-$C_6$-hydroxyalkyl, $C_5$-$C_6$-alkoxy, $C_5$-$C_6$-haloalkoxy, cycloalkoxy, halocycloalkoxy, cycloalkylalkoxy, alkenyloxy, haloalkenyloxy, alkynyloxy, haloalkynyloxy, alkoxyalkoxy, cyanoalkoxy, haloalkylcarbonyloxy, cycloalkylcarbonyloxy, alkylcarbonylalkoxy, $C_5$-$C_6$-alkylthio, $C_5$-$C_6$-haloalkylthio, $C_5$-$C_6$-alkylsulphinyl, $C_5$-$C_6$-haloalkylsulphinyl, $C_5$-$C_6$-alkylsulphonyl, $C_5$-$C_6$-haloalkylsulphonyl, cycloalkylsulphonyl, tri($C_3$-$C_4$-alkyl)silyl, alkylsulphonylamino or haloalkylsulphonylamino, $Z^5$ is tri($C_2$-$C_4$-alkyl)silyl, benzyl, phenyl, SH, $C_5$-$C_6$-alkoxy, $C_5$-$C_6$-haloalkoxy, $C_2$-$C_6$-alkenyloxy, $C_2$-$C_6$-alkynyloxy, $C_5$-$C_6$-alkylthio or $C_5$-$C_6$-haloalkylthio, $Z^6$ is SH, cycloalkylcycloalkyl or tri($C_3$-$C_4$-alkyl)silyl, $Z^7$ is alkenyl, alkynyl, haloalkyl, haloalkenyl, haloalkynyl, cycloalkyl, halocycloalkyl, alkylcycloalkyl, cycloalkylalkyl, cycloalkylcycloalkyl, alkylsulphonyl, C(=O)H, benzyl or phenyl, and salts, metal complexes and N-oxides of the compounds of the formula (I), with the proviso that the following compounds are excluded:

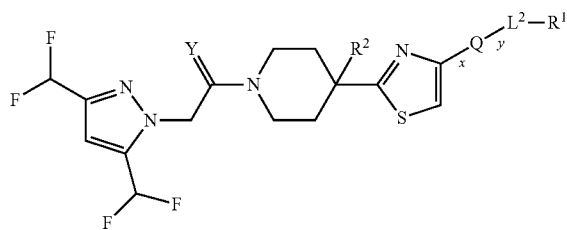

in which the symbols have the following meanings:
Y is oxygen or sulphur,
R$^2$ is hydrogen or halogen,
Q is

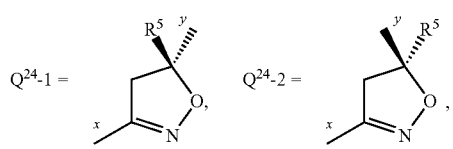

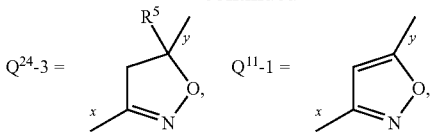

R$^5$ is hydrogen, cyano, $C_1$-$C_3$-alkyl or $C_1$-$C_3$-haloalkyl,
L$^2$ is a direct bond and
R$^1$ is as defined above, where, when R$^1$ is substituted phenyl, naphthyl, dihydronaphthalenyl, tetrahydronaphthalenyl, hexahydronaphthalenyl, octahydronaphthalenyl or indenyl or an optionally benzofused, 5- or 6-membered heteroaryl, not more than two substituents are present on the carbocycles or heterocycles mentioned.

DETAILED DESCRIPTION OF A PREFERRED EMBODIMENT

The invention further provides for the use of the compounds of the formula (I) as fungicides.

Inventive heteroarylpiperidine and -piperazine derivatives of the formula (I) and the salts, metal complexes and N-oxides thereof are very suitable for controlling phytopathogenic harmful fungi. The aforementioned inventive compounds exhibit, in particular, potent fungicidal activity and can be used in crop protection, in the domestic and hygiene sector and in the protection of materials.

The compounds of the formula (I) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and Z isomers, and the threo and erythro isomers, and also the optical isomers, any desired mixtures of these isomers, and the possible tautomeric forms are claimed.

The radical definitions of the inventive compounds of the formula (I) preferably, more preferably and most preferably have the following definitions:

A is preferably phenyl which may contain up to two substituents, where the substituents are each independently selected from the following list:
halogen, cyano, hydroxyl, —NR$^3$R$^4$, —C(=O)NR$^3$R$^4$, nitro, $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkenyloxy, $C_1$-$C_4$-alkynyloxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_1$-$C_4$-alkoxy-$C_1$-$C_6$-alkyl, hydroxy-$C_1$-$C_4$-alkyl, $C_1$-$C_6$-alkylcarbonyl, $C_1$-$C_6$-alkoxycarbonyl, $C_1$-$C_6$-alkylcarbonyloxy or —C(=O)H, or A is preferably a heteroaromatic radical selected from the following group: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrazin-2-yl, pyrazin-3-yl, pyrimidin-2-yl, pyrimidin-4-yl or pyrimidin-5-yl which may contain up to two substituents, where the substituents are each independently selected from the following list:

substituents on carbon:
halogen, cyano, hydroxyl, nitro, —NR³R⁴, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_1$-$C_4$-alkoxy-$C_1$-$C_4$-alkyl, hydroxy-$C_1$-$C_4$-alkyl, $C_1$-$C_6$-alkylcarbonyl, $C_1$-$C_6$-alkoxycarbonyl, $C_1$-$C_6$-alkylcarbonyloxy or phenyl, substituents on nitrogen:
$C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_{10}$-cycloalkyl-$C_1$-$C_6$-alkyl, $C_1$-$C_6$-haloalkylcarbonyl, phenyl, benzyl, $C_1$-$C_4$-alkylsulphonyl, $C_1$-$C_4$-haloalkylsulphonyl, phenylsulphonyl, —C(=O)H, or $C_1$-$C_6$-alkylcarbonyl, A is more preferably phenyl which may contain up to two substituents, where the substituents are each independently selected from the following list:
fluorine, bromine, iodine, chlorine, cyano, nitro, methyl, ethyl, n-propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, n-propoxy, methoxy, trifluoromethoxy, difluoromethoxy, 1-methylethylthio, methylthio, ethylthio, n-propylthio, difluoromethylthio or trifluoromethylthio, or A is more preferably a heteroaromatic radical selected from the following group: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrimidin-2-yl, pyrimidin-4-yl or pyrimidin-5-yl, which may contain up to two substituents, where the substituents are the same or different and are each independently selected from the following list:

substituents on carbon:
fluorine, chlorine, bromine, iodine, cyano, nitro, methyl, ethyl, n-propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, n-propoxy, methoxy, trifluoromethoxy, difluoromethoxy, 1-methylethylthio, methylthio, ethylthio, n-propylthio, difluoromethylthio, trifluoromethylthio or phenyl, substituents on nitrogen:
methyl, ethyl, n-propyl, 1-methylethyl, methylsulphonyl, trifluoromethylsulphonyl, methylcarbonyl, trifluoromethylcarbonyl, chloromethylcarbonyl, 2,2-trifluoroethyl, 2,2-difluoroethyl, 2,2-dichloro-2-fluoroethyl, 2-chloro-2-difluoroethyl or 2-chloro-2-fluoroethyl.

A is most preferably phenyl which may contain up to two substituents, where the substituents are each independently selected from the following list:
methyl, ethyl, iodine, chlorine, bromine, fluorine, methoxy, ethoxy, difluoromethyl or trifluoromethyl, or A is most preferably pyrazol-1-yl which may contain up to two substituents, where the substituents are each independently selected from the following list:
methyl, ethyl, chlorine, bromine, fluorine or trifluoromethyl, $R^3$ and $R^4$ are preferably the same or different and are each independently hydrogen, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, benzyl or phenyl, and more preferably hydrogen, methyl, ethyl, n-propyl, 1-methylethyl, n-butyl or 1,1-dimethylethyl, $L^1$ is preferably $C(R^{L11})_2$ (more preferably $CHR^{L11}$) or $NR^{L12}$ and most preferably $CH_2$, $R^{L11}$ is preferably hydrogen, methyl, ethyl or cyclopropyl, or the two $R^{L11}$ radicals, together with the carbon atom to which they are bonded, form a cyclopropyl ring, or the two $R^{L11}$ radicals are =CHN($R^7$)$_2$, $R^{L11}$ is more preferably hydrogen or methyl, $R^{L12}$ is preferably hydrogen, $C_1$-$C_4$-alkyl, $C_1$-$C_4$-haloalkyl, $C_3$-$C_8$-cycloalkyl, $C_1$-$C_4$-alkylsulphonyl, $C_1$-$C_4$-alkoxycarbonyl, and more preferably hydrogen or methyl, and most preferably hydrogen, $R^7$ is preferably the same or different and is independently $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, benzyl or phenyl, and more preferably hydrogen, methyl, ethyl, n-propyl, 1-methylethyl, n-butyl or 1,1-dimethylethyl, Y is preferably oxygen or sulphur and more preferably oxygen, X is carbon or nitrogen and preferably carbon, $R^2$ is preferably hydrogen, $C_1$-$C_4$-alkyl, $C_1$-$C_4$-alkenyl, $C_1$-$C_4$-haloalkyl, $C_1$-$C_4$-alkoxy, halogen, cyano or hydroxyl, and more preferably hydrogen, fluorine, chlorine, bromine or hydroxyl, and most preferably hydrogen or fluorine (and especially only hydrogen), $R^{10}$ is preferably oxo, $C_1$-$C_4$-alkyl, $C_1$-$C_4$-alkenyl, $C_1$-$C_4$-haloalkyl, $C_1$-$C_4$-alkoxy, halogen, cyano or hydroxyl, and more preferably fluorine, chlorine, bromine or hydroxyl, and most preferably fluorine, p is preferably 0 to 1, and more preferably 0, G is preferably

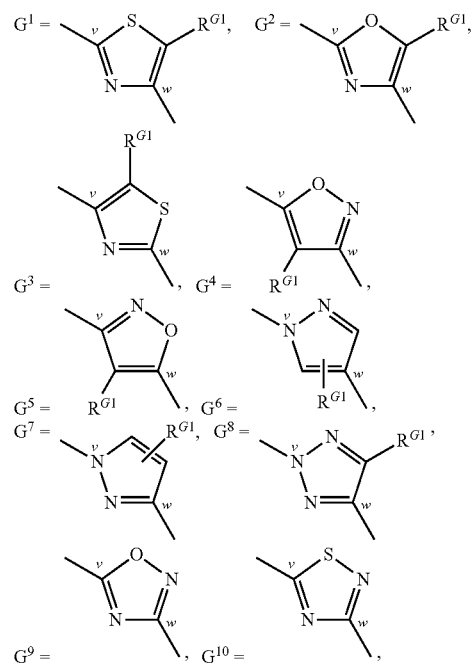

-continued

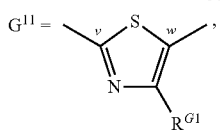

where the bond identified by "v" is bonded directly to X and where the bond identified by "w" is bonded directly to Q, G is more preferably $G^1$, $G^2$ or $G^3$, and most preferably $G^1$, $R^{G1}$ is preferably hydrogen or halogen and more preferably hydrogen, Q is preferably

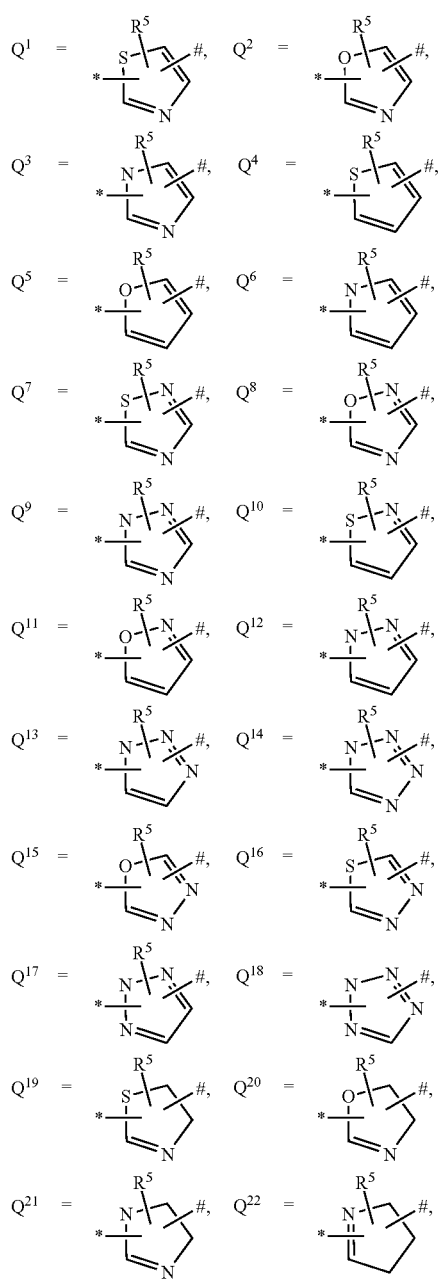

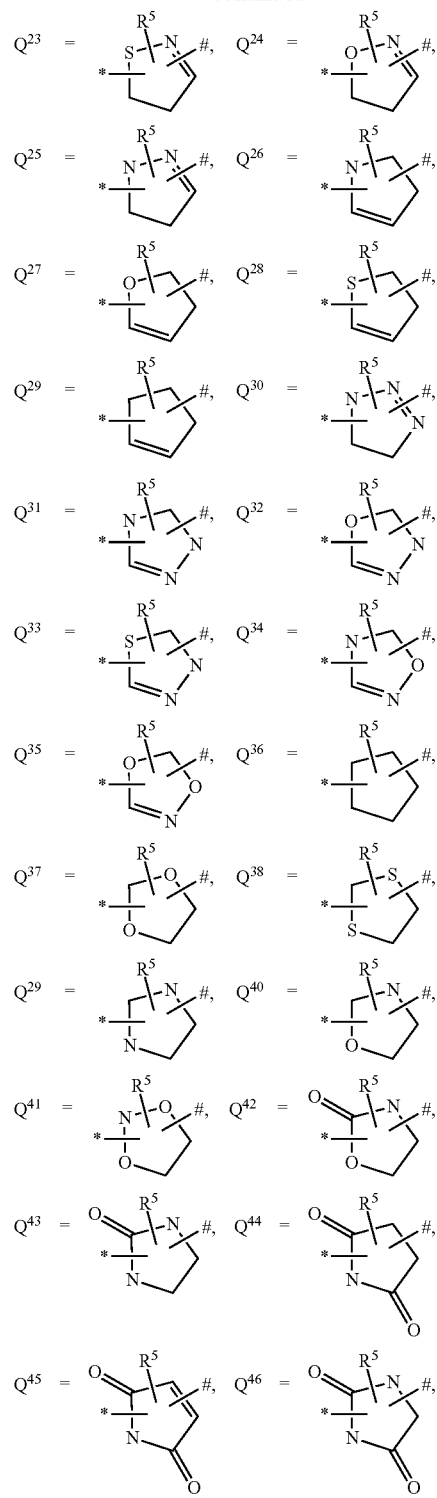

where the bond identified by "*" is bonded directly to G, and where the bond identified by "#" is bonded directly to $L^2$, or where the bond identified by "*" is bonded directly to $L^2$, and where the bond identified by "#" is bonded directly to G, Q is more preferably

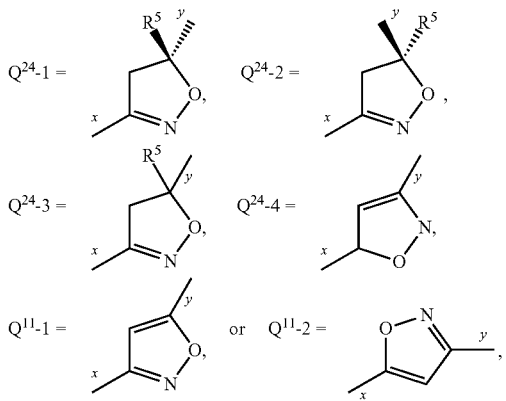

where the bond identified by "x" is bonded directly to G, and the bond identified by "y" is bonded directly to $L^2$, Q is most preferably $Q^{24}$-3, $R^5$ is preferably the same or different and is independently bonded to carbon of the 5-membered heterocyclyl of Q: hydrogen, cyano, —$NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_3$-$C_5$-halocycloalkyl, $C_1$-$C_4$-alkyl-$C_3$-$C_8$-cycloalkyl, $C_3$-$C_8$-cycloalkyl-$C_1$-$C_4$-alkyl, $C_1$-$C_4$-alkoxy-$C_1$-$C_4$-alkyl, $C_3$-$C_8$-cycloalkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkyl, $C_1$-$C_6$-alkoxy, $C_1$-$C_6$-haloalkoxy, $C_3$-$C_8$-cycloalkoxy, $C_3$-$C_8$-halocycloalkoxy, $C_3$-$C_8$-cycloalkyl-$C_1$-$C_4$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkoxy-$C_1$-$C_4$-alkoxy, $C_1$-$C_6$-alkylcarbonyloxy, $C_1$-$C_6$-haloalkylcarbonyloxy, $C_3$-$C_8$-cycloalkylcarbonyloxy, $C_1$-$C_6$-alkylcarbonyl-$C_1$-$C_6$-alkoxy, $C_1$-$C_6$-alkylthio, $C_1$-$C_6$-haloalkylthio, $C_3$-$C_8$-cycloalkylthio, bonded to nitrogen of the 5-membered heterocyclyl of Q: hydrogen, —C(=O)H, $C_1$-$C_3$-alkyl, $C_1$-$C_6$-alkylcarbonyl, $C_1$-$C_6$-alkoxycarbonyl or benzyl, $R^5$ is more preferably hydrogen, cyano, methyl, trifluoromethyl, difluoromethyl or methoxymethyl, or $R^5$ is most preferably hydrogen, $L^2$ is preferably a direct bond, —O—, —C(=O)—, —S(O)$_m$—, —CHR$^{20}$— or —NR$^{21}$—, and more preferably a direct bond, —C(=O)—, —CHR$^{20}$— or —NR$^{21}$— and most preferably $L^2$ is a direct bond, m is preferably 0 or 2, $R^{20}$ is preferably hydrogen, $C_1$-$C_4$-alkyl, $C_1$-$C_4$-haloalkyl, and more preferably hydrogen, methyl, ethyl, trifluoromethyl, $R^{21}$ is preferably hydrogen, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxycarbonyl or $C_1$-$C_6$-haloalkoxycarbonyl, and more preferably hydrogen or methyl, $R^1$ is preferably phenyl which is substituted once by a $Z^4$ substituent and may additionally optionally have further substitution, where the additional substituents are each independently selected from $Z^4$ and $Z^{1-1}$ or $R^1$ is preferably naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 2,3-dihydro-1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, where each of these is substituted once by a $Z^5$ substituent and may additionally optionally have further substitution, where the additional substituents are each independently selected from $Z^5$ and $Z^{1-2}$, or $R^1$ is preferably a 5- or 6-membered heteroaryl radical which is substituted once, either on a carbon by a $Z^6$ substituent or on a nitrogen by a $Z^7$ substituent and may optionally additionally have further substitution, where the additional substituents on carbon are each independently selected from $Z^{1-3}$ and $Z^6$, and the additional substituents on nitrogen are each independently selected from $Z^2$ or $R^1$ is preferably benzofused substituted 5- or 6-membered heteroaryl which is substituted by one $Z^4$ substituent and may additionally optionally have further substitution, where the additional substituents on carbon are each independently selected from $Z^{12}$, and the additional substituents on nitrogen are each independently selected from $Z^2$.

$R^1$ is more preferably phenyl which may contain 1, 2 or 3 substituents, where one substituent is selected from $Z^4$ and any further substituents are selected from the following list: fluorine, chlorine, bromine, iodine, cyano, nitro, hydroxyl, amino, —SH, —C(=O)H, methyl, ethyl, n-propyl, 1-methylethyl, n-butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, n-propoxy, 1-methylethoxy, 1,1-dimethylethoxy, methylcarbonyl, ethylcarbonyl, trifluoromethylcarbonyl, methoxycarbonyl, ethoxycarbonyl, n-propoxycarbonyl, 1-methylethoxycarbonyl, 1,1-dimethylethoxycarbonyl, 1-ethenyloxy, 2-propenyloxy, 2-propynyloxy, methylcarbonyloxy, trifluoroalkylcarbonyloxy, chloromethylcarbonyloxy, methylthio, ethylthio, methylsulphonyl, methylsulphonylamino, trifluoromethylsulphonylamino or -$L^3R^3$, or $R^1$ is more preferably naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 2,3-dihydro-1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, where these may each be substituted at least once by a $Z^5$ substituent and may optionally additionally have further substitution, where the additional substituents are each independently selected from $Z^5$ and the group consisting of methyl, methoxy, cyano, fluorine, chlorine, bromine and iodine, where, in the particularly preferred variant, a total of at most three substituents are present, or $R^1$ is more preferably furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl or pyrazin-2-yl, each of which may contain 1 or 2 substituent(s), where one substituent is either on a carbon and is selected from $Z^6$ or is on a nitrogen and is selected from $Z^7$, and any further substituent is selected from the following list:

substituents on carbon: fluorine, chlorine, bromine, iodine, cyano, nitro, hydroxyl, methyl, ethyl, n-propyl, 1-methylethyl, n-butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, n-propoxy, 1-methylethoxy, 1,1-dimethylethoxy, methylcarbonyl, ethylcarbonyl, trifluoromethylcarbonyl, methoxycarbonyl, ethoxycarbonyl, n-propoxycarbonyl, 1-methylethoxycarbonyl, 1,1-dimethylethoxycarbonyl, 1-ethenyloxy, 2-propenyloxy, 2-propinyloxy, methylcarbonyloxy, trifluoroalkylcarbonyloxy, chloromethylcarbonyloxy, methylcarbonylamino, trifluoroalkylcarbonyl amino, chloromethylcarbonylamino, methylthio, ethylthio, methylsulphinyl, methylsulphonyl, methylsulphonyloxy, trifluoroalkylsulphonyloxy, methylsulphonylamino or trifluoromethylsulphonylamino, substituents on nitrogen: methyl, ethyl, n-propyl, —C(=O)H, methylcarbonyl, trifluoromethylcarbonyl, chloromethylcarbonyl, methylsulphonyl, trifluoromethylsulphonyl, phenylsulphonyl, phenyl or 2-propynyl, or $R^1$ is more preferably indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, which is substituted by a substituent, either on a carbon by $Z^6$ or on a nitrogen by $Z^7$, and additionally optionally bears a further substituent selected from the following list:

substituents on carbon: fluorine, chlorine, bromine, iodine, methyl, methoxy, substituents on nitrogen: methyl, ethyl, n-propyl, —C(=O)H, methylcarbonyl, trifluoromethylcarbonyl, chloromethylcarbonyl, methylsulphonyl, trifluoromethylsulphonyl, phenylsulphonyl, phenyl or 2-propynyl, $Z^{1-1}$ is hydrogen, halogen, cyano, hydroxyl, nitro, —C(=O)NR$^3$R$^4$, —NR$^3$R$^4$, $C_1$-$C_6$-alkyl, $C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_8$-halocycloalkyl, $C_1$-$C_6$-alkoxy-$C_1$-$C_6$-alkyl, $C_1$-$C_6$-alkoxycarbonyl, $C_1$-$C_4$-alkoxy, $C_1$-$C_4$-haloalkoxy, $C_1$-$C_6$-alkylcarbonyloxy, $C_1$-$C_4$-alkylthio, $C_1$-$C_4$-haloalkylthio, $C_3$-$C_6$-cycloalkylthio or -L$^3$Z$^3$, $Z^{1-2}$ are the same or different and are each independently hydrogen, halogen, cyano, nitro, —NR$^3$R$^4$, —C(=O)NR$^3$R$^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_6$-alkoxycarbonyl, $C_1$-$C_4$-alkoxy, $C_1$-$C_4$-haloalkoxy, $C_1$-$C_6$-alkylcarbonyloxy, $C_1$-$C_6$-alkylcarbonylthio, $C_1$-$C_4$-alkylthio or $C_1$-$C_4$-haloalkylthio, $Z^{1-3}$ is hydrogen, halogen, cyano, hydroxyl, nitro, —C(=O)NR$^3$R$^4$, —NR$^3$R$^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-alkylcarbonyl, $C_1$-$C_6$-alkoxycarbonyl, $C_1$-$C_6$-alkoxy, $C_1$-$C_6$-haloalkoxy, $C_1$-$C_6$-alkylcarbonyloxy, $C_1$-$C_6$-alkylthio, $C_1$-$C_6$-haloalkylthio or $C_3$-$C_6$-cycloalkylthio, $Z^2$ is the same or different and is preferably independently hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, phenyl, benzyl, $C_1$-$C_4$-haloalkylsulphonyl, $C_1$-$C_6$-alkoxycarbonyl, $C_1$-$C_6$-haloalkoxycarbonyl, phenylsulphonyl, $C_1$-$C_4$-alkylsulphonyl, —C(=O)H, $C_1$-$C_3$-haloalkylcarbonyl or $C_1$-$C_3$-alkylcarbonyl, $L^3$ is preferably a direct bond, —CH$_2$—, sulphur, oxygen, and more preferably a direct bond, $Z^3$ is preferably a phenyl radical, naphthalenyl or a 5- or 6-membered heteroaryl radical which may contain up to two substituents, where the substituents are each independently selected from the following list:

substituents on carbon: halogen, cyano, nitro, hydroxyl, amino, —SH, $C_2$-$C_4$-alkenyl, $C_2$-$C_4$-alkynyl, $C_2$-$C_4$-haloalkenyl, $C_2$-$C_4$-haloalkynyl, $C_2$-$C_4$-alkoxyalkyl, $C_1$-$C_6$-alkylcarbonyl, $C_1$-$C_6$-haloalkylcarbonyl, $C_1$-$C_6$-alkoxycarbonyl, $C_1$-$C_4$-alkoxy, $C_1$-$C_4$-haloalkoxy, $C_2$-$C_6$-alkenyloxy, $C_2$-$C_6$-alkynyloxy, $C_1$-$C_4$-haloalkylthio, $C_1$-$C_4$-alkylsulphonyl, $C_1$-$C_4$-halo alkylsulphonyl or $C_1$-$C_4$-alkylamino, di($C_1$-$C_4$-alkyl)amino, substituents on nitrogen: $C_1$-$C_6$-alkyl, $C_2$-$C_6$-alkenyl, $C_2$-$C_6$-alkynyl, $C_2$-$C_6$-haloalkenyl, $C_2$-$C_6$-haloalkynyl, $C_1$-$C_4$-alkoxy-$C_1$-$C_4$-alkyl, phenyl, benzyl, $C_1$-$C_4$-haloalkylsulphonyl, $C_1$-$C_6$-alkoxycarbonyl, $C_1$-$C_6$-haloalkoxycarbonyl, phenylsulphonyl, $C_1$-$C_4$-alkylsulphonyl, —C(=O)H, or $C_1$-$C_3$-alkylcarbonyl, and $Z^3$ is more preferably a phenyl radical which may contain up to two substituents, where the substituents are each independently selected from the following list:

chlorine, bromine, iodine, fluorine, cyano, nitro, hydroxyl, amino, —SH, methyl, ethyl, n-propyl, 1-methylethyl, 1,1-dimethylethyl, ethenyl, propen-2-yl, ethynyl, propyn-2-yl, trifluoromethyl, difluoromethyl, methoxymethyl, methylcarbonyl, ethylcarbonyl, trifluoromethylcarbonyl, methoxycarbonyl, ethoxycarbonyl, n-propoxycarbonyl, 1-methylethoxycarbonyl, 1,1-dimethylethoxycarbonyl, methoxy, ethoxy, n-propoxy, 1-methylethoxy, 1,1-dimethylethoxy, trifluoromethoxy, ethenyloxy, 2-propenyloxy, ethynyloxy, 2-propynyloxy, methylthio, ethylthio, trifluoromethylthio, methylsulphonyl, ethylsulphonyl, propylthionyl, 1-methylethylthio, trifluoromethylsulphonyl, methylamino, ethylamino, n-propylamino, 1-methylethylamino, 1,1-dimethylethylamino or dimethylamino, $Z^4$ is preferably C(=O)H, $C_7$-$C_8$-cycloalkyl, $C_3$-$C_6$-cycloalkyl-$C_3$-$C_6$-cycloalkyl, $C_3$-$C_6$-cycloalkenyl, $C_4$-$C_6$-alkoxy-$C_1$-$C_4$-alkyl, $C_4$-$C_6$-alkoxy-$C_1$-$C_4$-alkyl, $C_3$-alkoxy-$C_2$-$C_4$-alkyl, $C_1$-$C_3$-alkoxy-$C_2$-$C_3$-alkoxy-$C_1$-$C_3$-alkyl, $C_1$-$C_4$-alkylthio-$C_1$-$C_2$-alkyl, $C_1$-$C_4$-alkylsulphinyl-$C_1$-$C_2$-alkyl, $C_1$-$C_4$-alkylsulphonyl-$C_1$-$C_2$-alkyl, $C_1$-$C_4$-alkylamino-$C_1$-$C_2$-alkyl, $C_1$-$C_2$-dialkylamino-$C_1$-$C_2$-alkyl, $C_1$-$C_4$-haloalkylamino-$C_1$-$C_2$-alkyl, $C_3$-$C_6$-cycloalkylamino-$C_1$-$C_2$-alkyl, $C_4$-$C_6$-alkylcarbonyl, $C_1$-$C_4$-haloalkylcarbonyl, $C_3$-$C_6$-cycloalkylcarbonyl, $C_3$-$C_6$- cycloalkoxycarbonyl, $C_3$-$C_6$-cycloalkyl-$C_1$-$C_2$-alkoxycarbonyl, $C_3$-$C_6$-cycloalkylaminocarbonyl, $C_1$-$C_4$-haloalkoxy-$C_1$-$C_2$-alkyl, $C_5$-$C_6$-hydroxyalkyl, $C_5$-$C_6$-alkoxy, $C_5$-$C_6$-haloalkoxy, $C_3$-$C_6$-cycloalkoxy, $C_3$-$C_6$-halocycloalkoxy, $C_3$-$C_6$-cycloalkylalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_4$-alkoxy-$C_1$-$C_4$-alkoxy, cyano-$C_1$-$C_4$-alkoxy, $C_1$-$C_4$-haloalkylcarbonyloxy, $C_3$-$C_6$-cycloalkylcarbonyloxy, $C_1$-$C_4$-alkylcarbonyl-$C_1$-$C_4$-alkoxy, $C_5$-$C_6$-alkylthio, $C_5$-$C_6$-haloalkylthio, $C_5$-$C_6$-alkylsulphinyl, $C_5$-$C_6$-haloalkylsulphinyl, $C_5$-$C_6$-alkylsulphonyl, $C_5$-$C_6$-haloalkylsulphonyl, $C_3$-$C_6$-cycloalkylsulphonyl, tri($C_3$-$C_4$-alkyl)silyl, $C_1$-$C_4$-alkylsulphonylamino or $C_1$-$C_4$-haloalkylsulphonylamino, $Z^4$ is more preferably C(=O)H, cycloheptyl, cyclopropylcyclopropyl, cyclohexenyl, n-butoxymethyl, n-propoxyethyl, methoxyethoxymethyl, ethoxyethoxymethyl, methylthiomethyl, ethylthiomethyl, methylsulphinylmethyl, ethylsulphinylmethyl, methylsulphonylmethyl, ethylsulphonylmethyl, methylaminomethyl, ethylaminomethyl, dimethylaminomethyl, trifluoromethylaminomethyl, cyclopropylaminomethyl, n-butylcarbonyl, n-pentylcarbonyl, trifluoromethylcarbonyl, cyclopropylcarbonyl, cyclohexylcarbonyl, cyclopropoxycarbonyl, cyclopentyloxycarbonyl, cyclohexyloxycarbonyl, cyclopropylaminocarbonyl, cyclopentylaminocarbonyl, cyclohexylaminocarbonyl, difluoromethoxymethyl, trifluoromethoxymethyl, n-pentoxy, halo-n-pentoxy, cyclopropoxy, cyclopentyloxy, cyclohexyloxy, cyclopropylmethoxy, allyl, 3-methylbut-2-en-1-yloxy, prop-2-yn-1-yloxy, but-2-yn-1-yloxy, pent-2-yn-1-yloxy, haloalkynyloxy, methoxyethoxy, methoxypropoxy, ethoxyethoxy, 3,3,3-trifluoropropanyloxy, cyanomethoxy, trifluoromethylcarbonyloxy, cyclopropylcarbonyloxy, cyclopentylcarbonyloxy, cyclohexylcarbonyloxy, methylcarbonylmethoxy, pentylsulphonyl, methylsulphonylamino, ethylsulphonylamino or trifluoromethylsulphonylamino, $Z^5$ is preferably benzyl, phenyl, $C_2$-$C_6$-alkenyloxy, $C_2$-$C_6$-alkynyloxy, $C_5$-$C_6$-alkylthio or $C_5$-$C_6$-haloalkylthio, $Z^6$ is preferably $C_3$-$C_6$-cycloalkylcyclopropyl, $C_3$-$C_6$-cycloalkylcyclohexyl or tri($C_3$-$C_4$-alkyl)silyl, $Z^7$ is preferably $C_2$-$C_6$-alkenyl, $C_2$-$C_6$-alkynyl, $C_1$-$C_6$-haloalkyl, $C_3$-$C_6$-cycloalkyl, $C_1$-$C_4$-alkyl-$C_3$-$C_6$-cycloalkyl, $C_3$-$C_6$-cycloalkylcyclopropyl, $C_3$-$C_6$-cycloalkylcyclohexyl, cycloalkylalkyl, $C_1$-$C_4$-alkylsulphonyl, C(=O)H, benzyl or phenyl.

The heteroarylpiperidine and -piperazine derivatives usable in accordance with the invention are defined in general terms by the formula (I). The radical definitions of the radical definitions above and specified below of the formula (I) apply to the end products of the formula (I), and also equally to all intermediates (see also below under "Elucidations of the processes and intermediates").

The radical definitions and elucidations listed above and below, in general terms or in areas of preference, can be combined with one another as desired, i.e. including combinations between the particular areas and areas of preference. They apply both to the end products and correspondingly to precursors and intermediates. Moreover, individual definitions may not apply.

Preference is given to those compounds of the formula (I) in which all radicals have the abovementioned preferred definitions.

Particular preference is given to those compounds of the formula (I) in which all radicals have the abovementioned more preferred definitions.

Very particular preference is given to those compounds of the formula (I) in which all radicals have the abovementioned most preferred definitions.

Preference is additionally given to compounds of the formula (I) and agrochemically active salts, metal complexes and N-oxides thereof, in which:

A is 5-methyl-3-(trifluoromethyl)-1H-pyrazol-1-yl, 5-chloro-2-methylphenyl or 2,5-bis(difluoromethyl)phenyl, $L^1$ is —$CH_2$— or —NH—, $L^2$ is a direct bond, Y is oxygen, X is carbon, p is 0, G is $G^1$, $R^{G1}$ is hydrogen, Q is $Q^{24}$-3, $R^2$ is hydrogen, $R^5$ is hydrogen, $R^1$ is 3-formylphenyl, 2-formylphenyl or 2-[(methylsulphonyl)amino]phenyl.

The radical definitions mentioned above can be combined with one another as desired. Moreover, individual definitions may not apply.

According to the type of substituents defined above, the compounds of the formula (I) have acidic or basic properties and can form salts, possibly also internal salts or adducts, with inorganic or organic acids or with bases or with metal ions. If the compounds of the formula (I) bear amino, alkylamino or other groups which induce basic properties, these compounds can be reacted with acids to give salts, or they are obtained directly as salts by the synthesis. If the compounds of the formula (I) bear hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $C_1$-$C_4$-alkyl groups, mono-, di- and trialkanolamines of $C_1$-$C_4$-alkanols, choline and chlorocholine.

The salts thus obtainable likewise have fungicidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as $NaHSO_4$ and $KHSO_4$. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Useful metal ions are especially the ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period. Here, the metals can be present in the various valencies that they can assume.

Optionally substituted groups may be mono- or polysubstituted, where the substituents in the case of polysubstitutions may be identical or different.

In the definitions of the symbols given in the above formulae, collective terms were used, which are generally representative of the following substituents:

Halogen: fluorine, chlorine, bromine and iodine and preferably fluorine, chlorine, bromine and more preferably fluorine, chlorine.

Alkyl: saturated, straight-chain or branched hydrocarbyl radicals having 1 to 8, preferably 1 to 6 and more preferably 1 to 3 carbon atoms, for example (but not limited to) $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. This definition also applies to alkyl as part of a composite substituent, for example cycloalkylalkyl, hydroxyalkyl etc., unless defined elsewhere like, for example, alkylthio, alkylsulphinyl, alkylsulphonyl, haloalkyl or haloalkylthio. When the alkyl is at the end of a composite substituent, as, for example, in alkylcycloalkyl, the part of the composite substituent at the start, for example the cycloalkyl, may be mono- or polysubstituted, identically or differently and in each case independently, by alkyl. The same also applies to composite substituents in which other radicals, for example alkenyl, alkynyl, hydroxyl, halogen, formyl, etc. are at the end.

Alkenyl: unsaturated, straight-chain or branched hydrocarbyl radicals having 2 to 8, preferably 2 to 6, carbon atoms and one double bond in any position, for example (but not limited to) $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl. This definition also applies to alkenyl as part of a composite substituent, for example haloalkenyl etc., unless defined elsewhere.

Alkynyl: straight-chain or branched hydrocarbyl groups having 2 to 8, preferably 2 to 6, carbon atoms and one triple bond in any position, for example (but not limited to) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1, 1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl. This definition also applies to alkynyl as part of a composite substituent, for example haloalkynyl etc., unless defined elsewhere.

Alkoxy: saturated, straight-chain or branched alkoxy radicals having 1 to 8, preferably 1 to 6 and more preferably 1 to 3 carbon atoms, for example (but not limited to) $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. This definition also applies to alkoxy as part of a composite substituent, for example haloalkoxy, alkynylalkoxy, etc., unless defined elsewhere.

Alkylthio: saturated, straight-chain or branched alkylthio radicals having 1 to 8, preferably 1 to 6 and more preferably 1 to 3 carbon atoms, for example (but not limited to) $C_1$-$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio. This definition also applies to alkylthio as part of a composite substituent, for example haloalkylthio etc., unless defined elsewhere.

Alkoxycarbonyl: an alkoxy group which has 1 to 6, preferably 1 to 3, carbon atoms (as specified above) and is bonded to the skeleton via a carbonyl group (—CO—). This definition also applies to alkoxycarbonyl as part of a composite substituent, for example cycloalkylalkoxycarbonyl etc., unless defined elsewhere.

Alkylsulphinyl: saturated, straight-chain or branched alkylsulphinyl radicals having 1 to 8, preferably 1 to 6 and more preferably 1 to 3 carbon atoms, for example (but not limited to) $C_1$-$C_6$-alkylsulphinyl such as methylsulphinyl, ethylsulphinyl, propylsulphinyl, 1-methylethylsulphinyl, butylsulphinyl, 1-methylpropylsulphinyl, 2-methylpropylsulphinyl, 1, 1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1, 1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1, 1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutyl sulphinyl, 2-ethylbutylsulphinyl, 1,1,2-trimethylpropylsulphinyl, 1,2, 2-trimethylpropylsulphinyl, 1-ethyl-1-methylpropylsulphinyl and 1-ethyl-2-methylpropylsulphinyl. This definition also applies to alkylsulphinyl as part of a composite substituent, for example haloalkylsulphinyl etc., unless defined elsewhere.

Alkylsulphonyl: saturated, straight-chain or branched alkylsulphonyl radicals having 1 to 8, preferably 1 to 6 and more preferably 1 to 3 carbon atoms, for example (but not limited to) $C_1$-$C_6$-alkylsulphonyl such as methylsulphonyl, ethylsulphonyl, propylsulphonyl, 1-methylethylsulphonyl, butylsulphonyl, 1-methylpropylsulphonyl, 2-methylpropylsulphonyl, 1, 1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1, 1-dimethylpropylsulphonyl, 1,2-dimethylpropylsulphonyl, 1-methylpentyl sulphonyl, 2-methylpentylsulphonyl, 3-methylpentylsulphonyl, 4-methylpentylsulphonyl, 1, 1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl. This definition also applies to alkylsulphonyl as part of a composite substituent, for example alkylsulphonylalkyl etc., unless defined elsewhere.

Cycloalkyl: monocyclic, saturated hydrocarbyl groups having 3 to 10, preferably 3 to 8 and more preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Cycloalkenyl: monocyclic, partially unsaturated hydrocarbyl groups having 3 to 10, preferably 3 to 8 and more preferably 3 to 6 carbon ring members, for example (but not limited to) cyclopropenyl, cyclopentenyl and cyclohexenyl. This definition also applies to cycloalkenyl as part of a composite substituent, for example cycloalkenylalkyl etc., unless defined elsewhere.

Cycloalkoxy: monocyclic, saturated cycloalkyloxy radicals having 3 to 10, preferably 3 to 8 and more preferably 3 to 6 carbon ring members, for example (but not limited to) cyclopropyloxy, cyclopentyloxy and cyclohexyloxy. This definition also applies to cycloalkoxy as part of a composite substituent, for example cycloalkoxyalkyl etc., unless defined elsewhere.

Haloalkyl: straight-chain or branched alkyl groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere.

Haloalkenyl and haloalkynyl are defined analogously to haloalkyl except that, instead of alkyl groups, alkenyl and alkynyl groups are present as part of the substituent.

Haloalkoxy: straight-chain or branched alkoxy groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as part of a composite substituent, for example haloalkoxyalkyl etc., unless defined elsewhere.

Haloalkylthio: straight-chain or branched alkylthio groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkylthio such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio. This definition also applies to haloalkylthio as part of a composite substituent, for example haloalkylthioalkyl etc., unless defined elsewhere.

Heteroaryl: 5 or 6-membered, fully unsaturated monocyclic ring system containing one to four heteroatoms from the group of oxygen, nitrogen and sulphur; if the ring contains more than one oxygen atom, they are not directly adjacent;

5-membered heteroaryl containing one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited to) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

nitrogen-bonded 5-membered heteroaryl containing one to four nitrogen atoms, or benzofused nitrogen-bonded 5-membered heteroaryl containing one to three nitrogen atoms: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms in which one or two carbon atoms may be replaced by nitrogen atoms, where these rings are attached to the skeleton via one of the nitrogen ring members, for example (but not limited to) 1-pyrrolyl, 1-pyrazolyl, 1,2,4-triazol-1-yl, 1-imidazolyl, 1,2,3-triazol-1-yl and 1,3,4-triazol-1-yl;

6-membered heteroaryl which contains one to four nitrogen atoms: 6-membered heteroaryl groups which, in addition to carbon atoms, may contain, respectively, one to three and one to four nitrogen atoms as ring members, for example (but not limited to) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzofused 5-membered heteroaryl containing one to three nitrogen atoms or one nitrogen atom and one oxygen or sulphur atom: for example (but not limited to) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl, benzofused 6-membered heteroaryl which contains one to three nitrogen atoms: for example (but not limited to) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl.

This definition also applies to heteroaryl as part of a composite substituent, for example heteroarylalkyl etc., unless defined elsewhere.

Heterocyclyl: three- to fifteen-membered, preferably three- to nine-membered, saturated or partially unsaturated heterocycle containing one to four heteroatoms from the group of oxygen, nitrogen and sulphur: mono-, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl. This definition also applies to heterocyclyl as part of a composite substituent, for example heterocyclylalkyl etc., unless defined elsewhere.

Leaving group: $S_N1$ or $S_N2$ leaving group, for example chlorine, bromine, iodine, alkylsulphonates (—$OSO_2$-alkyl, e.g. —$OSO_2CH_3$, —$OSO_2CF_3$) or arylsulphonates (—$OSO_2$-aryl, e.g. —$OSO_2Ph$, —$OSO_2PhMe$).

Not included are combinations which are against natural laws and which the person skilled in the art would therefore exclude based on his/her expert knowledge. Ring structures having three or more adjacent oxygen atoms, for example, are excluded.

Elucidation of the Preparation Processes and Intermediates

The heteroarylpiperidine and -piperazine derivatives of the formula (I) can be prepared in different ways. Initially, the feasible processes are shown schematically below. Unless stated otherwise, the radicals are each as defined above.

The processes according to the invention for preparing compounds of the formula (I) are optionally performed using one or more reaction auxiliaries.

Useful reaction auxiliaries are, if required, inorganic or organic bases or acid acceptors. These preferably include alkali metal or alkaline earth metal acetates, amides, carbonates, hydrogencarbonates, hydrides, hydroxides or alkoxides, for example sodium acetate, potassium acetate or calcium acetate, lithium amide, sodium amide, potassium amide or calcium amide, sodium carbonate, potassium carbonate or calcium carbonate, sodium hydrogencarbonate, potassium hydrogencarbonate or calcium hydrogencarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, s- or t-butoxide or potassium methoxide, ethoxide, n- or i-propoxide, n-, s- or t-butoxide; and also basic organic nitrogen compounds, for example trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

The processes according to the invention are optionally performed using one or more diluents. Useful diluents include virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters, such as methyl acetate and ethyl acetate, nitriles, for example acetonitrile and propionitrile, amides, for example dimethylformamide, dimethylacetamide and N-methylpyrrolidone, and also dimethyl sulphoxide, tetramethylene sulphone and hexamethylphosphoramide and DMPU.

In the processes according to the invention, the reaction temperatures can be varied within a relatively wide range. In general, the temperatures employed are between 0° C. and 250° C., preferably temperatures between 10° C. and 185° C.

The reaction time varies as a function of the scale of the reaction and of the reaction temperature, but is generally between a few minutes and 48 hours.

The processes according to the invention are generally performed under standard pressure. However, it is also possible to work under elevated or reduced pressure.

For performance of the processes according to the invention, the starting materials required in each case are generally used in approximately equimolar amounts. However, it is also possible to use one of the components used in each case in a relatively large excess.

Process A

Scheme 1: Process A

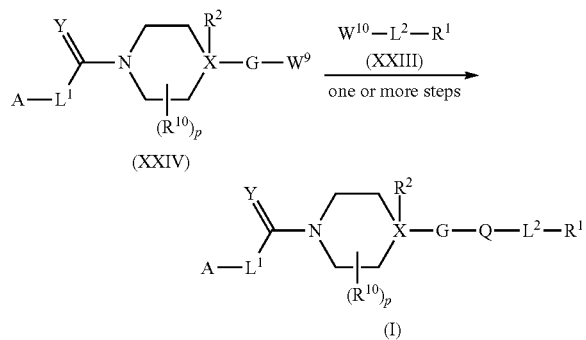

In general, it is possible to prepare compounds of the formula (I) from corresponding compounds (XXIII) and (XXIV) with suitable functional groups $W^9$ and $W^{10}$ (I) (see Scheme 1, process A). The possible functional groups for $W^9$ and $W^{10}$ are, for example, aldehydes, ketones, esters, carboxylic acids, amides, thioamides, nitriles, alcohols, thiols, hydrazines, oximes, amidines, amide oximes, olefins, acetylenes, halides, alkyl halides, methanesulphonates, trifluoromethanesulphonates, boronic acids, boronates etc., which can form the desired heterocycle Q under suitable reaction conditions. There are numerous literature methods for the preparation of heterocycles (see WO2008/013622; Comprehensive Heterocyclic Chemistry Vol. 4-6, A. R. Katritzky and C. W. Rees editors, Pergamon Press, New York, 1984; Comprehensive Heterocyclic Chemistry II, Vol 2-4, A. R. Katritzky, C. W. Rees and E. F. Scriven editors, Pergamon Press, New York, 1996; The Chemistry of Heterocyclic Compounds, E. C. Taylor, editor, Wiley, New York; Rodd's Chemistry of Carbon Compounds, Vol. 2-4, Elsevier, New York; Synthesis, 1982, 6, 508-509; Tetrahedron, 2000, 56, 1057-1094; and literature cited therein).

Process B

Scheme 2: Process B

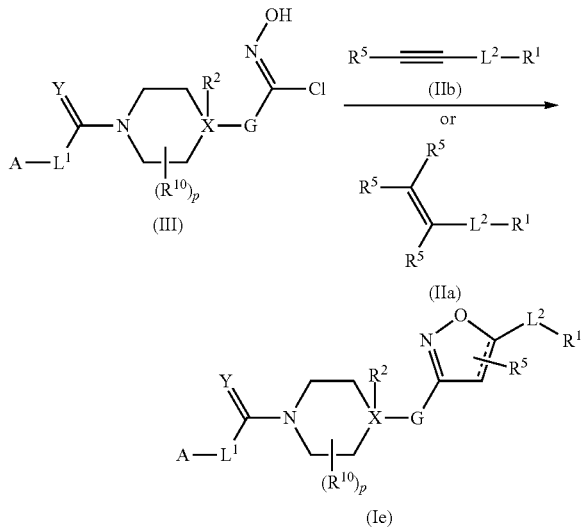

A particular means of preparing compounds of the formula (Ie) from corresponding compounds (III) by reaction with the compounds (IIa) or (IIb) is shown in Scheme 2.

The alkenes and alkynes (IIa) and (IIb) are commercially available or can be prepared from commercially available precursors by methods described in the literature (for example from ketones or aldehydes by a Wittig or Horner-Wadsworth-Emmons olefination: Chem. Rev. 1989, 89, 863-927 and Julia olefination: Tetrahedron Lett., 1973, 14, 4833-4836; Peterson olefination: J. Org. Chem. 1968, 33, 780; with the Bestmann-Ohira reagent: Synthesis 2004, 1, 59-62).

A compound of the general formula (Ie) is obtained from an alkene of the general formula (IIa) or from an alkyne of the formula (IIb) and compound (III) by a cycloaddition reaction (see, for example, WO 08/013622 and Synthesis, 1987, 11, 998-1001).

Process B is performed in the presence of a suitable base. Preferred bases are tertiary amines (e.g. triethylamine), and alkali metal or alkaline earth metal carbonates, hydrogencarbonates and phosphates.

Process B is preferably performed using one or more diluents. In the performance of process B, inert organic solvents are a preferred option (for example toluene and hexane). Water is likewise a possible solvent. Alternatively, process A can be performed in an excess of the alkene (IIa) or of the alkyne (IIb).

The workup is effected by customary methods. If necessary, the compounds are purified by recrystallization or chromatography, or can optionally also be used in the next step without prior purification.

Process C

Scheme 3: Process C

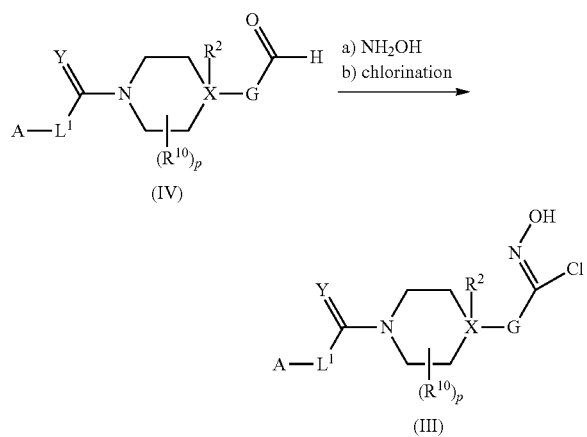

One means of preparing the intermediate (III) from compound (IV) is shown in Scheme 3 (process C).

A compound of the general formula (III) is obtained by condensation of an aldehyde of the formula (IV) with hydroxylamine and subsequent chlorination (see, for example, WO 05/0040159, WO 08/013622 and *Synthesis*, 1987, 11, 998-1001).

In process C, aldehyde (IV) and hydroxylamine are first reacted (Scheme 4, step (a)). The corresponding oxime is subsequently chlorinated in the presence of a suitable chlorinating agent. Preferred chlorinating reagents are N-chlorosuccinimide, HClO and chlorine. After step (a) of process C, the reaction mixture can be worked up by customary methods or converted further directly in step (b).

Process C is preferably performed using one or more diluents. In step (a) of process C according to the invention, preference is given to using protic solvents, for example ethanol, as the solvent. After the formation of the corresponding oxime from compound (IV), the reaction mixture is diluted in step (b) with a further solvent, for example tetrahydrofuran, and then aqueous sodium hypochlorite is added. The chlorination can likewise be effected with the aid of N-chlorosuccinimide in DMF.

The workup is effected by customary methods. If necessary, the compounds are purified by recrystallization or chromatography, or can optionally also be used in the next step without prior purification.

Process D

Scheme 4: Process D

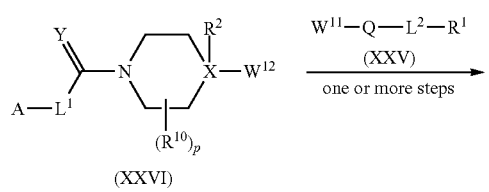

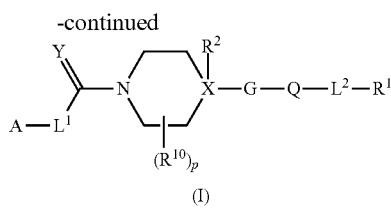

In general, it is possible to prepare the intermediate of the formula (I) from corresponding compounds (XXVI) and (XXV) with suitable functional groups $W^{11}$ and $W^{12}$, (I) (see Scheme 4, process D). The possible functional groups for $W^{11}$ and $W^{12}$ are, for example, aldehydes, ketones, esters, carboxylic acids, amides, thioamides, nitriles, alcohols, thiols, hydrazines, oximes, amidines, amide oximes, olefins, acetylenes, halides, alkyl halides, methanesulphonates, trifluoromethanesulphonates, boric acid, boronates etc. They can form the desired 5-membered heterocycle G under suitable reaction conditions. There are numerous literature methods for the preparation of heterocycles (see WO 2008/013622; *Comprehensive Heterocyclic Chemistry* Vol. 4-6, editors: A. R. Katritzky and C. W. Rees, Pergamon Press, New York, 1984; *Comprehensive Heterocyclic Chemistry II*, Vol. 2-4, editors: A. R. Katritzky, C. W. Rees and E. F. Scriven, Pergamon Press, New York, 1996; *The Chemistry of Heterocyclic Compounds*, editor: E. C. Taylor, Wiley, New York; *Rodd's Chemistry of Carbon Compounds*, Vol. 2-4, Elsevier, New York).

Process E

Scheme 5: Process E

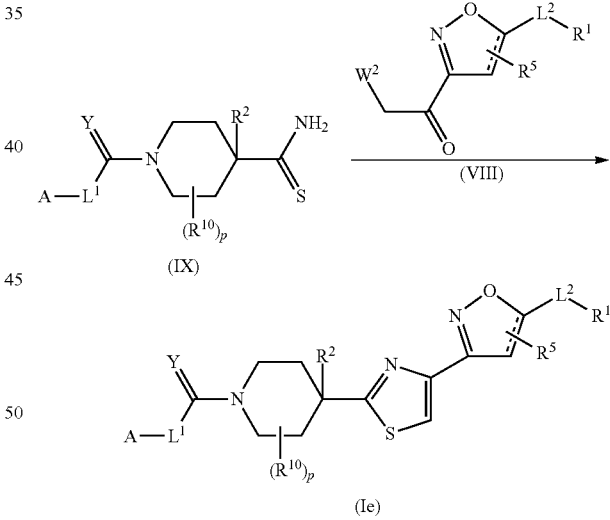

A particular means of synthesizing compounds of the formula (Ie) from compounds (IX) with the compounds (VIII) is shown in Scheme 5 (process E).

Thiocarboxamides (IX) are obtainable by methods known from the literature, for example by thionating the commercially available corresponding carboxamide by using, for example, Lawesson's reagent (WO2008/013622, *Org. Synth*. Vol. 7, 1990, 372).

☐-Halo ketones or corresponding ketones having a leaving group (e.g. toluenesulphonyloxy ketones) are also obtainable by methods known from the literature (for examples see WO2008/013622), (Scheme 6).

Scheme 6

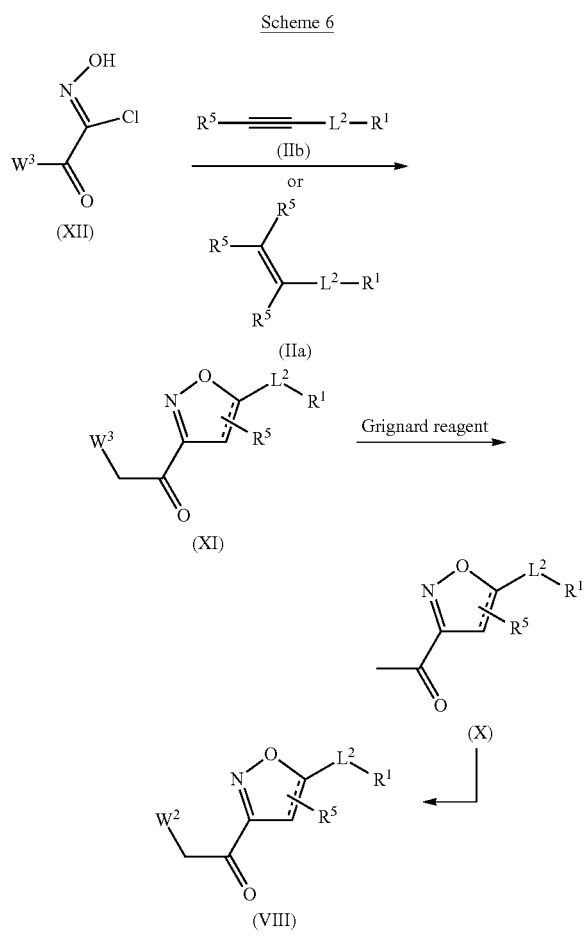

The thiazoles (Ie) are obtained by a Hantzsch thiazole synthesis from the thiocarboxamides (IX) and □-halo ketones or corresponding ketones having a leaving group (VIII) (see, for example, "Comprehensive Heterocyclic Chemistry", Pergamon Press, 1984; vol. 6, pages 235-363, "Comprehensive Heterocyclic Chemistry II", Pergamon Press, 1996; vol. 3, pages 373-474 and references cited therein, and WO 07/014290).

Process E is preferably performed using one or more diluents. In the performance of process E, inert organic solvents are a preferred option (for example N,N-dimethylformamide and ethanol).

If appropriate, an auxiliary base is used, for example triethylamine.

If necessary, the compounds are purified by recrystallization or chromatography, or can optionally also be used in the next step without prior purification.

Process F

Scheme 7: Process F

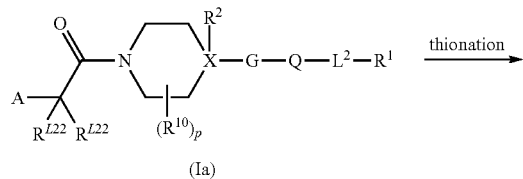

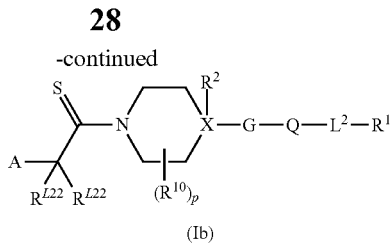

The amides (Ia) obtained in the performance of process G according to the invention (Scheme 8) can be converted by means of methods described in the literature to the corresponding thioamides (Ib) (e.g. *Bioorganic & Medicinal Chemistry Letters*, 2009, 19(2), 462-468). This involves reacting the compounds of the formula (Ia) typically with phosphorus pentasulphide or 2,4-bis(4-methoxyphenyl)-1,3-dithia-2,4-diphosphetane 2,4-disulphide (Lawesson's reagent) (see Scheme 7, Process F).

Process F according to the invention is preferably carried out using one or more diluents. The preferred solvents are toluene, tetrahydrofuran and 1,2-dimethoxyethane.

After the reaction has ended, the compounds (Ib) are separated from the reaction mixture by one of the customary separation techniques. If necessary, the compounds are purified by recrystallization or chromatography.

Process G

Scheme 8: Process G

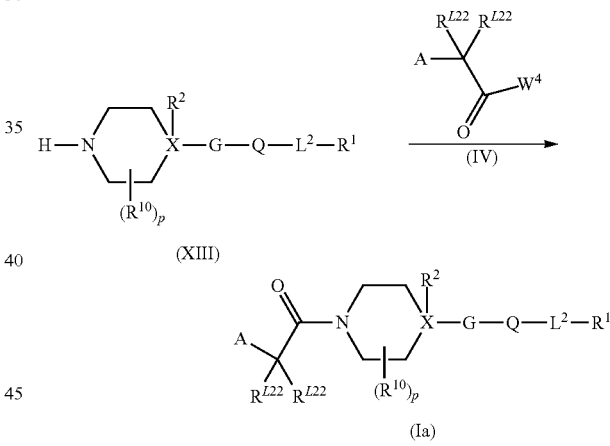

One means of preparing compounds of the formula (Ia) from corresponding compounds (XIII) with the compounds (IV) is shown in Scheme 8 (process G).

Compounds (IV) are either commercially available or can be prepared by processes described in the literature (see, for example, WO 2008/013622 and WO 2008/013925).

A compound with the general formula (Ia) can be synthesized analogously to methods described in the literature (see, for example WO 2007/147336), by a coupling reaction of a compound with the corresponding general formula (XIII) with a substrate of the general formula (IV) where $W^4$ is chlorine, optionally in the presence of an acid scavenger/base.

At least one equivalent of an acid scavenger/a base (for example Hünig's base, triethylamine or commercially available polymeric acid scavengers) is used, in relation to the starting material of the general formula (XIII). If the starting material is a salt, at least two equivalents of the acid scavenger are required.

Alternatively, a compound of the formula (Ia) can also be synthesized from the corresponding compound of the formula (XIII) with a substrate of the formula (IV) where $W^4$ is hydroxyl in the presence of a coupling reagent, analogously to methods described in the literature (for example Tetrahedron 2005, 61, 10827-10852, and references cited therein).

Suitable coupling reagents are, for example, peptide coupling reagents (for example N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

After the reaction has ended, the compounds (Ia) are separated from the reaction mixture by one of the customary separation techniques. If necessary, the compounds are purified by recrystallization or chromatography.

Process H

Scheme 9: Process H

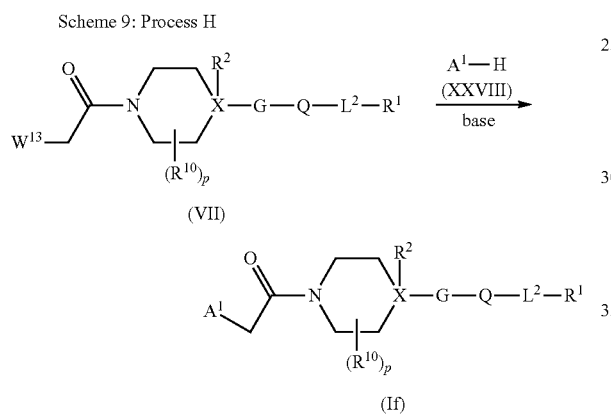

(VII)

(If)

One means of preparing compounds of the formula (If) from corresponding compounds (VII) with the compounds (XXVIII) is shown in Scheme 9 (process H).

The starting materials (VII) in which $W^{13}$ is a leaving group can be prepared by means of methods described in the literature from compounds (V), (XVIIe) (FIG. 1) or from (XIII) (see, for example, mesylation: *Organic Letters*, 2003, 2539-2541; tosylation: JP60156601; halogenation: *Australian Journal of Chemistry*, 1983, 2095-2110). Typically, the compounds of the formula (VII, $W^{13}$=chlorine) are prepared proceeding from an amine of the formula (XIII) and chloroacetyl chloride. The compounds (V) in (FIG. 1) are prepared analogously to process G with glycolic acid or hydroxyacetyl chloride from (XIII) (see, for example, WO 2007103187, WO 2006117521, *Bioorganic & Medicinal Chemistry Letters*, 2007, 6326-6329).

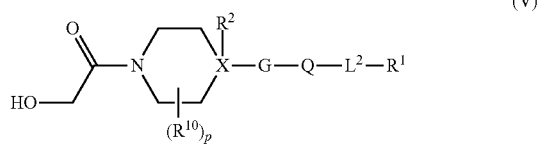

(V)

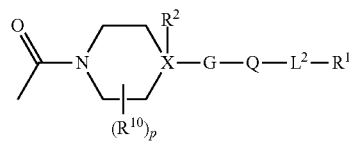

(XVIIe)

At least one equivalent of a base (e.g. sodium hydride, potassium carbonate) is used in relation to the starting material of the general formula (XXVIII).

After the reaction has ended, the compounds (If) are separated from the reaction mixture by one of the customary separation techniques. If necessary, the compounds are purified by recrystallization or chromatography, or can, if desired, also be used in the next step without prior purification.

Process I

Scheme 10: Process I

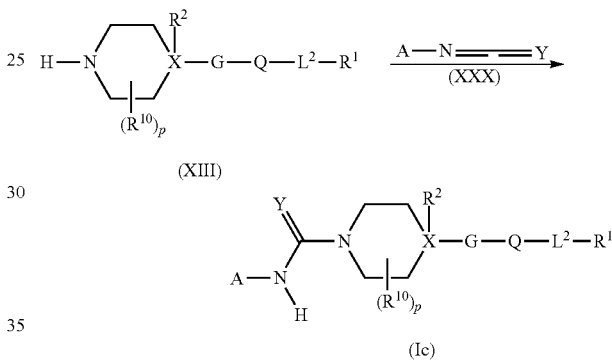

(XIII)

(Ic)

One means of preparing compounds of the formula (Ic) from corresponding compounds (XIII) with the compounds (XXX) is shown in Scheme 10 (process I).

A compound with the general formula (Ic) can be synthesized analogously to methods described in the literature (see, for example WO 2009/055514), by a coupling reaction of a compound with the corresponding general formula (XIII) with a substrate of the general formula (XXX), optionally in the presence of an acid scavenger/base, for example triethylamine, 1, 8-diazabicyclo[5.4.0]undec-7-ene or Hünig's base.

After the reaction has ended, the compounds (Ic) are separated from the reaction mixture by one of the customary separation techniques. If necessary, the compounds are purified by recrystallization or chromatography.

Process J

Scheme 11: Process J

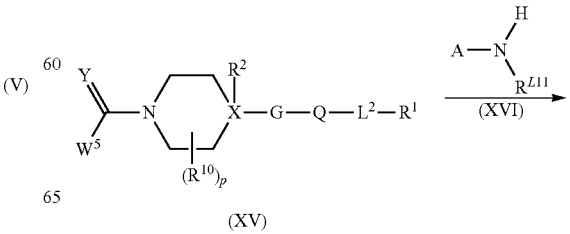

(XV)

-continued

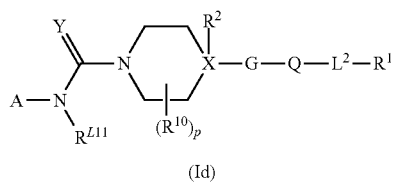

(Id)

One means of preparing compounds of the formula (Id) from corresponding compounds (XVa, see FIG. 2) or (XVb, see FIG. 2) with the compounds (XVI) is shown in Scheme 11 (process J).

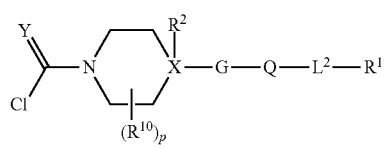

(XVa)

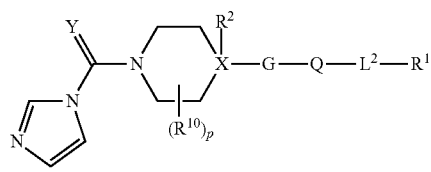

(XVb)

The starting materials, carbamoyl and thiocarbamoyl chlorides of the formula (XVa), can be prepared by means of methods described in the literature from compounds (XIII) (see, for example, *Tetrahedron*, 2008, 7605; *Journal of Organic Chemistry*, 2004, 3787; *Journal of Organic Chemistry*, 1983, 4750; *European Journal of Organic Chemistry*, 2006, 1177). Typically, the compounds of the formula (XVa) are prepared proceeding from amines of the formula (XIII) and phosgene, thiophosgene or the equivalents thereof.

The alternative starting materials, carbamoyl- and thiocarbamoylimidazoles of the formula (XVb), can be prepared by means of methods described in the literature (see, for example, *Tetrahedron Letters*, 2008, 5279; *Tetrahedron*, 2005, 7153). Typically, the compounds of the formula (XVb, $W^5$=imidazol-1-yl) are prepared proceeding from amines of the formula (XIII) and 1,1'-carbonyldiimidazole or 1,1'-thiocarbonyldiimidazole.

Process J is optionally performed in the presence of a suitable acid acceptor.

The compounds (Id) obtained in the performance of process J according to the invention can alternatively in some cases also be obtained without using an acid acceptor, as the corresponding acid chlorides [(Id)-HCl]. If required, the compounds (Id) are released by customary methods.

After the reaction has ended, the compounds (Id) are separated from the reaction mixture by one of the customary separation techniques. If necessary, the compounds are purified by recrystallization or chromatography.

Process K

Scheme 12: Process K

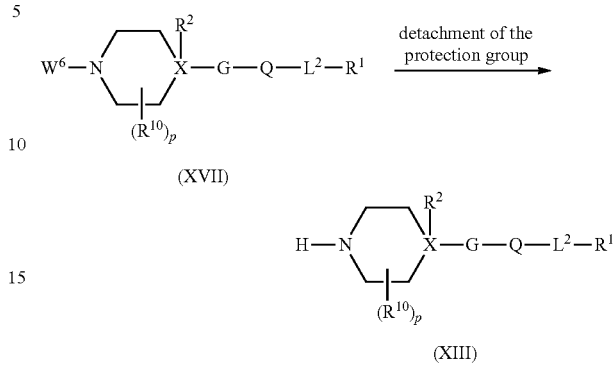

One means of preparing compounds of the formula (XIII) from corresponding compounds (XVII) is shown in Scheme 12 (process K).

A compound of the formula (XVII) is converted to a compound of the formula (XIII) by suitable methods for removing protecting groups described in the literature ("*Protective Groups in Organic Synthesis*"; Theodora W. Greene, Peter G. M. Wuts; Wiley-Interscience; Third Edition; 1999 494-653).

tert-Butoxycarbonyl and benzyloxycarbonyl protecting groups can be removed in an acidic medium (for example with hydrochloric acid or trifluoroacetic acid). Acetyl protecting groups can be removed under basic conditions (for example with potassium carbonate or caesium carbonate). Benzylic protecting groups can be removed hydrogenolytically with hydrogen in the presence of a catalyst (for example palladium on activated carbon).

Acids which can be used for this reaction of deprotecting tert-butoxycarbonyl and benzyloxycarbonyl groups are, for example, trifluoroacetic acid, hydrochloric acid or other acids as described in the literature (for example "*Protective Groups in Organic Synthesis*"; Theodora W. Greene, Peter G. M. Wuts; Wiley-Interscience; Third Edition; 1999; 494-653).

After the reaction has ended, the compounds (XIII) are separated from the reaction mixture by one of the customary separation techniques. If necessary, the compounds are purified by recrystallization or chromatography, or can, if desired, also be used in the next step without prior purification. It is also possible to isolate the compound of the general formula (XIII) as a salt, for example as a salt of hydrochloric acid or of trifluoroacetic acid.

Process L

Scheme 13: Process L

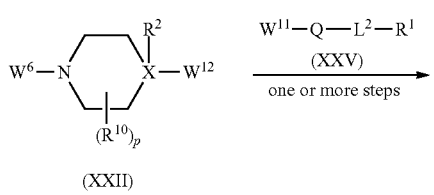

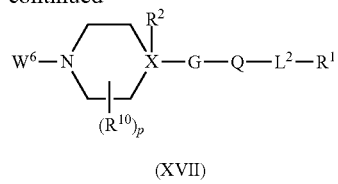

(XVII)

In general, it is possible to prepare the intermediate (XVII) from corresponding compounds (XXII) with compounds (XXV). Process L (Scheme 13) is performed analogously to process D (Scheme 4).

Process M

Scheme 14: Process M

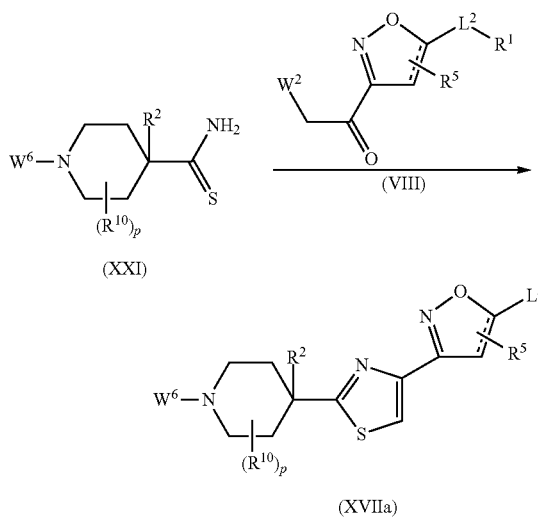

(XVIIa)

Another means of preparing the intermediate of the formula (XVIIa) from corresponding compounds (XXI) is shown in Scheme 14 (process M). Compounds (XXI) are either commercially available or can be prepared by processes described in the literature (see, for example, WO 2008/013622 and WO 2007/014290). Process M is performed analogously to process E (Scheme 5).

Process N

Scheme 15: Process N

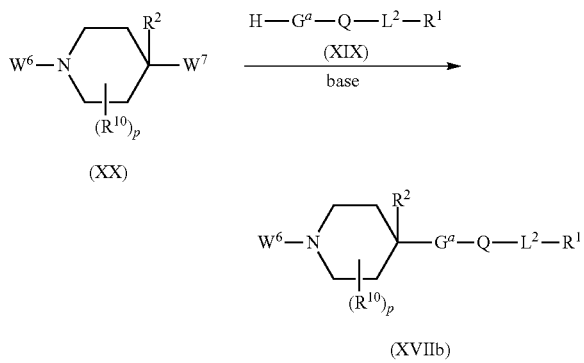

(XVIIb)

A compound with the general formula (XVIIb) can be synthesized analogously to methods described in the literature by a coupling reaction of a compound with the corresponding general formula (XX) with a substrate of the general formula (XIX), optionally in the presence of a base (Scheme 15, process N). (See, for example, for Zn/Pd coupling: WO 2008/147831, WO 2006/106423 (pyridine), Shakespeare, W. C. et al Chem. Biol. Drug Design 2008, 71, 97-105 (pyrimidine derivatives), Pasternak, A. et al Bioorg. Med. Chem. Lett. 2008, 18, 994-998 (diazines); Coleridge, B. M.; Bello, C. S.; Leitner, A. Tetrahedron Lett. 2009, 50, 4475-4477; Bach, T., Heuser, S. Angew. Chem. Int. Ed. 2001, 40, 3184-3185. (thiazoles); for nucleophilic substitutions: WO 2008/104077; WO 2006/084015 (pyrazoles with N-substitution).)

At least one equivalent of a base (e.g. sodium hydride, potassium carbonate) is used in relation to the starting material of the general formula (XX).

After the reaction has ended, the compounds (XVIIb) are separated from the reaction mixture by one of the customary separation techniques. If necessary, the compounds are purified by recrystallization or chromatography, or can, if desired, also be used in the next step without prior purification.

Process O

Scheme 16: Process O

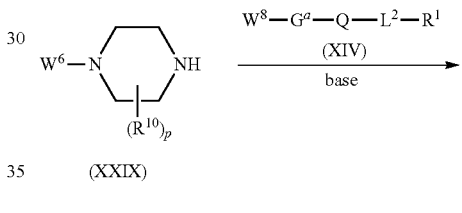

(XXIX)

(XVIIc)

A compound having the general formula (XVIIc) can be synthesized analogously to methods described in the literature (see, for example, for nucleophilic substitutions: Li, C. S., Belair, L., Guay, J. et al Bioorg. Med. Chem. Lett. 2009, 19, 5214-5217; WO 2008/062276; for copper couplings: Yeh, V. S. C.; Wiedeman, P. E. Tetrahedron Lett. 2006, 47, 6011-6016; for palladium couplings: WO 2008/157500) by a coupling reaction of a compound having the corresponding general formula (XXIX) with a substrate of the general formula (XIV), optionally in the presence of a base (Scheme 16, process O).

At least one equivalent of a base (e.g. sodium hydride, potassium carbonate) is used in relation to the starting material of the general formula (XXIX).

After the reaction has ended, the compounds (XVIIc) are separated from the reaction mixture by one of the customary separation techniques. If necessary, the compounds are purified by recrystallization or chromatography, or can, if desired, also be used in the next step without prior purification.

Process P

Scheme 17: Process P

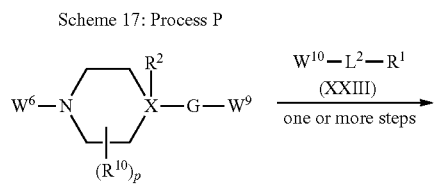

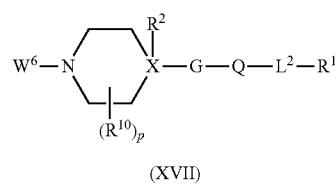

In general, it is possible to prepare the intermediate (XVII) from corresponding compounds (XX VII) and (XXIII). Process P (Scheme 17) is performed analogously to process A (Scheme 1).

Process Q

Scheme 18: Process Q

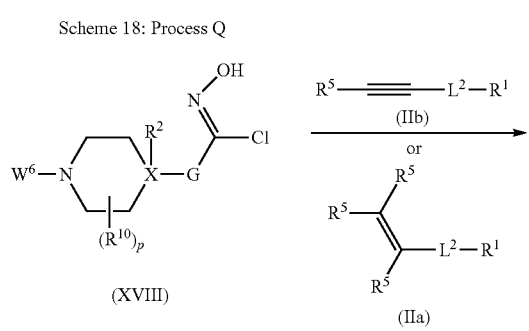

A particular means of preparing the intermediate (XVIId) from corresponding compounds (XVIII) is shown in Scheme 18 (process Q). The starting materials of the formula (XVIII) can be prepared by means of methods described in the literature (see, for example, WO 2008/013622), and process Q is performed analogously to process B (Scheme 2).

The invention further provides for the non-medical use of the inventive heteroarylpiperidine and -piperazine derivatives of the formula (I) for control of unwanted microorganisms.

Novel compounds are those of the formula (VII)

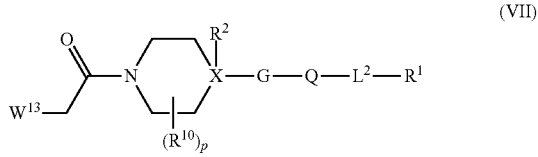

and salts, metal complexes and N-oxides thereof, in which the symbols $R^2$, X, G, Q, $L^2$, $R^1$, $R^{10}$ and p each have the above-specified general, preferred, more preferred or most preferred definitions and $W^{13}$ is a leaving group.

Novel compounds are those of the formula (XVIId)

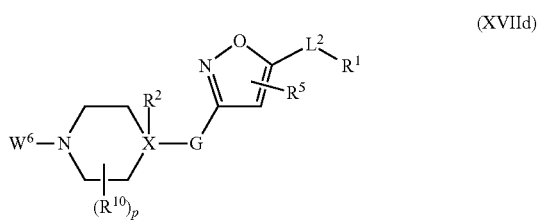

for example (XVIIf)

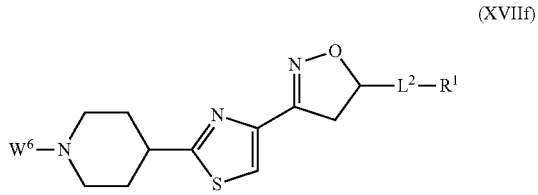

and salts, metal complexes and N-oxides thereof, in which the symbol $W^6$ is acetyl, $C_1$-$C_4$-alkoxycarbonyl, benzyl or benzyloxycarbonyl and the X, $L^2$, p, $R^1$, $R^2$, $R^5$ and $R^{10}$ radicals each have the above-specified general, preferred, more preferred or most preferred definitions.

Novel compounds are those of the formula (XIIIa)

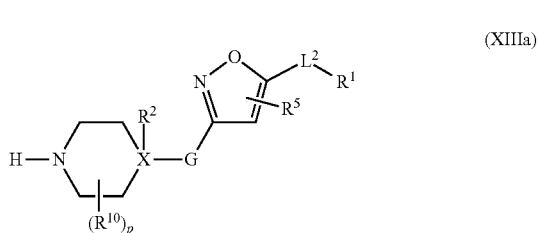

for example (XIIIb)

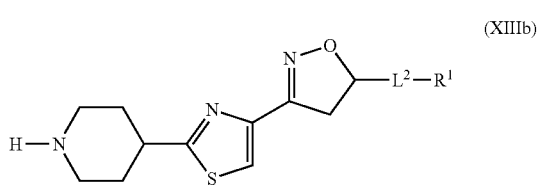

and salts, metal complexes and N-oxides thereof, in which the symbols X, $L^2$, p, G, $R^1$, $R^2$, $R^5$ and $R^{10}$ have the above-specified general, preferred, more preferred or most preferred definitions.

The invention further provides a composition for controlling unwanted microorganisms, comprising at least one heteroarylpiperidine and -piperazine derivative according to the present invention.

The invention also relates to a method for controlling unwanted microorganisms, characterized in that the inventive heteroarylpiperidine and -piperazine derivatives are applied to the microorganisms and/or in their habitat.

The invention further relates to seed which has been treated with at least one inventive heteroarylpiperidine and -piperazine derivative.

The invention finally provides a method for protecting seed against unwanted microorganisms by using seed treated with at least one heteroarylpiperidine and -piperazine derivative according to the present invention.

The inventive substances have potent microbicidal activity and can be used for control of unwanted microorganisms, such as fungi and bacteria, in crop protection and in the protection of materials.

The inventive heteroarylpiperidine and -piperazine derivatives of the formula (I) have very good fungicidal properties and can be used in crop protection, for example for control of Plasmodiophoromycetes, Oomycetes, Chytridiomycetes, Zygomycetes, Ascomycetes, Basidiomycetes and Deuteromycetes.

Bactericides can be employed in crop protection, for example, for controlling Pseudomonadaceae, Rhizobiaceae, Enterobacteriaceae, Corynebacteriaceae and Streptomycetaceae.

The inventive fungicidal compositions can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The inventive compositions for controlling phytopathogenic fungi in crop protection comprise an effective but non-phytotoxic amount of the inventive active ingredients. An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

Plants which can be treated in accordance with the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants in gardens and woods; and genetically modified varieties of each of these plants.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* or *Phakopsora meibomiae*; *Puccinia* species, for example *Puccinia recondita*, *Puccinia graminis* or *Puccinia striiformis*; *Uromyces* species, for example *Uromyces appendiculatus*;

diseases caused by pathogens from the group of the Oomycetes, for example *Albugo* species, for example *Albugo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladosporium* species, for example *Cladosporium cucumerinum*; *Cochliobolus* species, for example *Cochliobolus sativus* (conidial form: *Drechslera*, syn: *Helminthosporium*) or *Cochliobolus miyabeanus*; *Colletotrichum* species, for example *Colletotrichum lindemuthianum*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola*, *Mycosphaerella arachidicola* or *Mycosphaerella fijiensis*; *Phaeosphaeria* species, for example *Phaeosphaeria nodorum*; *Pyrenophora* species, for example *Pyrenophora teres* or *Pyrenophora tritici repentis*; *Ramularia* species, for example *Ramularia collo-cygni* or *Ramularia areola*; *Rhynchosporium* species, for example *Rhynchosporium secalis*; *Septoria* species, for example *Septoria apii* or *Septoria lycopersici*; *Stagonospora* species, for example *Stagonospora nodorum*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Plasmodiophora* species, for example *Plasmodiophora brassicae*; *Rhizoctonia* species, for example *Rhizoctonia solani*; *Sarocladium* species, for example *Sarocladium oryzae*; *Sclerotium* species, for example *Sclerotium oryzae*; *Tapesia* species, for example *Tapesia acuformis*; *Thielaviopsis* species, for example *Thielaviopsis basicola*;

ear and panicle diseases (including maize cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Stagnospora* species, for example *Stagnospora nodorum*;

diseases caused by smut fungi, for example *Sphacelotheca* species, for example *Sphacelotheca reiliana*; *Tilletia* species, for example *Tilletia caries* or *Tilletia controversa*; *Urocystis* species, for example *Urocystis occulta*; *Ustilago* species, for example *Ustilago nuda*;

fruit rot caused, for example, by *Aspergillus* species, for example *Aspergillus flavus*; *Botrytis* species, for example *Botrytis cinerea*; *Penicillium* species, for example *Penicillium expansum* or *Penicillium purpurogenum*; *Rhizopus* species, for example *Rhizopus stolonifer*; *Sclerotinia* species, for example *Sclerotinia sclerotiorum*; *Verticilium* species, for example *Verticilium alboatrum*;

seed- and soil-borne rot and wilt diseases, and also diseases of seedlings, caused, for example, by *Alternaria* species, for example *Alternaria brassicicola*; *Aphanomyces* species, for example *Aphanomyces euteiches*; *Ascochyta* species, for example *Ascochyta lentis*; *Aspergillus* species, for example *Aspergillus flavus*; *Cladosporium* species, for example *Cladosporium herbarum*; *Cochliobolus* species, for example *Cochliobolus sativus* (conidial form: *Drechslera*, *Bipolaris* syn: *Helminthosporium*); *Colletotrichum* species, for example *Colletotrichum coccodes*; *Fusarium* species, for example *Fusarium culmorum*; *Gibberella* species, for example *Gibberella zeae*; *Macrophomina* species, for example *Macrophomina phaseolina*; *Microdochium* species, for example *Microdochium nivale*; *Monographella* species, for example *Monographella nivalis*; *Penicillium* species, for example *Penicillium expansum*; *Phoma* species, for example *Phoma lingam*; *Phomopsis* species, for example *Phomopsis sojae*; *Phytophthora* species, for example *Phytophthora cactorum*; *Pyrenophora* species, for example *Pyrenophora graminea*; *Pyricularia* species, for example *Pyricularia oryzae*; *Pythium* species, for example *Pythium ultimum*; *Rhizoctonia* species, for example *Rhizoctonia solani*; *Rhizopus* species, for example *Rhizopus oryzae*; *Sclerotium* species, for example *Sclerotium rolfsii*; *Septoria* species, for example *Septoria nodorum*; *Typhula* species, for example *Typhula incarnata*; *Verticillium* species, for example *Verticillium dahliae*;

cancers, galls and witches' broom caused, for example, by *Nectria* species, for example *Nectria galligena*;

wilt diseases caused, for example, by *Monilinia* species, for example *Monilinia laxa*;

deformations of leaves, flowers and fruits caused, for example, by *Exobasidium* species, for example *Exobasidium vexans*; *Taphrina* species, for example *Taphrina deformans*;

degenerative diseases in woody plants, caused, for example, by *Esca* species, for example *Phaeomoniella chlamydospora*, *Phaeoacremonium aleophilum* or *Fomitiporia mediterranea*; *Ganoderma* species, for example *Ganoderma boninense*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), dechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*, *Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum*, *Fusarium orthoceras*, *Fusarium semitectum*, *Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum*, *Pythium irregulare*, *Pythium debaryanum*, *Pythium myriotylum*, *Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive active ingredients also have very good fortifying action in plants. They can therefore be used to mobilize the plant's own defences against attack by unwanted microorganisms.

Plant-fortifying (resistance-inducing) substances are understood to mean, in the present context, those substances which are capable of stimulating the defence system of plants in such a way that the treated plants, when subsequently inoculated with unwanted microorganisms, develop a high degree of resistance to these microorganisms.

In the present case, unwanted microorganisms are understood to mean phytopathogenic fungi and bacteria. The inventive substances can thus be used to protect plants for a certain period after the treatment against attack by the pathogens mentioned. The period for which protection is provided generally extends over 1 to 10 days, preferably 1 to 7 days, after the treatment of the plants with the active ingredients.

The fact that the active ingredients are well tolerated by plants at the concentrations required for controlling plant diseases allows the treatment of above-ground parts of plants, of propagation stock and seeds, and of the soil.

The inventive active ingredients can be used particularly successfully to control diseases in viticulture and potato, fruit and vegetable growing, for example especially against powdery mildew fungi, Oomycetes, for example *Phytophthora, Plasmopara, Pseudoperonospora* and *Pythium* species.

The inventive active ingredients are also suitable for enhancing the yield of crops. In addition, they have low toxicity and are well tolerated by plants.

If appropriate, the inventive compounds can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be used as insecticides. If appropriate, they can also be used as intermediates or precursors for the synthesis of other active ingredients.

The inventive active ingredients, when they are well tolerated by plants, have favourable homeotherm toxicity and are well tolerated by the environment, are suitable for protecting plants and plant organs, for enhancing harvest yields, for improving the quality of the harvested material in agriculture, in horticulture, in animal husbandry, in forests, in gardens and leisure facilities, in the protection of stored products and of materials, and in the hygiene sector. They can preferably be used as crop protection agents. They are effective against normally sensitive and resistant species and against all or some stages of development.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation/the active ingredient itself into the soil.

The inventive active ingredients or compositions can also be used in the protection of materials, for protecting industrial materials against attack and destruction by unwanted microorganisms, for example fungi.

Industrial materials in the present context are understood to mean inanimate materials which have been prepared for use in industry. For example, industrial materials which are to be protected by inventive active ingredients from microbial alteration or destruction may be adhesives, sizes, paper and board, textiles, leather, wood, paints and plastic articles, cooling lubricants and other materials which can be infected with or destroyed by microorganisms. The range of materials to be protected also includes parts of production plants, for example cooling water circuits, which may be impaired by the proliferation of microorganisms. Industrial materials within the scope of the present invention preferably include adhesives, sizes, paper and cardboard, leather, wood, paints, cooling lubricants and heat transfer fluids, more preferably wood. The inventive active ingredients or compositions may prevent adverse effects, such as rotting, decay, discoloration, decoloration or formation of mould.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, whether unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Microorganisms capable of degrading or altering the industrial materials include, for example, bacteria, fungi, yeasts, algae and slime organisms. The inventive active ingredients preferably act against fungi, especially moulds, wood-discoloring and wood-destroying fungi (Basidiomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

The present invention further relates to a composition for controlling unwanted microorganisms, comprising at least one of the inventive heteroarylpiperidine and -piperazine derivatives. These are preferably fungicidal compositions which comprise agriculturally suitable auxiliaries, solvents, carriers, surfactants or extenders.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid carriers include: for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally suitable are oligo- or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural products impregnated with active ingredient, synthetic substances impregnated with active ingredient, fertilizers and also microencapsulations in polymeric substances.

The active ingredients can be applied as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspoemulsion concentrates, natural products impregnated with active ingredient, synthetic substances impregnated with active ingredient, fertilizers and also microencapsulations in polymeric substances. Application is accomplished in a customary manner, for example by watering, spraying, atomizing, broadcasting, dusting, foaming, spreading, etc. It is also possible to apply the active ingredients by the ultra-low volume method, or to inject the active ingredient preparation or the active ingredient itself into the soil. It is also possible to treat the seed of the plants.

The formulations mentioned can be prepared in a manner known per se, for example by mixing the active ingredients with at least one customary extender, solvent or diluent, emulsifier, dispersant and/or binder or fixing agent, wetting agent, a water repellent, if appropriate siccatives and UV stabilizers and if appropriate dyes and pigments, antifoams, preservatives, secondary thickeners, stickers, gibberellins and also other processing auxiliaries.

The present invention includes not only formulations which are already ready for use and can be deployed with a suitable apparatus to the plant or the seed, but also commercial concentrates which have to be diluted with water prior to use.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The auxiliaries used may be those substances which are suitable for imparting particular properties to the composition itself or and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkypyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

The inventive compositions may additionally comprise further components, for example surfactants. Suitable surfactants are emulsifiers and/or foam formers, dispersants or wetting agents having ionic or nonionic properties, or mixtures of these surfactants. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes.

The formulations contain generally between 0.05 and 99% by weight, 0.01 and 98% by weight, preferably between 0.1 and 95% by weight, more preferably between 0.5 and 90% of active ingredient, most preferably between 10 and 70 percent by weight.

The formulations described above can be used in an inventive method for controlling unwanted microorganisms, in which the inventive heteroarylpiperidine and -piperazine derivatives are applied to the microorganisms and/or in their habitat.

The inventive active ingredients can also be used, as such or in formulations thereof, in a mixture with known fungicides, bactericides, acaricides, nematicides or insecticides, in order thus to broaden, for example, the activity spectrum or to prevent development of resistance.

Useful mixing partners include, for example, known fungicides, insecticides, acaricides, nematicides or else bactericides (see also Pesticide Manual, 14th ed.).

A mixture with other known active ingredients, such as herbicides, or with fertilizers and growth regulators, safeners and/or semiochemicals is also possible.

Application is accomplished in a customary manner appropriate for the use forms.

The invention further comprises a method for treating seed.

A further aspect of the present invention relates in particular to seed treated with at least one of the inventive heteroarylpiperidine and -piperazine derivatives. The inventive seeds are used in methods for protection of seed from phytopathogenic harmful fungi. In these methods, seed treated with at least one inventive active ingredient is used.

The inventive active ingredients or compositions are also suitable for the treatment of seed. A large part of the damage to crop plants caused by harmful organisms is triggered by the infection of the seed during storage or after sowing both during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic harmful fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection agents after planting or after emergence of the plants. It is also desirable to optimize the amount of the active ingredient used so as to provide the best possible protection for the seed and the germinating plant from attack by phytopathogenic fungi, but without damaging the plant itself by the active ingredient used. In particular, methods for the treatment of seed should also take account of the intrinsic fungicidal properties of transgenic plants in order to achieve optimal protection of the seed and the germinating plant with a minimum expenditure of crop protection agents.

The present invention therefore also relates to a method for protecting seed and germinating plants against attack by animal pests and/or phytopathogenic harmful fungi by treating the seed with an inventive composition. The invention also relates to the use of the inventive compositions for treatment of seed for protection of the seed and the germinating plant against phytopathogenic fungi. The invention further relates to seed which has been treated with an inventive composition for protection from phytopathogenic fungi.

Animal pests and/or phytopathogenic harmful fungi which damage plants post-emergence are controlled primarily by the treatment of the soil and of the exposed parts of plants with crop protection agents. Owing to the concerns regarding a possible influence of the crop protection agents on the environment and the health of humans and animals, there are efforts to reduce the amount of active ingredients deployed.

One of the advantages of the present invention is that, because of the particular systemic properties of the inventive compositions, the treatment of the seed with these compositions not only protects the seed itself, but also the resulting plants after emergence, from animal pests and/or phytopathogenic harmful fungi. In this way, the immediate treatment of the crop at the time of sowing or shortly thereafter can be dispensed with.

It is likewise considered to be advantageous that the inventive active ingredients or compositions can be used especially also for transgenic seed, in which case the plant which grows from this seed is capable of expressing a protein which acts against pests. The treatment of such seed with the inventive active ingredients or compositions, merely through the expression of the protein, for example an insecticidal protein, can result in control of certain pests. Surprisingly, a further synergistic effect can be observed in this case, which additionally increases the effectiveness for protection against attack by pests.

The inventive compositions are suitable for protection of seed of any plant variety which is used in agriculture, in the greenhouse, in forests or in horticulture. More particularly, the seed is that of cereals (such as wheat, barley, rye, millet and oats), maize, cotton, soya, rice, potatoes, sunflower, bean, coffee, beet (e.g. sugar beet and fodder beet), peanut, vegetables (such as tomato, cucumber, onions and lettuce), lawns and ornamental plants. Of particular significance is the treatment of the seed of cereals (such as wheat, barley, rye and oats), maize and rice.

As also described below, the treatment of transgenic seed with the inventive active ingredients or compositions is of particular significance. This refers to the seed of plants containing at least one heterologous gene which allows the expression of a polypeptide or protein having insecticidal properties. The heterologous gene in transgenic seed may originate, for example, from microorganisms of the species *Bacillus, Rhizobium, Pseudomonas, Serratia, Trichoderma,*

*Clavibacter, Glomus* or *Gliocladium*. This heterologous gene preferably originates from *Bacillus* sp., in which case the gene product is effective against the European corn borer and/or the Western corn rootworm. The heterologous gene more preferably originates from *Bacillus thuringiensis*.

In the context of the present invention, the inventive composition is applied to the seed either alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, it generally has to be ensured that the amount of the inventive composition applied to the seed and/or the amount of further additives is selected such that the germination of the seed is not impaired, or that the resulting plant is not damaged. This must be ensured particularly in the case of active ingredients which can exhibit phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417, U.S. Pat. No. 4,245,432, U.S. Pat. No. 4,808,430, U.S. Pat. No. 5,876,739, US 2003/0176428, WO 2002/080675, WO 2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Usable with preference are alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate are usable with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel" [Chemistry of Crop Protection Agents and Pesticides], vol. 2, Springer Verlag, 1970, p. 401-412).

The seed dressing formulations usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, and beets, or else a wide variety of different vegetable seed. The seed dressing formulations usable in accordance with the invention, or the dilute preparations thereof, can also be used to dress seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying operation.

The application rate of the seed dressing formulations usable in accordance with the invention can be varied within a relatively wide range. It is guided by the particular content of the active ingredients in the formulations and by the seed. The application rates of active ingredient combination are generally between 0.001 and 50 g per kilogram of seed, preferably between 0.01 and 15 g per kilogram of seed.

In addition, the inventive compounds of the formula (I) also have very good antimycotic effects. They have a very broad antimycotic activity spectrum, especially against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The enumeration of these fungi by no means constitutes a restriction of the mycotic spectrum covered, and is merely of illustrative character.

The inventive active ingredients of the formula (I) can therefore be used both in medical and in non-medical applications.

The active ingredients can be used as such, in the form of their formulations or the use forms prepared therefrom, such as ready-to-use solutions, suspensions, wettable powders, pastes, soluble powders, dusts and granules. Application is accomplished in a customary manner, for example by watering, spraying, atomizing, broadcasting, dusting, foaming, spreading, etc. It is also possible to apply the active ingredients by the ultra-low volume method, or to inject the active ingredient preparation or the active ingredient itself into the soil. It is also possible to treat the seed of the plants.

When using the inventive active ingredients as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The inventive active ingredients are used in the veterinary sector and in animal husbandry in a known manner, by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active ingredient, such as collars, ear marks, tail marks, limb bands, halters, marking devices and the like.

When used for livestock, poultry, domestic animals and the like, the active ingredients of the formula (I) can be used as formulations (for example powders, emulsions, flowables) comprising the active ingredients in an amount of 1 to 80% by weight, either directly or after 100 to 10 000-fold dilution, or they may be used as a chemical bath.

The ready-to-use compositions may optionally also comprise other insecticides, and optionally also one or more fungicides.

With regard to possible additional mixing partners, reference is made to the abovementioned insecticides and fungicides.

At the same time, the inventive compounds can be used for protection of objects which come into contact with saltwater or brackish water, especially hulls, screens, nets, buildings, moorings and signalling systems, against fouling.

In addition, the inventive compounds can be used as anti-fouling compositions, alone or in combinations with other active ingredients.

The inventive treatment method can be used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using, for example, antisense technology, cosuppression technology or RNA interference— RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active ingredients and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active ingredient combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood to mean phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active ingredients.

Plants and plant cultivars which are preferably treated according to the invention include all plants which have genetic material which imparts particularly advantageous, useful traits to these plants (whether obtained by breeding and/or biotechnological means).

Plants and plant cultivars which are also preferably treated according to the invention are resistant against one or more biotic stresses, i.e. said plants show a better defence against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including, but not limited to, early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis or hybrid vigour which results in generally higher yield, vigour, health and resistance towards biotic and abiotic stresses. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling, i.e. the mechanical removal of the male reproductive organs (or male flowers) but, more typically, male sterility is the result of genetic determinants in the plant genome. In that case, and especially when seed is the desired product to be harvested from the hybrid plants it is typically useful to ensure that male fertility in the hybrid plants which contain the genetic determinants responsible for male sterility is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an eleusine EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally-occurring mutations of the above-mentioned genes.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally-occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that are made tolerant to acetolactate synthase (ALS) inhibitors. Known ALS inhibitors include, for example, sulphonylurea, imidazolinone, triazolopyrimidines, pyrimidinyloxy(thio)benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides.

The production of sulphonylurea-tolerant plants and imidazolinone-tolerant plants is described in international publication WO 1996/033270.

Further sulphonylurea- and imidazolinone-tolerant plants are also described, for example, in WO 2007/024782.

Other plants tolerant to imidazolinone and/or sulphonylurea can be obtained by induced mutagenesis, selection in cell cultures in the presence of the herbicide or mutation breeding.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins described online at: http://www.lifesci.sussex.ac.uk/Home/Neil_Crickmore/Bt/, or insecticidal portions thereof, e.g., proteins of the Cry protein classes Cry1Ab, Cry1Ac, Cry1F, Cry2Ab, Cry3Aa, or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR 604;
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, e.g., proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins.
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT 102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose) polymerase (PARP) gene in the plant cells or plants;
b. plants which contain a stress tolerance enhancing transgene capable of reducing the expression and/or the activity of the PARG encoding genes of the plants or plant cells;
c. plants which contain a stress tolerance enhancing transgene coding for a plant-functional enzyme of the nicotinamide adenine dinucleotide salvage biosynthesis pathway including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications.
2) transgenic plants which synthesize non-starch carbohydrate polymers or which synthesize non-starch carbohydrate polymers with altered properties in comparison to wild type plants without genetic modification. Examples are plants producing polyfructose, especially of the inulin and levan type, plants producing alpha-1,4-glucans, plants producing alpha-1,6 branched alpha-1,4-glucans, plants producing alteman.
3) transgenic plants which produce hyaluronan.

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, containing an altered form of cellulose synthase genes;
b) plants, such as cotton plants, containing an altered form of rsw2 or rsw3 homologous nucleic acids;
c) plants, such as cotton plants, with increased expression of sucrose phosphate synthase;
d) plants, such as cotton plants, with increased expression of sucrose synthase;
e) plants, such as cotton plants, wherein the timing of the plasmodesmatal gating at the basis of the fibre cell is altered, e.g. through downregulation of fibre-selective β-1,3-glucanase;
f) plants, such as cotton plants, having fibres with altered reactivity, e.g. through the expression of N-acetylglucosaminetransferase gene including nodC and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics and include:
a) plants, such as oilseed rape plants, producing oil having a high oleic acid content;
b) plants, such as oilseed rape plants, which produce oil having a low linolenic acid content;
c) plants, such as oilseed rape plants, producing oil having a low level of saturated fatty acids.

Particularly useful transgenic plants which may be treated according to the invention are plants which comprise one or more genes which encode one or more toxins, and are the transgenic plants which are sold under the following trade names: YIELD GARD® (for example maize, cotton, soy beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potatoes). Examples of herbicide-tolerant plants which should be mentioned are corn varieties, cotton varieties and soybean varieties which are available under the following trade names: Roundup Ready® (glyphosate tolerance, for example maize, cotton, soya bean), Liberty Link® (phosphinothricin tolerance, for example oilseed rape), IMI® (imidazolinone tolerance) and SCS® (sulphonylurea tolerance), for example maize. Herbicide-resistant plants (plants bred in a conventional manner for herbicide tolerance) which should be mentioned include the varieties sold under the Clearfield® name (for example maize).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

The plants listed can be treated in accordance with the invention in a particularly advantageous manner with the compounds of the general formula (I) and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

The inventive active ingredients or compositions can thus be used to protect plants from attack by the pathogens mentioned for a certain period of time after treatment. The period for which protection is provided extends generally for 1 to 28 days, preferably for 1 to 14 days, particularly preferably for 1 to 10 days, very particularly preferably for 1 to 7 days after the treatment of the plants with the active ingredients, or for up to 200 days after a seed treatment.

The preparation and the use of the inventive active ingredients of the formula (I) is illustrated by the examples which follow. However, the invention is not limited to these examples.

General Notes:

Unless stated otherwise, all chromatographic purification and separation steps are carried out on silica gel and using a solvent gradient from 0:100 ethyl acetate/cyclohexane to 100:0 ethyl acetate/cyclohexane.

Preparation of Compound (I-5)

Step 1 tert-Butyl 4-[4-(5-{2-[(methylsulphonyl)amino]phenyl}-4,5-dihydro-1,2-oxazol-3-yl)-1,3-thiazol-2-yl]piperidine-1-carboxylate (XVIIf-1)

To a solution of tert-butyl 4-{4-[(Z/E)-(hydroxyimino)methyl]-1,3-thiazol-2-yl}piperidine-1-carboxylate (1.35 g) and N-(2-vinylphenyl)methanesulphonamide (1.11 g) in ethyl acetate (20 ml) were added, at room temperature, potassium hydrogencarbonate (2.17 g) and N-chlorosuccinimide (0.58 g) and then three drops of water. The reaction mixture was stirred at 50° C. overnight, then ethyl acetate and water were added, and the mixture was extracted with ethyl acetate. The organic extracts were dried over sodium sulphate and concentrated under reduced pressure. The residue was purified by chromatography. This gave tert-butyl 4-[4-(5-{2-[(methylsulphonyl)amino]phenyl}-4,5-dihydro-1,2-oxazol-3-yl)-1,3-thiazol-2-yl]piperidine-1-carboxylate (0.94 g).

Step 2

4-[4-(5-{2-[(Methylsulphonyl)ammonio]phenyl}-4,5-dihydro-1,2-oxazol-3-yl)-1,3-thiazol-2-yl]piperidinium dichloride (XIIIb-1)

To a solution of tert-butyl 4-[4-(5-{2-[(methylsulphonyl)amino]phenyl}-4,5-dihydro-1,2-oxazol-3-yl)-1,3-thiazol-2-yl]piperidine-1-carboxylate (900 mg) in 1,4-dioxane (10 ml) was added dropwise, at 0° C., a 4 molar solution of hydrogen chloride in 1,4-dioxane (6.66 ml). The reaction mixture was stirred at 0° C. and then gradually warmed to room temperature. After stirring overnight, the solvent and excess hydrogen chloride were removed. This gave 4-[4-(5-{2-[(methylsulphonyl)ammonio]phenyl}-4,5-dihydro-1,2-oxazol-3-yl)-1,3-thiazol-2-yl]piperidinium dichloride (1.00 g).

Step 3

N-(2-{3-[2-(1-{[5-Methyl-3-(trifluoromethyl)-1H-pyrazol-1-yl]acetyl}piperidin-4-yl)-1,3-thiazol-4-yl]-4,5-dihydro-1,2-oxazol-5-yl}phenyl)methanesulphonamide (I-5)

4-[4-(5-{2-[(Methylsulphonyl)ammonio]phenyl}-4,5-dihydro-1,2-oxazol-3-yl)-1,3-thiazol-2-yl]piperidinium dichloride (201 mg), [5-methyl-3-(trifluoromethyl)-1H-pyrazol-1-yl]acetic acid (104 mg) and triethylamine (51 mg) are dissolved in dichloromethane (10 ml) and the mixture is stirred for 10 min. The mixture is stirred for a further 10 min, before bromotris(pyrrolidino)phosphonium hexafluorophosphate (254 mg) is added. The reaction mixture is stirred at room temperature for 2 hours. After removal of the solvent under reduced pressure, the residue is purified by chromatography. This gives N-(2-{3-[2-(1-{[5-methyl-3-(trifluoromethyl)-1H-pyrazol-1-yl]acetyl}piperidin-4-yl)-1,3-thiazol-4-yl]-4,5-dihydro-1,2-oxazol-5-yl}phenyl)methanesulphonamide (107 mg).

Preparation of Compound (I-4)

Step 1

N-(2-{3-[2-(1-{[2,5-Bis(difluoromethyl)phenyl]acetyl}piperidin-4-yl)-1,3-thiazol-4-yl]-4,5-dihydro-1,2-oxazol-5-yl}phenyl)methanesulphonamide (I-4)

4-[4-(5-{2-[(Methylsulphonyl)ammonio]phenyl}-4,5-dihydro-1,2-oxazol-3-yl)-1,3-thiazol-2-yl]piperidinium dichloride (298 mg) and [2,5-bis(difluoromethyl)phenyl]acetic acid (175 mg) were converted analogously to I-5 (step 3). This gave N-(2-{3-[2-(1-{[2,5-bis(difluoromethyl)phenyl]acetyl}piperidin-4-yl)-1,3-thiazol-4-yl]-4,5-dihydro-1,2-oxazol-5-yl}phenyl)methanesulphonamide (170 mg).

Preparation of Compound (I-6)

Step 1

N-[2,5-Bis(difluoromethyl)phenyl]-4-[4-(5-{2-[(methylsulphonyl)amino]phenyl}-4,5-dihydro-1,2-oxazol-3-yl)-1,3-thiazol-2-yl]piperidine-1-carboxamide (I-6)

To a suspension of 4-[4-(5-{2-[(methylsulphonyl)ammonio]phenyl}-4,5-dihydro-1,2-oxazol-3-yl)-1,3-thiazol-2-yl]piperidinium dichloride (202 mg) in dichloromethane (5 ml) and triethylamine (51 mg) at room temperature were added 1,4-bis(difluoromethyl)-2-isocyanatobenzene (100 mg) and one drop of 1,8-diazabicyclo[5.4.0]undec-7-ene (DBU). The mixture was stirred at room temperature for 2 hours, and then saturated ammonium chloride solution was added. The aqueous phase was removed and extracted with ethyl acetate. The combined organic phases were dried over sodium sulphate and concentrated under reduced pressure. The residue was purified by chromatography. This gave N-[2,5-bis(difluoromethyl)phenyl]-4-[4-(5-{2-[(methylsulphonyl)amino]phenyl}-4,5-dihydro-1,2-oxazol-3-yl)-1,3-thiazol-2-yl]piperidine-1-carboxamide (150 mg).

Preparation of Compounds of the Formula (I-3)

Step 1 tert-Butyl 4-{4-[5-(2-formylphenyl)-4,5-dihydro-1,2-oxazol-3-yl]-1,3-thiazol-2-yl}piperidine-1-carboxylate (XVIIf-2)

To a solution of tert-butyl 4-{4-[(Z/E)-(hydroxyimino)methyl]-1,3-thiazol-2-yl}piperidine-1-carboxylate (5.6 g) and 2-vinylbenzaldehyde (2.61 g) in ethyl acetate (70 ml) at room temperature were added potassium hydrogencarbonate (7.23 g) and N-chlorosuccinimide (2.31 g), and then three drops of water. The reaction mixture was stirred at 60° C. for 3 hours, then ethyl acetate and water were added, and the mixture was extracted with ethyl acetate. The organic extracts were dried over sodium sulphate and concentrated under reduced pressure. The residue was purified by chromatography. The developed product is tert-Butyl 4-{4-[5-(2-formylphenyl)-4,5-dihydro-1,2-oxazol-3-yl]-1,3-thiazol-2-yl}piperidine-1-carboxylate (5.69 g).

Step 2

4-{4-[5-(2-Formylphenyl)-4,5-dihydro-1,2-oxazol-3-yl]-1,3-thiazol-2-yl}piperidinium chloride (XIIIb-2)

tert-Butyl 4-{4-[5-(2-formylphenyl)-4,5-dihydro-1,2-oxazol-3-yl]-1,3-thiazol-2-yl}piperidine-1-carboxylate (5.1 g) was converted analogously to I-5 (step 2). This gave 4-{4-[5-(2-formylphenyl)-4,5-dihydro-1,2-oxazol-3-yl]-1,3-thiazol-2-yl}piperidinium chloride (4.35 g).

Step 3

N-(5-Chloro-2-methylphenyl)-4-{4-[5-(2-formylphenyl)-4,5-dihydro-1,2-oxazol-3-yl]-1,3-thiazol-2-yl}piperidine-1-carboxamide (I-3)

To a suspension of 4-{4-[5-(2-formylphenyl)-4,5-dihydro-1,2-oxazol-3-yl]-1,3-thiazol-2-yl}piperidinium chloride (1.44 g) in dichloromethane (30 ml) and diisopropylethylamine (0.73 ml) at room temperature were added 4-chloro-2-isocyanato-1-methylbenzene (700 mg) and one drop of 1,8-diazabicyclo[5.4.0]undec-7-ene (DBU). The mixture was stirred at room temperature overnight, and water was then added. The aqueous phase was removed and extracted with ethyl acetate. The combined organic phases were dried over sodium sulphate and concentrated under reduced pressure. The residue was purified by chromatography. This gave N-(5-chloro-2-methylphenyl)-4-{4-[5-(2-formylphenyl)-4,5-dihydro-1,2-oxazol-3-yl]-1,3-thiazol-2-yl}piperidine-1-carboxamide (1.23 g).

Preparation of Compound (I-7)

2-{3-[2-(1-{[5-Methyl-3-(trifluoromethyl)-1H-pyrazol-1-yl]acetyl}piperidin-4-yl)-1,3-thiazol-4-yl]-4,5-dihydro-1,2-oxazol-5-yl}benzaldehyde (I-7)

To a solution of [5-methyl-3-(trifluoromethyl)-1H-pyrazol-1-yl]acetic acid (900 mg) in dichloromethane (20 ml) are added, at 0° C., oxalyl chloride (1.50 g) and one drop of N,N-dimethylformamide. The reaction mixture is stirred at room temperature for 2 hours. The solvent and the excess reagent are removed under reduced pressure. The solid residue is dissolved again in dichloromethane and added dropwise at 0° C. to a solution of 4-{4-[5-(2-formylphenyl)-4,5-dihydro-1,2-oxazol-3-yl]-1,3-thiazol-2-yl}piperidinium chloride (1.49 g) and diisopropylethylamine (2.05 ml) in dichloromethane (20 ml). The reaction mixture is stirred at room temperature overnight. Then concentrated sodium hydrogencarbonate solution is added thereto, and the aqueous phase is removed and extracted with ethyl acetate. The combined organic phases are dried over sodium sulphate and concentrated. Purification by column chromatography gives 2-{3-[2-(1-{[5-methyl-3-(trifluoromethyl)-1H-pyrazol-1-yl]acetyl}piperidin-4-yl)-1,3-thiazol-4-yl]-4,5-dihydro-1,2-oxazol-5-yl}benzaldehyde (2.00 g).

EXAMPLES

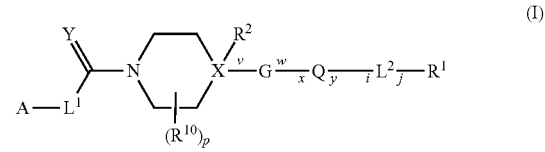

(I)

The structural elements $G^1$ and $Q^{24}$-3 listed in Table 1 are defined as follows:

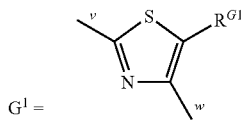

$G^1 =$

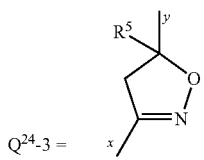

$Q^{24}$-3 =

For all compounds listed in Table 1, p=0 and $L^2$=direct bond, $R^2$=H

TABLE 1

| Ex. | A | L1 | Y | X | G | $R^{G1}$ | Q | $R^5$ | $R^1$ | Log P |
|---|---|---|---|---|---|---|---|---|---|---|
| 1 | 5-methyl-3-(trifluoromethyl)-1H-pyrazol-1-yl | $CH_2$ | O | C | $G^1$ | H | $Q^{24}$-3 | H | 3-formylphenyl | 2.83[a] |
| 2 | 5-chloro-2-methylphenyl | NH | O | C | $G^1$ | H | $Q^{24}$-3 | H | 3-formylphenyl | 3.05[a] |
| 3 | 5-chloro-2-methylphenyl | NH | O | C | $G^1$ | H | $Q^{24}$-3 | H | 2-formylphenyl | 3.35[a] |
| 4 | 2,5-bis(difluoromethyl)phenyl | $CH_2$ | O | C | $G^1$ | H | $Q^{24}$-3 | H | 2-[(methylsulphonyl)amino]phenyl | 2.81[a] |
| 5 | 5-methyl-3-(trifluoromethyl)-1H-pyrazol-1-yl | $CH_2$ | O | C | $G^1$ | H | $Q^{24}$-3 | H | 2-[(methylsulphonyl)amino]phenyl | |
| 6 | 2,5-bis(difluoromethyl)phenyl | NH | O | C | $G^1$ | H | $Q^{24}$-3 | H | 2-[(methylsulphonyl)amino]phenyl | 2.72[a] |
| 7 | 5-methyl-3-(trifluoromethyl)-1H-pyrazol-1-yl | $CH_2$ | O | C | $G^1$ | H | $Q^{24}$-3 | H | 2-formylphenyl | 3.12[a] |
| 8 | 5-methyl-3-(trifluoromethyl)-1H-pyrazol-1-yl | $CH_2$ | O | C | $G^1$ | H | $Q^{24}$-3 | H | 2,6-difluoro-3-(prop-2-yn-1-yloxy)phenyl | |
| 9 | 5-methyl-3-(trifluoromethyl)-1H-pyrazol-1-yl | $CH_2$ | O | C | $G^1$ | H | $Q^{24}$-3 | H | 3-fluoro-2-(prop-2-yn-1-yloxy)phenyl | |
| 10 | 5-methyl-3-(trifluoromethyl)-1H-pyrazol-1-yl | $CH_2$ | O | C | $G^1$ | H | $Q^{24}$-3 | H | 3-(prop-2-yn-1-yloxy)phenyl | 3.49[a]; 3.3[b] |
| 11 | 5-methyl-3-(trifluoromethyl)-1H-pyrazol-1-yl | $CH_2$ | O | C | $G^1$ | H | $Q^{24}$-3 | H | 2-chloro-6-(prop-2-yn-1-yloxy)phenyl | 3.62[a]; 3.53[b] |
| 12 | 5-methyl-3-(trifluoromethyl)-1H-pyrazol-1-yl | $CH_2$ | O | C | $G^1$ | H | $Q^{24}$-3 | H | 2-fluoro-6-(prop-2-yn-1-yloxy)phenyl | 3.35[a]; 3.27[b] |
| 13 | 5-methyl-3-(trifluoromethyl)-1H-pyrazol-1-yl | $CH_2$ | O | C | $G^1$ | H | $Q^{24}$-3 | H | 2-(prop-2-yn-1-yloxy)phenyl | 3.47[a]; 3.37[b] |
| 14 | 3,5-bis(trifluoromethyl)-1H-pyrazol-1-yl | $CH_2$ | O | C | $G^1$ | H | $Q^{24}$-3 | H | 2-[(cyclopropylcarbonyl)oxy]phenyl | 4.04[a] |
| 15 | 3-(difluoromethyl)-5-methyl-1H-pyrazol-1-yl | $CH_2$ | O | C | $G^1$ | H | $Q^{24}$-3 | H | 2-(but-2-yn-1-yloxy)-4-methoxyphenyl | 3.28[a] |
| 16 | 3,5-bis(trifluoromethyl)-1H-pyrazol-1-yl | $CH_2$ | O | C | $G^1$ | H | $Q^{24}$-3 | H | 2-(cyclopropylmethoxy)phenyl | 4.59[a] |
| 17 | 5-methyl-3-(trifluoromethyl)-1H-pyrazol-1-yl | $CH_2$ | O | C | $G^1$ | H | $Q^{24}$-3 | H | 2-(cyclopropylmethoxy)phenyl | 4.03[a] |
| 18 | 5-(difluoromethyl)-3-methyl-1H-pyrazol-1-yl | $CH_2$ | O | C | $G^1$ | H | $Q^{24}$-3 | H | 2-(allyloxy)phenyl | 3.42[a]; 3.33[b] |
| 19 | 5-methyl-3-(trifluoromethyl)-1H-pyrazol-1-yl | $CH_2$ | O | C | $G^1$ | H | $Q^{24}$-3 | H | 3-(allyloxy)-2,6-difluorophenyl | |
| 20 | 3-(difluoromethyl)-5-methyl-1H-pyrazol-1-yl | $CH_2$ | O | C | $G^1$ | H | $Q^{24}$-3 | H | 4-chloro-2-(prop-2-yn-1-yloxy)phenyl | 3.37[a]; 3.36[b] |
| 21 | 3-(difluoromethyl)-5-methyl-1H-pyrazol-1-yl | $CH_2$ | O | C | $G^1$ | H | $Q^{24}$-3 | H | 2,4-dichloro-6-(prop-2-yn-1-yloxy)phenyl | 3.66[a]; 3.57[b] |
| 22 | 3-(difluoromethyl)-5-methyl-1H-pyrazol-1-yl | $CH_2$ | O | C | $G^1$ | H | $Q^{24}$-3 | H | 2-(allyloxy)-4-methylphenyl | 3.62[a]; 3.66[b]; |
| 23 | 3-(difluoromethyl)-5-methyl-1H-pyrazol-1-yl | $CH_2$ | O | C | $G^1$ | H | $Q^{24}$-3 | H | 4-methyl-2-(prop-2-yn-1-yloxy)phenyl | 3.23[a]; 3.23[b] |
| 24 | 3-(difluoromethyl)-5-methyl-1H-pyrazol-1-yl | $CH_2$ | O | C | $G^1$ | H | $Q^{24}$-3 | H | 2-(allyloxy)-4,6-dichlorophenyl | 3.95[a]; 3.97[b]; |
| 25 | 2,5-dimethylphenyl | NH | O | C | $G^1$ | H | $Q^{24}$-3 | H | 2-(allyloxy)-6-fluorophenyl | 3.64[a]; 3.62[b] |
| 26 | 5-methyl-3-(trifluoromethyl)-1H-pyrazol-1-yl | $CH_2$ | O | C | $G^1$ | H | $Q^{24}$-3 | H | 4-methyl-2-(prop-2-yn-1-yloxy)phenyl | 3.67[a]; 3.61[b] |

TABLE 1-continued

| Ex. | A | L1 | Y | X | G | R^G1 | Q | R^5 | R^1 | Log P |
|---|---|---|---|---|---|---|---|---|---|---|
| 27 | 3-(difluoromethyl)-5-methyl-1H-pyrazol-1-yl | CH$_2$ | O | C | G$^1$ | H | Q$^{24}$-3 | H | 2-(cyclopropylmethoxy)-4-methoxyphenyl | 3.5[a] |
| 28 | 3-(difluoromethyl)-5-methyl-1H-pyrazol-1-yl | CH$_2$ | O | C | G$^1$ | H | Q$^{24}$-3 | H | 2-(cyclopropylmethoxy)-6-fluorophenyl | 3.44[a] |
| 29 | 5-(difluoromethyl)-3-methyl-1H-pyrazol-1-yl | CH$_2$ | O | C | G$^1$ | H | Q$^{24}$-3 | H | 2-(prop-2-yn-1-yloxy)phenyl | 3.03[a] |
| 30 | 5-methyl-3-(trifluoromethyl)-1H-pyrazol-1-yl | CH$_2$ | O | C | G$^1$ | H | Q$^{24}$-3 | H | 2-(allyloxy)phenyl | 3.86[a]; 3.73[b] |
| 31 | 3-(difluoromethyl)-5-methyl-1H-pyrazol-1-yl | CH$_2$ | O | C | G$^1$ | H | Q$^{24}$-3 | H | 2-fluoro-6-(prop-2-yn-1-yloxy)phenyl | 2.92[a] |
| 32 | 3,5-bis(trifluoromethyl)-1H-pyrazol-1-yl | CH$_2$ | O | C | G$^1$ | H | Q$^{24}$-3 | H | 2-(prop-2-yn-1-yloxy)phenyl | 3.91[a] |
| 33 | 3,5-bis(trifluoromethyl)-1H-pyrazol-1-yl | CH$_2$ | O | C | G$^1$ | H | Q$^{24}$-3 | H | 2-(allyloxy)phenyl | 4.38[a] |
| 34 | 5-methyl-3-(trifluoromethyl)-1H-pyrazol-1-yl | CH$_2$ | O | C | G$^1$ | H | Q$^{24}$-3 | H | 2-[(methylsulphonyl)methyl]phenyl | 2.6[a] |
| 35 | 5-methyl-3-(trifluoromethyl)-1H-pyrazol-1-yl | CH$_2$ | O | C | G$^1$ | H | Q$^{24}$-3 | H | 2-[(methylsulphinyl)methyl]phenyl | 2.34[a] |
| 36 | 5-methyl-3-(trifluoromethyl)-1H-pyrazol-1-yl | CH$_2$ | O | C | G$^1$ | H | Q$^{24}$-3 | H | 2-[(ethylsulphinyl)methyl]phenyl | 2.53[a] |
| 37 | 5-(difluoromethyl)-3-methyl-1H-pyrazol-1-yl | CH$_2$ | O | C | G$^1$ | H | Q$^{24}$-3 | CH$_3$ | 2-fluoro-6-(prop-2-yn-1-yloxy)phenyl | 3.11[a]; 3.12[b]; |
| 38 | 2,5-dimethylphenyl | NH | O | C | G$^1$ | H | Q$^{24}$-3 | H | 2-chloro-6-(prop-2-yn-1-yloxy)phenyl | 3.68[a]; 3.57[b] |
| 39 | 5-chloro-2-methylphenyl | NH | O | C | G$^1$ | H | Q$^{24}$-3 | H | 2-(allyloxy)-6-chlorophenyl | 4.21[a]; 4.11[b] |
| 40 | 5-methyl-3-(trifluoromethyl)-1H-pyrazol-1-yl | CH$_2$ | O | C | G$^1$ | H | Q$^{24}$-3 | H | 3-[(cyclopropylcarbonyl)oxy]phenyl | 3.53[a]; 3.47[b] |
| 41 | 5-methyl-3-(trifluoromethyl)-1H-pyrazol-1-yl | CH$_2$ | O | C | G$^1$ | H | Q$^{24}$-3 | H | 3-(allyloxy)phenyl | 3.62[a]; 3.68[b]; |
| 42 | 2,5-dimethylphenyl | NH | O | C | G$^1$ | H | Q$^{24}$-3 | H | 2-(allyloxy)-6-chlorophenyl | 3.98[a]; 3.91[b] |
| 43 | 5-methyl-3-(trifluoromethyl)-1H-pyrazol-1-yl | CH$_2$ | O | C | G$^1$ | H | Q$^{24}$-3 | H | 2-[(2,2,2-trifluoroethoxy)methyl]phenyl | 3.77[a] |
| 44 | 5-methyl-3-(trifluoromethyl)-1H-pyrazol-1-yl | CH$_2$ | O | C | G$^1$ | H | Q$^{24}$-3 | H | 2-[(2-methoxyethoxy)methyl]phenyl | 3.28[a] |
| 45 | 2,5-dimethylphenyl | NH | O | C | G$^1$ | H | Q$^{24}$-3 | H | 2-(prop-2-yn-1-yloxy)phenyl | 3.43[a]; 3.41[b] |
| 46 | 2,5-dimethylphenyl | NH | O | C | G$^1$ | H | Q$^{24}$-3 | H | 2-(allyloxy)phenyl | 3.91[a]; 3.81[b] |
| 47 | 5-methyl-3-(trifluoromethyl)-1H-pyrazol-1-yl | CH$_2$ | O | C | G$^1$ | H | Q$^{24}$-3 | H | 4-[(cyclopropylcarbonyl)oxy]phenyl | 3.49[a]; 3.4[b] |
| 48 | 5-methyl-3-(trifluoromethyl)-1H-pyrazol-1-yl | CH$_2$ | O | C | G$^1$ | H | Q$^{24}$-3 | H | 2-chloro-6-[(cyclopropylcarbonyl)oxy]phenyl | 3.73[a]; 3.64[b] |
| 49 | 5-methyl-3-(trifluoromethyl)-1H-pyrazol-1-yl | CH$_2$ | O | C | G$^1$ | H | Q$^{24}$-3 | H | 2-fluoro-6-(2-methoxyethoxy)phenyl | 3.28[a]; 3.17[b] |
| 50 | 5-methyl-3-(trifluoromethyl)-1H-pyrazol-1-yl | CH$_2$ | O | C | G$^1$ | H | Q$^{24}$-3 | H | 2-(allyloxy)-6-chlorophenyl | 3.94[a]; 3.83[b] |
| 51 | 5-methyl-3-(trifluoromethyl)-1H-pyrazol-1-yl | CH$_2$ | O | C | G$^1$ | H | Q$^{24}$-3 | H | 2-(allyloxy)-6-fluorophenyl | 3.7[a]; 3.61[b] |
| 52 | 5-methyl-3-(trifluoromethyl)-1H-pyrazol-1-yl | CH$_2$ | O | C | G$^1$ | H | Q$^{24}$-3 | H | 2-(allyloxy)-3-fluorophenyl | 3.97[a]; 3.84[b] |
| 53 | 5-methyl-3-(trifluoromethyl)-1H-pyrazol-1-yl | CH$_2$ | O | C | G$^1$ | H | Q$^{24}$-3 | H | 2-fluoro-6-formylphenyl | 3.03[a]; 2.95[b] |
| 54 | 5-methyl-3-(trifluoromethyl)-1H-pyrazol-1-yl | CH$_2$ | O | C | G$^1$ | H | Q$^{24}$-3 | H | 2-[(cyclopropylcarbonyl)oxy]-3-fluorophenyl | 3.62[a]; 3.5[b] |
| 55 | 5-methyl-3-(trifluoromethyl)-1H-pyrazol-1-yl | CH$_2$ | O | C | G$^1$ | H | Q$^{24}$-3 | H | 2-(2-methoxyethoxy)phenyl | 3.37[a]; 3.25[b] |

TABLE 1-continued

| Ex. A | | L1 | Y | X | G | R$^{G1}$ | Q | R$^5$ | R$^1$ | Log P |
|---|---|---|---|---|---|---|---|---|---|---|
| 56 | 5-methyl-3-(trifluoromethyl)-1H-pyrazol-1-yl | CH$_2$ | O | C | G$^1$ | H | Q$^{24}$-3 | H | 2-[(cyclopropylcarbonyl)oxy]phenyl | 3.52[a]; 3.41[b] |

The logP values were measured according to EEC directive 79/831 Annex V.A8 by HPLC (High Performance Liquid Chromatography) on reversed-phase columns (C 18), using the methods below:
[a] The LC-MS determination in the acidic range is effected at pH 2.7 with 0.1% aqueous formic acid and acetonitrile (contains 0.1% formic acid) as eluents; linear gradient from 10% acetonitrile to 95% acetonitrile.
[b] The LC-MS determination in the neutral range is effected at pH 7.8 using 0.001 molar aqueous ammonium hydrogencarbonate solution and acetonitrile as eluents; linear gradient from 10% acetonitrile to 95% acetonitrile.

The calibration is effected with unbranched alkan-2-ones (having 3 to 16 carbon atoms) with known log P values (log P values determined on the basis of the retention times by linear interpolation between two successive alkanones).

The lambda-max values were determined in the maxima of the chromatographic signals using the UV spectra from 200 nm to 400 nm.

NMR Data of Selected Examples

NMR Peak List Method

The 1H NMR data of selected examples are stated in the form of 1H NMR peak lists. For each signal peak, first the δ value in ppm and then the signal intensity in round brackets are listed. The δ value—signal intensity number pairs for different signal peaks are listed with separation from one another by semicolons.

The peak list for one example therefore takes the form of:
δ$_1$ (intensity$_1$); δ$_2$ (intensity$_2$); . . . ; δ$_i$ (intensity$_i$); . . . ; δ$_n$ (intensity$_n$)

Ex. 1, Solvent: DMSO, Spectrometer: 399.95 MHz 10.0344 (6.63); 8.0579 (0.79); 8.0400 (6.68); 7.9295 (3.74); 7.8988 (2.27); 7.8831 (2.00); 7.8801 (2.32); 7.7478 (1.88); 7.7285 (2.24); 7.6635 (2.24); 7.6446 (2.92); 7.6255 (1.19); 6.4922 (4.46); 5.8980 (1.40); 5.8784 (1.71); 5.8708 (1.52); 5.8515 (1.21); 5.3605 (0.36); 5.3405 (0.97); 5.2983 (2.90); 5.2496 (2.81); 5.2072 (0.87); 4.3847 (1.15); 4.3527 (1.13); 4.0571 (0.96); 4.0393 (2.31); 4.0216 (2.35); 4.0036 (1.55); 3.9837 (2.26); 3.9560 (2.66); 3.9405 (1.98); 3.9130 (1.45); 3.4474 (1.79); 3.4278 (2.00); 3.4041 (2.39); 3.3845 (3.03); 3.3262 (49.36); 3.3125 (313.38); 3.2424 (1.57); 2.8718 (0.91); 2.8449 (1.44); 2.8143 (0.81); 2.6743 (0.45); 2.6701 (0.49); 2.5053 (62.03); 2.5010 (65.38); 2.3326 (0.53); 2.3277 (0.56); 2.2097 (16.00); 2.1319 (1.48); 2.1068 (2.42); 2.0766 (1.41); 2.0049 (1.06); 2.0012 (1.21); 1.9971 (1.55); 1.9870 (8.57); 1.8437 (0.61); 1.8238 (1.08); 1.7936 (0.95); 1.7640 (0.44); 1.6093 (0.63); 1.5889 (1.03); 1.5799 (1.02); 1.5581 (0.98); 1.5287 (0.44); 1.1930 (2.83); 1.1854 (0.97); 1.1752 (4.77); 1.1574 (2.31); −0.0002 (1.06);

Ex. 2, Solvent: DMSO, Spectrometer: 399.95 MHz 10.0350 (7.37); 9.9023 (0.41); 8.6412 (0.39); 8.1288 (3.28); 8.0347 (7.77); 7.9318 (3.17); 7.9024 (1.25); 7.8992 (1.80); 7.8956 (1.04); 7.8836 (1.44); 7.8803 (2.04); 7.8768 (1.27); 7.7490 (1.35); 7.7328 (1.52); 7.7297 (1.99); 7.6636 (1.95); 7.6446 (2.84); 7.6256 (1.17); 7.3336 (3.23); 7.3281 (3.30); 7.1991 (2.18); 7.1786 (2.94); 7.0833 (2.27); 7.0777 (2.14); 7.0630 (1.58); 7.0574 (1.50); 5.8976 (1.13); 5.8781 (1.35); 5.8703 (1.29); 5.8507 (1.16); 4.1731 (1.81); 4.1396 (1.90); 4.0578 (1.32); 4.0400 (3.70); 4.0222 (3.72); 4.0044 (1.30); 3.9854 (1.31); 3.9578 (1.48); 3.9421 (1.68); 3.9147 (1.44); 3.4505 (1.74); 3.4309 (1.76); 3.4073 (1.67); 3.3878 (1.85); 3.3567 (1.71); 3.3193 (212.77); 3.0448 (1.07); 3.0392 (1.19); 3.0104 (2.19); 2.9815 (1.25); 2.5411 (0.60); 2.5108 (12.77); 2.5065 (22.65); 2.5021 (28.64); 2.4977 (19.62); 2.4934 (9.27); 2.1877 (0.40); 2.1557 (15.50); 2.0936 (1.51); 2.0679 (1.65); 1.9877 (16.00); 1.7197 (0.52); 1.7101 (0.66); 1.6880 (1.28); 1.6799 (1.42); 1.6579 (1.27); 1.6495 (1.19); 1.6282 (0.48); 1.6190 (0.39); 1.1935 (4.47); 1.1757 (8.72); 1.1579 (4.30); −0.0002 (0.43);

Ex. 3, Solvent: DMSO, Spectrometer: 399.95 MHz 10.1834 (6.76); 8.1195 (3.33); 8.0328 (1.90); 8.0289 (1.95); 8.0231 (0.70); 8.0126 (2.50); 8.0099 (2.53); 8.0020 (8.12); 7.7367 (0.79); 7.7335 (0.83); 7.7178 (2.01); 7.6990 (1.52); 7.6957 (1.42); 7.6241 (1.99); 7.6159 (2.62); 7.6074 (2.57); 7.5974 (1.90); 7.5894 (1.20); 7.3298 (3.23); 7.3243 (3.27); 7.1963 (2.20); 7.1758 (2.98); 7.0813 (2.24); 7.0758 (2.11); 7.0610 (1.60); 7.0554 (1.51); 6.4452 (1.19); 6.4290 (1.35); 6.4174 (1.33); 6.4011 (1.21); 4.1613 (1.78); 4.1278 (1.89); 4.0899 (1.41); 4.0620 (1.65); 4.0462 (1.79); 4.0401 (1.35); 4.0222 (1.56); 4.0185 (1.60); 4.0045 (0.46); 3.3155 (190.78); 3.2923 (3.19); 3.2755 (1.02); 3.2660 (0.58); 3.2268 (1.72); 3.2106 (1.68); 3.1831 (1.57); 3.1669 (1.55); 3.0251 (1.23); 2.9958 (2.25); 2.9668 (1.27); 2.5107 (11.92); 2.5065 (21.69); 2.5020 (27.90); 2.4977 (19.76); 2.4935 (9.77); 2.1503 (16.00); 2.0743 (1.51); 2.0485 (1.71); 1.9879 (4.94); 1.6994 (0.51); 1.6904 (0.61); 1.6686 (1.31); 1.6612 (1.39); 1.6386 (1.30); 1.6311 (1.21); 1.6090 (0.50); 1.5996 (0.40); 1.1935 (1.36); 1.1758 (2.65); 1.1580 (1.31); −0.0002 (2.28);

Ex. 4, Solvent: DMSO, Spectrometer: 399.95 MHz 9.2859 (0.81); 8.0295 (0.39); 8.0173 (6.58); 7.7187 (1.27); 7.6986 (1.91); 7.6011 (1.48); 7.5812 (1.08); 7.5052 (2.29); 7.4373 (1.17); 7.4208 (1.52); 7.4168 (1.40); 7.4057 (0.47); 7.3939 (0.45); 7.3784 (1.58); 7.3680 (2.66); 7.3618 (4.78); 7.3593 (4.89); 7.3491 (1.42); 7.3429 (1.39); 7.3367 (1.18); 7.3266 (0.51); 7.3204 (0.50); 7.2856 (1.04); 7.2187 (1.17); 7.1489 (2.16); 7.0796 (2.37); 7.0128 (1.09); 6.9403 (1.18); 6.1207 (0.97); 6.0995 (1.21); 6.0927 (1.20); 6.0723 (1.00); 5.7464 (4.98); 4.4407 (0.61); 4.4116 (0.63); 4.0778 (0.63); 4.0485 (0.87); 4.0392 (0.98); 4.0115 (2.08); 3.9904 (1.99); 3.9505 (1.30); 3.9228 (1.16); 3.9068 (1.34); 3.8789 (1.04); 3.3752 (1.57); 3.3642 (2.39); 3.3080 (1524.29); 3.2856 (11.89); 3.2635 (3.70); 3.2426 (2.20); 3.2286 (1.24); 3.2084 (0.77); 3.1559 (0.42); 3.1400 (0.52); 3.0603 (1.03); 3.0358 (16.00); 2.9393 (0.46); 2.8903 (1.36); 2.8331 (0.56); 2.7997 (0.92); 2.7683 (0.57); 2.7316 (1.19); 2.6739

(1.32); 2.6692 (1.64); 2.6647 (1.30); 2.5392 (2.28); 2.5221 (7.36); 2.5090 (93.05); 2.5046 (173.22); 2.5002 (226.03); 2.4958 (157.39); 2.4914 (75.79); 2.3316 (1.14); 2.3269 (1.48); 2.3224 (1.12); 2.0849 (1.22); 2.0691 (1.99); 1.9867 (1.36); 1.9079 (0.38); 1.7282 (0.53); 1.7038 (0.50); 1.5642 (0.54); 1.5398 (0.53); 1.2373 (0.48); 1.1925 (0.44); 1.1749 (0.77); 1.1571 (0.41); −0.0002 (4.82);

Ex. 5, Solvent: DMSO, Spectrometer: 399.95 MHz 9.2895 (1.04); 8.0347 (0.61); 8.0224 (6.52); 7.4399 (1.29); 7.4356 (0.88); 7.4228 (1.56); 7.4191 (1.32); 7.4070 (0.46); 7.4029 (0.38); 7.3981 (0.62); 7.3923 (0.44); 7.3782 (1.60); 7.3679 (3.08); 7.3624 (5.05); 7.3596 (4.74); 7.3499 (1.29); 7.3461 (0.94); 7.3426 (1.20); 7.3366 (0.93); 7.3268 (0.41); 7.3205 (0.35); 6.4907 (3.72); 6.1225 (1.00); 6.1019 (1.23); 6.0951 (1.18); 6.0744 (1.01); 5.3418 (0.63); 5.2993 (2.10); 5.2489 (2.11); 5.2062 (0.63); 4.3833 (0.64); 4.3517 (0.68); 4.0571 (0.33); 4.0393 (0.99); 4.0216 (1.04); 4.0036 (0.56); 3.9893 (0.65); 3.9556 (1.68); 3.9278 (1.16); 3.9117 (1.37); 3.8841 (1.04); 3.6914 (0.58); 3.4098 (0.54); 3.3999 (0.46); 3.3897 (0.68); 3.3809 (1.08); 3.3716 (0.76); 3.3639 (0.87); 3.3518 (0.89); 3.3415 (0.94); 3.3111 (259.73); 3.2902 (3.79); 3.2674 (2.30); 3.2469 (1.47); 3.2388 (0.80); 3.1410 (0.38); 3.0627 (1.24); 3.0367 (16.00); 2.8689 (0.47); 2.8397 (0.83); 2.8127 (0.49); 2.5227 (0.93); 2.5094 (15.18); 2.5051 (28.85); 2.5006 (38.17); 2.4962 (26.96); 2.4919 (13.31); 2.2395 (0.55); 2.2089 (13.78); 2.1942 (1.10); 2.1356 (0.66); 2.1070 (1.31); 2.0692 (0.96); 1.9868 (4.35); 1.8229 (0.53); 1.8181 (0.54); 1.7939 (0.54); 1.5861 (0.53); 1.5774 (0.55); 1.5554 (0.54); 1.5469 (0.49); 1.1928 (1.19); 1.1750 (2.37); 1.1572 (1.17); −0.0002 (3.61);

Ex. 6, Solvent: DMSO, Spectrometer: 399.95 MHz 9.2891 (0.72); 8.6090 (2.11); 8.0212 (5.44); 7.7010 (1.17); 7.6808 (1.36); 7.5331 (1.79); 7.4826 (1.13); 7.4629 (0.95); 7.4392 (0.99); 7.4219 (1.32); 7.3812 (0.58); 7.3765 (1.02); 7.3737 (0.84); 7.3657 (2.95); 7.3610 (4.08); 7.3486 (1.19); 7.3386 (0.95); 7.3329 (0.62); 7.3231 (0.41); 7.3165 (0.33); 7.2175 (1.04); 7.2125 (0.84); 7.0783 (2.26); 6.9389 (1.27); 6.1220 (0.82); 6.1014 (1.01); 6.0944 (0.95); 6.0738 (0.82); 5.7462 (2.07); 4.1756 (1.13); 4.1420 (1.16); 4.0571 (1.24); 4.0392 (3.64); 4.0215 (3.66); 4.0037 (1.25); 3.9569 (0.80); 3.9293 (0.95); 3.9132 (1.04); 3.8857 (0.86); 3.3658 (0.95); 3.3562 (1.26); 3.3115 (379.65); 3.2929 (3.24); 3.2881 (3.63); 3.2699 (1.15); 3.2492 (0.96); 3.0674 (0.78); 3.0335 (14.21); 3.0093 (0.89); 2.6696 (0.36); 2.5395 (0.51); 2.5227 (1.67); 2.5094 (21.20); 2.5050 (39.09); 2.5006 (50.66); 2.4961 (34.76); 2.4917 (16.36); 2.3273 (0.33); 2.2178 (0.36); 2.1093 (0.96); 2.0839 (1.04); 2.0692 (0.85); 1.9868 (16.00); 1.7223 (0.39); 1.7017 (0.78); 1.6925 (0.89); 1.6709 (0.81); 1.6622 (0.78); 1.6401 (0.32); 1.1928 (4.42); 1.1750 (8.83); 1.1572 (4.29); −0.0002 (3.01);

Ex. 7, Solvent: DMSO, Spectrometer: 399.95 MHz 10.1836 (3.67); 8.0340 (1.04); 8.0300 (1.06); 8.0234 (0.39); 8.0136 (1.65); 8.0089 (4.95); 7.7370 (0.43); 7.7337 (0.44); 7.7181 (1.11); 7.6992 (0.83); 7.6958 (0.77); 7.6247 (1.02); 7.6151 (1.42); 7.6082 (1.43); 7.5965 (0.99); 7.5902 (0.70); 6.4891 (2.20); 6.4455 (0.64); 6.4295 (0.73); 6.4178 (0.72); 6.4016 (0.65); 5.3357 (0.39); 5.2934 (1.36); 5.2448 (1.33); 5.2022 (0.40); 4.3745 (0.40); 4.3415 (0.42); 4.0904 (0.73); 4.0623 (0.98); 4.0582 (1.38); 4.0465 (1.15); 4.0403 (3.76); 4.0225 (3.92); 4.0047 (1.32); 3.9801 (0.39); 3.9464 (0.42); 3.3867 (0.33); 3.3675 (0.44); 3.3582 (0.71); 3.3486 (0.53); 3.3119 (67.25); 3.2901 (1.13); 3.2567 (0.61); 3.2245 (1.14); 3.2083 (0.92); 3.1808 (0.82); 3.1646 (0.81); 2.8299 (0.49); 2.5242 (0.45); 2.5109 (5.48); 2.5066 (9.98); 2.5022 (12.87); 2.4978 (8.97); 2.4934 (4.35); 2.2075 (8.36); 2.1937 (0.49); 2.1142 (0.38); 2.0859 (0.79); 2.0539 (0.45); 1.9879 (16.00); 1.8041 (0.33); 1.5593 (0.33); 1.1937 (4.44); 1.1759 (8.69); 1.1581 (4.32); −0.0002 (1.14);

Ex. 8, Solvent: DMSO, Spectrometer: 399.95 MHz 8.0325 (7.66); 7.3371 (0.58); 7.3239 (0.66); 7.3135 (1.27); 7.3006 (1.28); 7.2903 (0.80); 7.2774 (0.69); 7.1557 (0.88); 7.1517 (0.92); 7.1310 (1.53); 7.1282 (1.53); 7.1075 (0.72); 7.1039 (0.75); 6.4985 (4.27); 6.0167 (1.08); 5.9957 (1.29); 5.9867 (1.24); 5.9655 (1.13); 5.7569 (5.74); 5.3556 (0.89); 5.3130 (2.67); 5.2626 (2.59); 5.2199 (0.87); 4.8983 (6.61); 4.8924 (6.85); 4.3934 (0.74); 4.3595 (0.79); 4.0554 (0.42); 4.0376 (1.27); 4.0198 (1.32); 4.0018 (0.93); 3.9614 (0.79); 3.9404 (0.88); 3.9094 (0.93); 3.8967 (1.11); 3.8666 (0.96); 3.6481 (1.57); 3.6423 (3.36); 3.6365 (1.60); 3.5741 (1.15); 3.5528 (1.15); 3.5305 (0.96); 3.5096 (0.94); 3.4245 (0.50); 3.4152 (0.35); 3.4055 (0.61); 3.3964 (1.06); 3.3870 (0.61); 3.3773 (0.38); 3.3676 (0.56); 3.3225 (46.65); 3.3203 (44.06); 3.2718 (1.05); 3.2434 (0.58); 2.8715 (0.52); 2.8411 (0.95); 2.8131 (0.55); 2.6702 (0.42); 2.5056 (48.88); 2.5012 (65.94); 2.4967 (48.92); 2.3322 (0.35); 2.3279 (0.48); 2.3234 (0.37); 2.2090 (16.00); 2.1483 (0.73); 2.1167 (1.47); 2.0843 (0.81); 1.9886 (5.44); 1.8305 (0.63); 1.8063 (0.59); 1.5951 (0.59); 1.5861 (0.66); 1.5648 (0.62); 1.5551 (0.59); 1.2350 (0.41); 1.1921 (1.52); 1.1744 (2.98); 1.1565 (1.49); −0.0002 (0.53);

Ex. 9, Solvent: DMSO, Spectrometer: 601.6 MHz 8.7986 (0.66); 8.0310 (8.32); 7.2995 (0.69); 7.2946 (0.76); 7.2881 (0.78); 7.2832 (1.00); 7.2804 (0.82); 7.2719 (1.20); 7.2640 (0.95); 7.1948 (0.36); 7.1816 (1.61); 7.1749 (4.74); 7.1700 (3.35); 7.1620 (0.57); 6.5053 (4.59); 5.9817 (1.40); 5.9695 (1.56); 5.9631 (1.51); 5.9508 (1.40); 5.3490 (1.22); 5.3206 (2.49); 5.2629 (2.73); 5.2345 (1.36); 4.8465 (6.64); 4.8425 (6.72); 4.3803 (0.78); 4.3586 (0.79); 4.0454 (0.50); 4.0335 (1.51); 4.0217 (1.53); 4.0099 (0.52); 3.9788 (0.77); 3.9559 (0.83); 3.9467 (1.50); 3.9279 (1.43); 3.9180 (1.55); 3.8993 (1.28); 3.6568 (1.85); 3.6528 (3.82); 3.6489 (1.79); 3.4028 (0.55); 3.3968 (0.89); 3.3901 (0.81); 3.3837 (1.25); 3.3774 (2.09); 3.3501 (362.44); 3.3314 (3.04); 3.3265 (6.83); 3.3192 (2.05); 3.2812 (0.72); 3.2610 (1.14); 3.2424 (0.63); 3.2383 (0.57); 2.8500 (0.59); 2.8293 (1.02); 2.8118 (0.58); 2.6180 (0.80); 2.6150 (1.06); 2.6119 (0.84); 2.5955 (0.79); 2.5427 (0.99); 2.5242 (3.13); 2.5211 (3.99); 2.5180 (4.63); 2.5091 (55.45); 2.5062 (113.82); 2.5032 (153.80); 2.5002 (112.48); 2.4973 (52.77); 2.3904 (0.76); 2.3874 (1.01); 2.3844 (0.75); 2.2050 (16.00); 2.1921 (0.42); 2.1267 (1.03); 2.1005 (1.11); 2.0964 (1.11); 2.0782 (2.13); 1.9905 (6.69); 1.8367 (0.34);

1.8301 (0.39); 1.8160 (0.72); 1.8101 (0.76); 1.7955 (0.72); 1.7897 (0.64); 1.5690 (0.67); 1.5625 (0.69); 1.5483 (0.68); 1.5424 (0.63); 1.3968 (0.37); 1.2335 (0.74); 1.1860 (1.93); 1.1741 (4.07); 1.1623 (2.09); 1.0380 (0.32); 1.0270 (0.34); 0.0052 (1.52); −0.0002 (35.42); −0.0058 (1.08);

Ex. 10, Solvent: CDCl3, Spectrometer: 601.6 MHz 7.6273 (0.91); 7.4326 (0.47); 7.3245 (1.12); 7.3113 (2.15); 7.2984 (1.22); 7.2614 (79.66); 7.0850 (0.46); 7.0266 (1.81); 7.0149 (3.61); 6.9414 (1.96); 6.9281 (1.90); 6.3350 (6.11); 5.7351 (0.78); 5.0298 (0.59); 5.0034 (1.60); 4.9737 (1.59); 4.9498 (0.67); 4.7006 (6.62); 4.6971 (6.67); 4.5817 (0.75); 4.5629 (0.74); 4.0571 (0.70); 4.0394 (0.71); 3.8349 (0.45); 3.8052 (0.32); 3.7893 (0.48); 3.6444 (0.47); 3.4187 (0.48); 3.3067 (1.20); 2.9123 (0.46); 2.8936 (0.76); 2.8745 (0.47); 2.5105 (2.38); 2.5071 (4.68); 2.5036 (2.42); 2.3239 (16.00); 2.2858 (0.44); 2.2145 (0.77); 2.1812 (0.75); 2.1629 (0.73); 1.7957 (0.89); 1.7805 (0.92); 1.5858 (3.62); 1.4787 (0.49); 1.4746 (0.46); 1.4321 (1.33); 1.4270 (0.89); 1.3860 (0.35); 1.3330 (0.38); 1.2928 (0.37); 1.2844 (0.63); 1.2542 (3.05); 0.8801 (0.63); 0.8683 (0.37); 0.0695 (1.41); 0.0051 (0.53); −0.0002 (16.59); −0.0057 (0.63);

Ex. 11, Solvent: DMSO, Spectrometer: 399.95 MHz 7.9670 (8.64); 7.4133 (1.85); 7.3924 (3.34); 7.3720 (2.70); 7.1610 (3.06); 7.1564 (4.00); 7.1394 (2.50); 7.1365 (3.63); 6.5060 (4.36); 6.4950 (0.39); 6.2328 (1.37); 6.2083 (1.80); 6.2020 (1.66); 6.1773 (1.43); 5.7627 (11.00); 5.3613 (0.91); 5.3188 (2.57); 5.2700 (2.50); 5.2274 (0.88); 5.2032 (0.65); 4.8393 (0.34); 4.8331 (0.35); 4.7990 (2.74); 4.7910 (3.74); 4.7843 (2.83); 4.7503 (0.35); 4.7444 (0.36); 4.3942 (0.68); 4.3599 (0.74); 4.0366 (0.92); 4.0188 (0.97); 4.0009 (0.80); 3.9622 (0.72); 3.7667 (1.02); 3.7357 (1.26); 3.7247 (1.76); 3.6937 (1.42); 3.5797 (1.57); 3.5551 (1.60); 3.5376 (1.16); 3.5132 (1.16); 3.4596 (1.33); 3.4540 (3.13); 3.4482 (1.65); 3.4179 (0.79); 3.3720 (137.80); 3.3689 (145.30); 3.3659 (149.76); 3.3644 (142.87); 3.3627 (145.05); 3.3600 (158.31); 3.3560 (182.12); 3.3095 (0.97); 3.3026 (0.97); 3.2719 (1.19); 3.2437 (0.75); 3.0425 (1.70); 2.8727 (0.55); 2.8540 (1.66); 2.8448 (0.94); 2.8151 (0.55); 2.6774 (0.52); 2.6728 (0.75); 2.6682 (0.55); 2.5431 (0.37); 2.5262 (1.22); 2.5215 (1.91); 2.5128 (37.79); 2.5083 (83.02); 2.5037 (112.86); 2.4991 (80.19); 2.4945 (37.37); 2.3350 (0.54); 2.3304 (0.75); 2.3258 (0.59); 2.2082 (16.00); 2.1945 (0.98); 2.1899 (1.51); 2.1522 (0.65); 2.1249 (1.35); 2.0903 (0.76); 2.0774 (1.61); 1.9902 (4.31); 1.8271 (0.61); 1.8026 (0.55); 1.5943 (0.55); 1.5852 (0.62); 1.5638 (0.59); 1.5543 (0.58); 1.1920 (1.20); 1.1742 (2.43); 1.1564 (1.18); 0.0080 (0.86); −0.0002 (29.91); −0.0085 (1.06);

Ex. 12, Solvent: DMSO, Spectrometer: 399.95 MHz 7.9807 (7.00); 7.9525 (2.03); 7.4372 (0.62); 7.4201 (0.81); 7.4161 (1.37); 7.3992 (1.36); 7.3953 (0.92); 7.3783 (0.71); 7.0116 (2.03); 6.9903 (1.83); 6.9152 (1.03); 6.8897 (1.23); 6.8681 (0.97); 6.5040 (3.54); 6.0725 (0.87); 6.0502 (1.06); 6.0421 (1.05); 6.0198 (0.93); 5.7619 (3.47); 5.3612 (0.79); 5.3185 (2.23); 5.2681 (2.18); 5.2254 (0.77); 5.2021 (0.39); 4.8549 (2.83); 4.8494 (4.94); 4.8440 (2.89); 4.3947 (0.60); 4.3602 (0.65); 3.9953 (0.56); 3.9617 (0.63); 3.8129 (0.58); 3.7816 (0.67); 3.7697 (0.84); 3.7394 (0.76); 3.5560 (1.45); 3.5502 (3.42); 3.5443 (1.54); 3.5246 (1.00); 3.5023 (1.02); 3.4818 (0.82); 3.4598 (0.76); 3.4187 (0.44); 3.4089 (0.41); 3.3998 (0.66); 3.3913 (1.02); 3.3798 (0.82); 3.3704 (1.02); 3.3457 (545.02); 3.3221 (4.34); 3.3102 (1.10); 3.3056 (1.13); 3.3023 (1.08); 3.2853 (0.48); 3.2711 (1.05); 3.2430 (0.56); 3.0425 (0.81); 2.8905 (16.00); 2.8710 (0.48); 2.8540 (0.86); 2.8400 (0.81); 2.8132 (0.46); 2.7305 (13.08); 2.6765 (0.51); 2.6719 (0.75); 2.6675 (0.56); 2.5251 (1.29); 2.5116 (41.13); 2.5073 (87.25); 2.5029 (117.49); 2.4984 (86.16); 2.4940 (42.72); 2.3339 (0.59); 2.3295 (0.81); 2.3250 (0.63); 2.2085 (13.04); 2.1948 (1.13); 2.1521 (0.59); 2.1218 (1.21); 2.0879 (0.69); 2.0769 (1.06); 1.8268 (0.53); 1.8037 (0.49); 1.5934 (0.48); 1.5834 (0.56); 1.5624 (0.51); 1.5537 (0.50); 1.2342 (0.40); −0.0002 (8.23); −0.0082 (0.39);

Ex. 13, Solvent: DMSO, Spectrometer: 399.95 MHz 14.0244 (0.35); 8.7870 (0.54); 8.0352 (0.87); 8.0139 (7.56); 7.9916 (0.41); 7.4835 (0.44); 7.3543 (0.48); 7.3427 (0.95); 7.3228 (3.44); 7.3042 (2.77); 7.2237 (0.37); 7.1506 (1.98); 7.1313 (1.63); 7.0188 (1.03); 7.0022 (2.00); 6.9812 (0.94); 6.4963 (4.60); 6.4409 (0.35); 5.8865 (0.96); 5.8680 (1.10); 5.8584 (1.12); 5.8418 (0.94); 5.7554 (7.99); 5.3481 (0.81); 5.3051 (2.51); 5.2549 (2.40); 5.2126 (0.97); 4.9731 (0.39); 4.8801 (5.11); 4.8742 (5.27); 4.8150 (0.71); 4.3826 (0.80); 4.3501 (0.83); 4.0743 (0.38); 4.0556 (0.68); 4.0374 (1.57); 4.0200 (1.64); 4.0020 (0.67); 3.9809 (0.75); 3.9478 (1.00); 3.9202 (0.45); 3.8988 (1.16); 3.8703 (1.18); 3.8556 (1.32); 3.8277 (1.08); 3.6664 (0.48); 3.5857 (1.80); 3.5799 (3.73); 3.5739 (1.64); 3.4875 (0.36); 3.4448 (0.36); 3.3987 (0.82); 3.3776 (1.05); 3.3700 (1.49); 3.3581 (1.33); 3.3228 (817.78); 3.2695 (1.87); 3.2515 (1.78); 3.2263 (1.66); 3.2089 (1.19); 2.8589 (0.68); 2.8302 (1.05); 2.8000 (0.72); 2.6750 (1.40); 2.6704 (2.12); 2.6660 (1.35); 2.5407 (1.00); 2.5236 (3.21); 2.5096 (115.86); 2.5056 (225.44); 2.5012 (312.93); 2.4970 (220.11); 2.4928 (110.70); 2.3323 (1.37); 2.3278 (1.83); 2.3232 (1.36); 2.2160 (1.34); 2.2057 (16.00); 2.1935 (1.07); 2.1279 (0.79); 2.0993 (1.48); 2.0918 (1.41); 2.0733 (1.50); 2.0630 (0.99); 1.9884 (6.91); 1.9085 (0.84); 1.8351 (0.38); 1.8160 (0.73); 1.7837 (0.64); 1.6017 (0.35); 1.5716 (0.65); 1.5643 (0.65); 1.5516 (0.49); 1.5420 (0.71); 1.5104 (0.36); 1.2338 (0.91); 1.1922 (1.92); 1.1745 (3.72); 1.1567 (1.78); −0.0002 (5.87);

Ex. 14, Solvent: DMSO, Spectrometer: 399.95 MHz 8.3198 (0.45); 8.0443 (16.00); 7.6053 (8.46); 7.4479 (2.82); 7.4440 (3.38); 7.4289 (3.83); 7.4249 (4.61); 7.4157 (1.89); 7.4115 (1.78); 7.3965 (3.75); 7.3921 (3.24); 7.3771 (3.07); 7.3727 (2.56); 7.3116 (2.76); 7.3090 (3.00); 7.2927 (4.30); 7.2903 (4.41); 7.2742 (1.69); 7.2714 (1.67); 7.1953 (0.33); 7.1890 (0.37); 7.1773 (4.76); 7.1747 (4.70); 7.1646 (0.64); 7.1572 (4.19); 7.1547 (3.90); 7.0597 (0.56); 7.0538 (0.44); 6.9641 (0.42); 6.9357 (0.32); 5.7610 (2.36); 5.7415

(2.76); 5.7327 (2.75); 5.7131 (2.43); 5.6385 (1.87); 5.5956 (4.12); 5.5268 (4.32); 5.4837 (1.93); 5.2693 (1.37); 5.1452 (0.97); 4.3548 (1.53); 4.3219 (1.65); 4.2712 (0.57); 4.2535 (0.57); 4.1720 (0.81); 4.1542 (0.81); 4.0376 (0.50); 4.0198 (0.52); 3.9738 (1.43); 3.9402 (1.61); 3.8975 (2.31); 3.8689 (2.63); 3.8543 (2.98); 3.8258 (2.50); 3.4591 (6.28); 3.4189 (2.28); 3.4100 (1.64); 3.3991 (1.84); 3.3896 (2.54); 3.3804 (1.64); 3.3705 (1.13); 3.3608 (1.37); 3.3524 (0.85); 3.3033 (1.33); 3.2908 (3.27); 3.2715 (5.00); 3.2551 (1.06); 3.2475 (3.40); 3.2283 (2.80); 2.8827 (1.10); 2.8529 (1.97); 2.8254 (1.12); 2.6763 (0.67); 2.6719 (0.93); 2.6674 (0.70); 2.5251 (2.77); 2.5116 (51.56); 2.5073 (103.29); 2.5028 (137.32); 2.4983 (103.49); 2.4940 (53.38); 2.3383 (0.39); 2.3341 (0.72); 2.3296 (0.98); 2.3250 (0.76); 2.1282 (1.37); 2.0962 (2.94); 2.0665 (1.68); 1.9896 (2.19); 1.8721 (0.77); 1.8557 (1.68); 1.8402 (2.83); 1.8344 (2.00); 1.8291 (2.06); 1.8213 (2.02); 1.8092 (1.64); 1.8011 (1.32); 1.7709 (1.16); 1.7423 (0.46); 1.5818 (0.52); 1.5725 (0.61); 1.5514 (1.21); 1.5424 (1.31); 1.5208 (1.42); 1.5096 (1.32); 1.5013 (0.75); 1.4976 (0.58); 1.4893 (1.15); 1.4832 (0.66); 1.4775 (0.66); 1.4697 (0.52); 1.3973 (6.91); 1.3362 (0.81); 1.2837 (0.58); 1.2659 (1.15); 1.2587 (0.35); 1.2486 (1.33); 1.2341 (0.81); 1.2155 (0.95); 1.1977 (1.80); 1.1929 (0.73); 1.1798 (1.22); 1.1751 (1.33); 1.1611 (0.85); 1.1573 (0.83); 1.1435 (0.42); 1.0719 (0.82); 1.0639 (1.00); 1.0562 (1.20); 1.0509 (2.43); 1.0454 (3.02); 1.0299 (5.26); 1.0181 (3.59); 1.0131 (5.32); 1.0065 (4.05); 1.0009 (2.53); 0.9945 (2.60); 0.9852 (2.73); 0.9784 (2.29); 0.9715 (1.96); 0.9603 (2.81); 0.9461 (1.55); 0.9397 (1.46); 0.9268 (0.72); 0.9190 (0.42); 0.8188 (0.79); 0.8116 (1.69); 0.8057 (0.80); 0.7989 (0.71); 0.7916 (1.70); 0.7858 (1.34); 0.7792 (1.57); 0.7723 (1.40); 0.7679 (1.82); 0.7604 (0.79); 0.7031 (0.49); 0.6996 (0.42); 0.6916 (0.93); 0.6717 (0.48); 0.1459 (0.40); 0.0080 (3.19); −0.0002 (88.57); −0.0083 (4.15); −0.1498 (0.41);

Ex. 15, Solvent: DMSO, Spectrometer: 399.95 MHz 8.0022 (6.06); 7.2119 (2.20); 7.1906 (2.38); 7.0017 (1.16); 6.8645 (2.76); 6.7274 (1.32); 6.6819 (2.46); 6.6761 (2.69); 6.5676 (1.45); 6.5618 (1.32); 6.5464 (1.38); 6.5405 (1.27); 6.2950 (2.93); 5.8001 (0.91); 5.7812 (1.08); 5.7726 (1.04); 5.7536 (0.91); 5.2633 (0.66); 5.2211 (2.00); 5.1739 (1.99); 5.1317 (0.66); 4.7914 (3.28); 4.7856 (3.33); 4.3874 (0.60); 4.3555 (0.64); 4.0550 (0.61); 4.0372 (1.88); 4.0194 (2.07); 4.0016 (1.16); 3.9720 (0.63); 3.8129 (0.51); 3.8030 (0.90); 3.7752 (1.07); 3.7601 (1.52); 3.7498 (16.00); 3.7327 (1.19); 3.3994 (0.46); 3.3898 (0.41); 3.3804 (0.62); 3.3705 (1.06); 3.3443 (19.58); 3.2887 (1.45); 3.2698 (1.23); 3.2462 (1.44); 3.2269 (1.21); 2.8478 (0.42); 2.8168 (0.73); 2.7894 (0.42); 2.6759 (0.35); 2.6714 (0.50); 2.6667 (0.36); 2.5246 (1.35); 2.5111 (28.23); 2.5067 (57.28); 2.5022 (77.36); 2.4977 (59.44); 2.4933 (31.35); 2.3335 (0.45); 2.3290 (0.59); 2.3246 (0.45); 2.1850 (11.90); 2.1215 (0.63); 2.0914 (1.22); 2.0625 (0.73); 1.9894 (8.21); 1.9090 (6.30); 1.8492 (0.43); 1.8437 (0.49); 1.8203 (4.10); 1.8147 (8.12); 1.8090 (4.37); 1.7947 (0.89); 1.7870 (0.79); 1.7650 (0.65); 1.7334 (0.36); 1.7090 (0.40); 1.5650 (0.52); 1.5556 (0.57); 1.5342 (0.54); 1.5248 (0.51); 1.3972 (4.83); 1.1924 (2.19); 1.1746 (4.35); 1.1568 (2.16); −0.0002 (4.21);

Ex. 16, Solvent: DMSO, Spectrometer: 399.95 MHz 8.0006 (2.31); 7.6034 (1.53); 7.2960 (0.90); 7.2769 (1.11); 7.2613 (0.46); 7.0222 (0.79); 7.0014 (0.64); 6.9487 (0.48); 6.9297 (0.81); 6.9115 (0.38); 5.8714 (0.37); 5.8527 (0.45); 5.8428 (0.41); 5.8247 (0.38); 5.6335 (0.34); 5.5902 (0.75); 5.5240 (0.77); 5.4812 (0.35); 4.0375 (0.46); 4.0198 (0.47); 3.9353 (0.34); 3.9227 (0.42); 3.9055 (0.37); 3.8967 (0.66); 3.8798 (0.68); 3.8683 (0.49); 3.8608 (0.68); 3.8417 (0.85); 3.8254 (0.59); 3.8173 (0.39); 3.7974 (0.51); 3.3817 (0.40); 3.3519 (0.84); 3.3277 (40.80); 3.3089 (0.72); 3.2908 (0.55); 3.2726 (0.39); 2.8544 (0.37); 2.5065 (34.94); 2.5021 (44.66); 2.4978 (32.56); 2.0951 (0.53); 1.9892 (1.91); 1.7901 (0.47); 1.3975 (16.00); 1.1926 (0.65); 1.1748 (1.22); 1.1635 (0.38); 1.1569 (0.69); 0.4971 (0.47); 0.4926 (0.48); 0.4770 (0.35); 0.4719 (0.39); 0.4383 (0.41); 0.4355 (0.42); 0.4156 (0.53); 0.3161 (0.39); 0.3042 (1.21); 0.2920 (1.16); 0.2798 (0.33); 0.0074 (0.34); −0.0002 (6.70);

Ex. 17, Solvent: DMSO, Spectrometer: 399.95 MHz 7.9983 (5.82); 7.2945 (1.82); 7.2899 (1.35); 7.2782 (2.10); 7.2749 (2.41); 7.2605 (1.12); 7.2564 (0.65); 7.0215 (1.85); 7.0012 (1.44); 6.9475 (1.09); 6.9288 (1.88); 6.9100 (0.90); 6.4963 (3.32); 5.8720 (0.93); 5.8540 (1.03); 5.8439 (1.00); 5.8256 (0.91); 5.3524 (0.74); 5.3099 (2.04); 5.2561 (2.05); 5.2139 (0.74); 4.3815 (0.61); 4.3486 (0.65); 4.0554 (1.24); 4.0376 (3.73); 4.0198 (3.80); 4.0020 (1.38); 3.9778 (0.62); 3.9512 (0.66); 3.9230 (0.77); 3.9060 (0.81); 3.8974 (1.53); 3.8805 (1.59); 3.8675 (1.14); 3.8613 (1.62); 3.8436 (1.73); 3.8396 (1.60); 3.8247 (1.40); 3.8181 (0.87); 3.7966 (1.17); 3.4009 (0.48); 3.3909 (0.41); 3.3814 (0.57); 3.3722 (0.95); 3.3627 (0.70); 3.3497 (1.79); 3.3276 (79.63); 3.3070 (1.34); 3.2891 (1.39); 3.2626 (0.80); 3.2345 (0.46); 2.8634 (0.46); 2.8364 (0.77); 2.8052 (0.44); 2.6755 (0.35); 2.6711 (0.48); 2.6666 (0.37); 2.5413 (0.36); 2.5242 (1.94); 2.5109 (26.73); 2.5066 (52.99); 2.5020 (70.08); 2.4975 (51.35); 2.4931 (24.86); 2.3334 (0.36); 2.3287 (0.49); 2.3242 (0.35); 2.2060 (12.17); 2.1946 (1.38); 2.1218 (0.64); 2.0943 (1.15); 2.0628 (0.65); 1.9889 (16.00); 1.8140 (0.48); 1.8048 (0.53); 1.7901 (0.65); 1.7831 (0.48); 1.7735 (0.44); 1.5719 (0.45); 1.5629 (0.48); 1.5414 (0.44); 1.3975 (3.38); 1.2981 (0.32); 1.2585 (0.46); 1.1928 (4.73); 1.1823 (0.70); 1.1750 (9.35); 1.1655 (0.93); 1.1572 (4.79); 1.1484 (0.55); 0.5290 (0.41); 0.5213 (0.46); 0.5172 (0.45); 0.5093 (0.62); 0.5002 (1.09); 0.4953 (1.09); 0.4799 (0.79); 0.4747 (0.87); 0.4435 (0.90); 0.4399 (0.93); 0.4232 (1.00); 0.4197 (1.14); 0.4111 (0.52); 0.3980 (0.53); 0.3912 (0.48); 0.3410 (0.34); 0.3288 (0.49); 0.3178 (0.85); 0.3058 (2.78); 0.2987 (1.55); 0.2937 (2.71); 0.2884 (0.99); 0.2816 (0.72); 0.2705 (0.33); 0.0079 (0.51); −0.0002 (13.14); −0.0084 (0.45);

Ex. 18, Solvent: DMSO, Spectrometer: 399.95 MHz 8.0100 (7.83); 7.3118 (1.40); 7.3083 (1.78); 7.3041 (1.62); 7.2943 (2.33); 7.2897 (2.40); 7.2853 (1.75);

7.2763 (1.44); 7.2721 (0.74); 7.2072 (1.33); 7.0725 (3.05); 7.0619 (2.31); 7.0512 (0.40); 7.0415 (1.80); 6.9747 (1.29); 6.9548 (2.22); 6.9378 (2.47); 6.3833 (3.14); 6.0804 (0.38); 6.0679 (0.83); 6.0545 (0.62); 6.0414 (0.95); 6.0372 (0.50); 6.0289 (0.50); 6.0246 (1.01); 6.0117 (0.70); 5.9981 (1.01); 5.9857 (0.48); 5.9181 (1.13); 5.9002 (1.30); 5.8903 (1.27); 5.8723 (1.15); 5.7570 (3.27); 5.4432 (0.61); 5.4389 (1.72); 5.4346 (1.75); 5.4303 (0.63); 5.3999 (0.53); 5.3956 (1.50); 5.3913 (1.52); 5.3870 (0.54); 5.2461 (1.93); 5.2421 (2.23); 5.2232 (0.68); 5.2196 (1.65); 5.2156 (1.65); 5.2119 (0.72); 5.1988 (2.50); 5.1594 (2.44); 5.1170 (0.61); 4.6326 (2.29); 4.6277 (2.51); 4.6207 (2.41); 4.6155 (2.15); 4.3629 (0.64); 4.3301 (0.66); 4.0380 (0.34); 4.0201 (0.36); 4.0020 (0.38); 3.9912 (0.60); 3.9560 (0.65); 3.8912 (1.23); 3.8632 (1.40); 3.8483 (1.59); 3.8205 (1.34); 3.3920 (0.47); 3.3822 (0.34); 3.3726 (0.57); 3.3633 (1.01); 3.3540 (0.59); 3.3439 (0.40); 3.3344 (0.69); 3.3217 (20.52); 3.2980 (1.00); 3.2864 (1.56); 3.2684 (1.90); 3.2434 (1.82); 3.2358 (0.93); 3.2257 (1.60); 3.2068 (0.46); 2.8344 (0.45); 2.8070 (0.80); 2.7767 (0.45); 2.5239 (0.38); 2.5104 (8.89); 2.5060 (18.38); 2.5015 (24.50); 2.4969 (17.47); 2.4925 (8.24); 2.1608 (16.00); 2.1069 (0.59); 2.0769 (1.25); 2.0475 (0.69); 1.9888 (1.44); 1.7741 (0.52); 1.7658 (0.56); 1.7431 (0.51); 1.7356 (0.48); 1.5590 (0.50); 1.5502 (0.54); 1.5283 (0.51); 1.5194 (0.49); 1.1923 (0.40); 1.1745 (0.79); 1.1567 (0.39); −0.0002 (2.77);

Ex. 19, Solvent: DMSO, Spectrometer: 399.95 MHz 8.0312 (8.75); 7.2693 (0.58); 7.2561 (0.65); 7.2458 (1.28); 7.2329 (1.27); 7.2224 (0.79); 7.2095 (0.70); 7.1053 (0.91); 7.1011 (0.94); 7.0806 (1.50); 7.0776 (1.46); 7.0573 (0.72); 7.0529 (0.72); 6.4986 (4.24); 6.0692 (0.43); 6.0559 (0.90); 6.0428 (0.88); 6.0295 (1.08); 6.0261 (0.60); 6.0129 (2.13); 5.9996 (1.15); 5.9927 (1.37); 5.9862 (1.78); 5.9732 (0.64); 5.9624 (1.15); 5.7570 (0.58); 5.4267 (0.69); 5.4226 (1.94); 5.4184 (1.98); 5.4144 (0.73); 5.3836 (0.61); 5.3795 (1.70); 5.3752 (1.75); 5.3711 (0.66); 5.3554 (0.86); 5.3128 (2.63); 5.2955 (0.92); 5.2922 (1.94); 5.2882 (1.83); 5.2621 (4.13); 5.2201 (0.87); 4.6447 (2.44); 4.6414 (4.03); 4.6380 (2.54); 4.6315 (2.56); 4.6281 (3.94); 4.6248 (2.36); 4.3925 (0.70); 4.3596 (0.74); 4.0555 (0.72); 4.0377 (2.18); 4.0199 (2.24); 4.0020 (1.21); 3.9612 (0.74); 3.9377 (0.84); 3.9073 (0.91); 3.8944 (1.09); 3.8642 (0.96); 3.5677 (3.27); 3.5469 (1.17); 3.5247 (0.95); 3.5037 (0.94); 3.4241 (0.52); 3.4148 (0.36); 3.4049 (0.61); 3.3955 (1.10); 3.3863 (0.63); 3.3760 (0.41); 3.3667 (0.58); 3.3573 (0.34); 3.3203 (81.65); 3.2966 (3.58); 3.2716 (0.97); 3.2433 (0.53); 3.0430 (0.53); 2.8705 (0.50); 2.8545 (0.64); 2.8441 (0.89); 2.8134 (0.52); 2.6748 (0.40); 2.6703 (0.56); 2.6657 (0.41); 2.5237 (1.15); 2.5102 (29.77); 2.5058 (61.50); 2.5012 (81.81); 2.4966 (58.12); 2.4922 (27.28); 2.3328 (0.40); 2.3279 (0.56); 2.3233 (0.41); 2.2095 (16.00); 2.1930 (0.82); 2.1485 (0.67); 2.1195 (1.36); 2.0862 (0.74); 1.9886 (9.64); 1.8292 (0.58); 1.8061 (0.53); 1.5944 (0.55); 1.5857 (0.61); 1.5651 (0.56); 1.5559 (0.55); 1.3975 (1.01); 1.1922 (2.65); 1.1744 (5.35); 1.1566 (2.61); −0.0002 (8.47);

Ex. 20, Solvent: DMSO, Spectrometer: 601.6 MHz 8.0151 (9.12); 7.3155 (3.02); 7.3017 (3.39); 7.2357 (3.79); 7.2325 (3.96); 7.0807 (2.16); 7.0775 (2.10); 7.0671 (1.98); 7.0639 (1.94); 6.9503 (1.30); 6.8591 (3.31); 6.7680 (1.51); 6.2923 (3.51); 5.8374 (1.29); 5.8259 (1.41); 5.8191 (1.38); 5.8074 (1.30); 5.7541 (10.11); 5.2465 (1.00); 5.2183 (2.32); 5.1637 (2.28); 5.1354 (0.99); 4.9420 (6.32); 4.9380 (6.43); 4.3777 (0.68); 4.3555 (0.71); 4.0469 (0.32); 4.0350 (1.02); 4.0232 (1.03); 4.0113 (0.38); 3.9959 (0.64); 3.9729 (0.69); 3.8884 (1.32); 3.8699 (1.56); 3.8599 (1.67); 3.8414 (1.38); 3.6384 (1.82); 3.6345 (4.09); 3.6305 (1.81); 3.3844 (0.56); 3.3781 (0.34); 3.3717 (0.62); 3.3654 (1.17); 3.3590 (0.65); 3.3526 (0.40); 3.3463 (0.61); 3.3401 (0.36); 3.3188 (83.66); 3.2697 (0.51); 3.2545 (2.10); 3.2430 (1.81); 3.2303 (0.59); 3.2261 (1.89); 3.2145 (1.53); 2.8372 (0.48); 2.8168 (0.86); 2.7989 (0.49); 2.6162 (0.34); 2.6131 (0.51); 2.6102 (0.37); 2.5224 (0.87); 2.5194 (1.10); 2.5163 (1.02); 2.5074 (23.48); 2.5044 (53.22); 2.5014 (75.43); 2.4984 (54.67); 2.4954 (25.33); 2.3887 (0.34); 2.3856 (0.49); 2.3826 (0.36); 2.1853 (16.00); 2.1700 (0.43); 2.1154 (0.59); 2.0879 (0.88); 2.0601 (0.65); 1.9884 (4.41); 1.7835 (0.53); 1.7779 (0.58); 1.7633 (0.55); 1.7572 (0.54); 1.5559 (0.55); 1.5496 (0.60); 1.5358 (0.57); 1.5295 (0.54); 1.3359 (0.43); 1.2588 (0.34); 1.2497 (0.56); 1.1870 (1.23); 1.1751 (2.46); 1.1633 (1.19); 0.0052 (1.80); −0.0002 (65.36); −0.0058 (2.16);

Ex. 21, Solvent: DMSO, Spectrometer: 399.95 MHz 8.3164 (0.44); 7.9600 (8.55); 7.3175 (3.41); 7.3128 (4.35); 7.2756 (4.09); 7.2709 (3.55); 7.0001 (1.52); 6.8629 (3.61); 6.7258 (1.69); 6.2950 (3.72); 6.1875 (1.31); 6.1633 (1.68); 6.1568 (1.59); 6.1324 (1.36); 5.7567 (11.60); 5.2624 (0.81); 5.2202 (2.75); 5.1767 (2.65); 5.1344 (0.80); 4.8983 (0.34); 4.8920 (0.36); 4.8581 (2.93); 4.8500 (3.96); 4.8434 (2.94); 4.8094 (0.35); 4.8036 (0.37); 4.3907 (0.77); 4.3577 (0.81); 4.0374 (0.66); 4.0195 (1.15); 4.0022 (0.65); 3.9783 (0.79); 3.7710 (1.02); 3.7399 (1.26); 3.7287 (1.71); 3.6977 (1.38); 3.5613 (1.55); 3.5370 (1.55); 3.5191 (1.13); 3.4949 (1.14); 3.4743 (1.69); 3.4685 (3.90); 3.4627 (1.72); 3.4108 (0.56); 3.4015 (0.45); 3.3911 (0.69); 3.3820 (1.22); 3.3725 (0.78); 3.3628 (0.64); 3.3258 (206.04); 3.3006 (0.81); 3.2947 (0.77); 3.2641 (1.06); 3.2355 (0.57); 2.8630 (0.55); 2.8332 (0.98); 2.8054 (0.54); 2.6753 (0.82); 2.6708 (1.17); 2.6663 (0.88); 2.5236 (6.05); 2.5106 (61.29); 2.5062 (121.93); 2.5017 (162.84); 2.4972 (123.45); 2.4930 (63.26); 2.3374 (0.43); 2.3329 (0.86); 2.3285 (1.16); 2.3240 (0.88); 2.1878 (16.00); 2.1455 (0.75); 2.1151 (1.49); 2.0825 (0.81); 1.9887 (2.69); 1.7973 (0.64); 1.7738 (0.59); 1.5841 (0.59); 1.5759 (0.65); 1.5544 (0.62); 1.5458 (0.58); 1.3354 (0.34); 1.2981 (0.40); 1.2586 (0.57); 1.2493 (0.45); 1.2332 (0.51); 1.1925 (0.74); 1.1747 (1.43); 1.1569 (0.71); 0.1460 (0.49); 0.0159 (0.96); 0.0079 (4.30); −0.0002 (106.55); −0.0083 (4.46); −0.1498 (0.50);

Ex. 22, Solvent: DMSO, Spectrometer: 601.6 MHz 8.3142 (0.34); 7.9946 (7.84); 7.1678 (2.89); 7.1549 (3.09); 6.9506 (1.27); 6.8763 (3.42); 6.8594 (3.09); 6.7684 (3.08); 6.7568 (1.77); 6.2920 (3.60); 6.0513 (0.42); 6.0431 (0.92); 6.0340 (0.71); 6.0254 (0.99); 6.0226 (0.56); 6.0170 (0.53); 6.0143 (1.04); 6.0053 (0.74); 5.9966 (1.03); 5.9884 (0.49); 5.8617 (1.21); 5.8495 (1.34); 5.8433 (1.28); 5.8310 (1.21); 5.7546

(5.26); 5.4194 (0.67); 5.4167 (1.81); 5.4138 (1.84); 5.4110 (0.69); 5.3879 (1.61); 5.3850 (1.63); 5.3822 (0.61); 5.2475 (1.04); 5.2255 (1.92); 5.2228 (2.29); 5.2197 (2.66); 5.2079 (1.69); 5.2053 (1.70); 5.1630 (2.28); 5.1348 (1.00); 4.6045 (1.74); 4.5967 (3.07); 4.5888 (1.72); 4.5750 (0.34); 4.3765 (0.70); 4.3542 (0.74); 4.0348 (0.33); 4.0230 (0.35); 3.9958 (0.66); 3.9733 (0.72); 3.8315 (1.31); 3.8130 (1.54); 3.8032 (1.64); 3.7847 (1.38); 3.7377 (0.60); 3.3858 (0.59); 3.3795 (0.38); 3.3729 (0.67); 3.3666 (1.18); 3.3605 (0.69); 3.3536 (0.45); 3.3475 (0.71); 3.3222 (44.05); 3.3190 (116.77); 3.2722 (0.53); 3.2596 (1.82); 3.2475 (2.02); 3.2313 (1.88); 3.2191 (1.46); 2.8397 (0.50); 2.8194 (0.91); 2.8017 (0.50); 2.6159 (0.57); 2.6129 (0.82); 2.6098 (0.57); 2.5222 (1.54); 2.5191 (1.95); 2.5160 (1.99); 2.5071 (40.12); 2.5042 (87.09); 2.5011 (121.31); 2.4981 (87.79); 2.4951 (40.80); 2.3885 (0.58); 2.3853 (0.79); 2.3822 (0.55); 2.2873 (14.22); 2.1847 (16.00); 2.1701 (0.64); 2.1169 (0.68); 2.0884 (0.99); 2.0612 (0.69); 1.9883 (1.39); 1.7829 (0.56); 1.7775 (0.60); 1.7631 (0.57); 1.7575 (0.52); 1.5568 (0.55); 1.5504 (0.59); 1.5360 (0.55); 1.5300 (0.54); 1.2586 (0.33); 1.2494 (0.42); 1.2351 (0.37); 1.1867 (0.40); 1.1748 (0.77); 1.1630 (0.39); 1.1387 (0.54); 0.0840 (0.56); 0.0704 (0.41); 0.0052 (0.60); −0.0002 (18.89); −0.0057 (0.67);

Ex. 23, Solvent: DMSO, Spectrometer: 600.13 MHz 8.3129 (0.35); 7.9980 (8.12); 7.1849 (2.82); 7.1720 (3.04); 6.9642 (3.46); 6.9516 (1.32); 6.8602 (3.12); 6.8177 (1.81); 6.8048 (1.77); 6.7688 (1.43); 6.2935 (3.75); 5.8333 (1.17); 5.8212 (1.30); 5.8150 (1.26); 5.8027 (1.20); 5.7541 (9.04); 5.2463 (0.99); 5.2179 (2.31); 5.1632 (2.30); 5.1350 (1.00); 4.8484 (6.15); 4.8445 (6.19); 4.3766 (0.70); 4.3548 (0.73); 4.0350 (0.63); 4.0232 (0.64); 3.9961 (0.66); 3.9727 (0.71); 3.8409 (1.23); 3.8224 (1.43); 3.8124 (1.51); 3.7940 (1.30); 3.5695 (1.85); 3.5656 (3.91); 3.5617 (1.77); 3.3964 (0.35); 3.3923 (0.56); 3.3852 (0.84); 3.3793 (0.75); 3.3719 (1.08); 3.3667 (1.90); 3.3611 (1.61); 3.3534 (2.07); 3.3324 (1876.28); 3.3130 (1.81); 3.3099 (1.34); 3.3001 (0.44); 3.2903 (0.39); 3.2756 (0.58); 3.2711 (0.58); 3.2515 (1.06); 3.2438 (1.67); 3.2315 (2.00); 3.2152 (1.45); 3.2031 (1.41); 2.8391 (0.48); 2.8184 (0.91); 2.8009 (0.50); 2.6199 (0.75); 2.6170 (1.59); 2.6140 (2.18); 2.6110 (1.56); 2.6080 (0.72); 2.5412 (0.38); 2.5230 (3.90); 2.5199 (4.77); 2.5168 (4.61); 2.5079 (123.47); 2.5050 (264.64); 2.5019 (362.99); 2.4989 (259.62); 2.4960 (118.63); 2.3888 (1.53); 2.3858 (2.11); 2.3828 (1.48); 2.3007 (13.79); 2.1852 (16.00); 2.1711 (0.66); 2.1187 (0.61); 2.0909 (0.94); 2.0644 (0.69); 1.9885 (2.71); 1.7854 (0.55); 1.7792 (0.58); 1.7644 (0.57); 1.7587 (0.53); 1.5569 (0.56); 1.5507 (0.61); 1.5363 (0.57); 1.5305 (0.56); 1.3354 (0.58); 1.2981 (0.40); 1.2586 (0.54); 1.2494 (0.71); 1.1867 (0.75); 1.1748 (1.46); 1.1630 (0.72); 0.0969 (0.58); 0.0053 (4.51); −0.0001 (144.35); −0.0057 (4.44); −0.1002 (0.61);

Ex. 24, Solvent: DMSO, Spectrometer: 399.95 MHz 7.9487 (9.14); 7.2585 (3.72); 7.2537 (4.34); 7.2009 (3.95); 7.1961 (3.40); 7.0001 (1.54); 6.8629 (3.75); 6.7258 (1.74); 6.2956 (3.55); 6.2149 (1.35); 6.1918 (1.71); 6.1839 (1.57); 6.1607 (1.42); 5.7985 (0.35); 5.7847 (0.74); 5.7717 (0.69); 5.7574 (14.11); 5.7415 (0.99); 5.7283 (0.83); 5.7152 (0.96); 5.7015 (0.48); 5.2670 (1.27); 5.2629 (2.06); 5.2589 (1.98); 5.2552 (0.77); 5.2269 (2.61); 5.2196 (1.95); 5.2156 (1.76); 5.2119 (0.71); 5.1747 (2.44); 5.1324 (0.84); 5.0184 (1.75); 5.0150 (1.72); 4.9921 (1.62); 4.9887 (1.61); 4.6251 (0.50); 4.6117 (0.52); 4.5934 (1.42); 4.5800 (1.39); 4.5623 (1.42); 4.5481 (1.38); 4.5305 (0.54); 4.5162 (0.50); 4.3903 (0.70); 4.3565 (0.74); 4.0375 (0.76); 4.0196 (1.20); 4.0021 (0.60); 3.9793 (0.72); 3.7660 (1.06); 3.7348 (1.32); 3.7238 (1.78); 3.6927 (1.43); 3.5552 (1.55); 3.5320 (1.56); 3.5130 (1.14); 3.4899 (1.13); 3.4182 (0.50); 3.4088 (0.34); 3.3989 (0.59); 3.3896 (1.07); 3.3802 (0.60); 3.3707 (0.38); 3.3608 (0.60); 3.3509 (0.37); 3.3264 (87.67); 3.2992 (0.64); 3.2682 (0.96); 3.2394 (0.52); 2.8672 (0.49); 2.8375 (0.88); 2.8104 (0.50); 2.6753 (0.41); 2.6707 (0.57); 2.6662 (0.41); 2.5242 (1.47); 2.5193 (2.32); 2.5108 (31.82); 2.5063 (63.80); 2.5017 (83.72); 2.4971 (60.62); 2.4926 (28.73); 2.3331 (0.43); 2.3285 (0.59); 2.3238 (0.42); 2.1880 (16.00); 2.1385 (0.65); 2.1047 (1.35); 2.0757 (0.75); 1.9889 (3.17); 1.8040 (0.56); 1.7956 (0.60); 1.7732 (0.58); 1.7656 (0.53); 1.5815 (0.56); 1.5726 (0.61); 1.5505 (0.58); 1.5420 (0.56); 1.3356 (0.49); 1.2584 (0.42); 1.2492 (0.63); 1.2338 (0.37); 1.1924 (0.89); 1.1746 (1.72); 1.1568 (0.85); 1.1382 (0.62); 0.0079 (1.93); −0.0002 (59.95); −0.0085 (1.93);

Ex. 25, Solvent: DMSO, Spectrometer: 399.95 MHz 8.0279 (3.87); 7.9601 (9.47); 7.3975 (0.92); 7.3802 (1.19); 7.3765 (1.97); 7.3594 (2.01); 7.3557 (1.30); 7.3385 (1.02); 7.0489 (2.67); 7.0297 (3.22); 6.9979 (3.52); 6.9363 (2.80); 6.9151 (2.60); 6.8606 (2.26); 6.8413 (3.43); 6.8191 (1.39); 6.1066 (1.31); 6.0846 (1.60); 6.0760 (1.51); 6.0540 (1.37); 5.9311 (0.45); 5.9178 (0.95); 5.9047 (0.93); 5.8915 (1.12); 5.8882 (0.67); 5.8782 (0.65); 5.8747 (1.25); 5.8615 (1.08); 5.8482 (1.20); 5.8352 (0.57); 5.7593 (6.99); 5.3448 (0.79); 5.3410 (2.09); 5.3369 (2.15); 5.3330 (0.85); 5.2977 (1.81); 5.2936 (1.86); 5.2898 (0.74); 5.1204 (2.05); 5.1168 (2.04); 5.0941 (1.91); 5.0904 (1.92); 4.6232 (0.44); 4.6102 (0.41); 4.5907 (2.08); 4.5780 (3.26); 4.5707 (1.59); 4.5669 (1.99); 4.5480 (0.36); 4.5344 (0.33); 4.1790 (1.94); 4.1451 (2.08); 4.1246 (0.54); 4.1109 (1.03); 4.1069 (0.47); 4.0195 (0.32); 3.8018 (0.92); 3.7708 (1.07); 3.7589 (1.35); 3.7289 (1.23); 3.5378 (1.52); 3.5157 (1.59); 3.5033 (0.37); 3.4946 (1.62); 3.4734 (1.16); 3.3594 (0.67); 3.3299 (55.60); 3.3119 (0.73); 3.3021 (0.80); 3.2932 (0.41); 3.0164 (1.33); 2.9868 (2.49); 2.9582 (1.39); 2.6708 (0.39); 2.5240 (1.44); 2.5105 (23.49); 2.5062 (46.51); 2.5017 (60.90); 2.4971 (44.34); 2.4928 (21.71); 2.3331 (0.33); 2.3284 (0.42); 2.3240 (0.32); 2.2329 (16.00); 2.1107 (15.92); 2.0623 (1.95); 1.9891 (1.38); 1.7104 (0.55); 1.7005 (0.69); 1.6794 (1.45); 1.6707 (1.63); 1.6485 (1.53); 1.6407 (1.42); 1.6187 (0.63); 1.6094 (0.50); 1.2152 (0.41); 1.1974 (0.79); 1.1920 (0.42); 1.1795 (0.40); 1.1742 (0.75); 1.1564 (0.39); 1.0734 (0.43); 1.0561 (0.43); −0.0002 (1.81);

Ex. 26, Solvent: DMSO, Spectrometer: 399.95 MHz 8.0044 (8.17); 7.1884 (2.93); 7.1691 (3.29); 6.9645 (3.82); 6.8199 (2.03); 6.8005 (1.84); 6.4986 (4.42);

5.8416 (1.17); 5.8235 (1.36); 5.8141 (1.34); 5.7957 (1.22); 5.7589 (1.32); 5.3524 (0.97); 5.3098 (2.81); 5.2586 (2.78); 5.2160 (0.98); 4.8515 (6.30); 4.8457 (6.52); 4.3839 (0.79); 4.3506 (0.83); 4.0554 (0.99); 4.0376 (3.04); 4.0198 (3.09); 4.0020 (1.13); 3.9834 (0.74); 3.9487 (0.81); 3.8553 (1.21); 3.8275 (1.40); 3.8124 (1.59); 3.7847 (1.32); 3.5799 (1.54); 3.5741 (3.36); 3.5683 (1.55); 3.3983 (0.53); 3.3890 (0.37); 3.3788 (0.65); 3.3696 (1.11); 3.3605 (0.68); 3.3502 (0.45); 3.3406 (0.78); 3.3264 (27.97); 3.3027 (1.83); 3.2875 (0.62); 3.2541 (2.36); 3.2356 (1.71); 3.2111 (1.44); 3.1929 (1.37); 2.8556 (0.60); 2.8258 (0.99); 2.7983 (0.57); 2.5240 (0.54); 2.5104 (14.51); 2.5061 (30.55); 2.5016 (42.55); 2.4972 (32.69); 2.4931 (16.62); 2.3331 (0.34); 2.3283 (0.36); 2.3001 (13.88); 2.2054 (16.00); 2.1934 (1.03); 2.1257 (0.70); 2.0918 (1.50); 2.0643 (0.82); 1.9891 (12.98); 1.8182 (0.63); 1.8094 (0.68); 1.7873 (0.62); 1.7788 (0.58); 1.5707 (0.60); 1.5614 (0.67); 1.5404 (0.63); 1.5310 (0.61); 1.3972 (0.35); 1.2582 (0.37); 1.1922 (3.50); 1.1744 (6.96); 1.1566 (3.45); 0.0080 (0.98); −0.0002 (31.85); −0.0084 (1.34);

Ex. 27, Solvent: DMSO, Spectrometer: 600.13 MHz 7.9752 (5.68); 7.1878 (2.27); 7.1737 (2.38); 6.9533 (0.98); 6.8618 (2.31); 6.7705 (1.08); 6.5563 (2.43); 6.5524 (2.73); 6.5035 (1.49); 6.4997 (1.31); 6.4895 (1.43); 6.4856 (1.29); 6.2946 (2.97); 5.7876 (0.95); 5.7750 (1.07); 5.7689 (1.05); 5.7561 (0.99); 5.2512 (0.82); 5.2229 (1.82); 5.1646 (1.72); 5.1363 (0.80); 4.3757 (0.58); 4.3538 (0.62); 4.0472 (0.33); 4.0353 (0.98); 4.0234 (1.01); 4.0115 (0.42); 3.9985 (0.58); 3.9781 (0.66); 3.8896 (0.83); 3.8784 (0.88); 3.8726 (1.31); 3.8614 (1.28); 3.8251 (0.53); 3.8178 (1.20); 3.8059 (1.26); 3.8008 (0.88); 3.7889 (0.83); 3.7765 (0.42); 3.7713 (0.94); 3.7523 (1.13); 3.7426 (2.44); 3.7381 (16.00); 3.7241 (1.06); 3.3894 (0.46); 3.3831 (0.34); 3.3766 (0.55); 3.3703 (0.93); 3.3640 (0.57); 3.3550 (1.29); 3.3423 (1.27); 3.3254 (75.46); 3.3141 (1.28); 3.2785 (0.47); 3.2587 (0.83); 3.2393 (0.45); 2.8902 (2.01); 2.8476 (0.43); 2.8276 (0.75); 2.8094 (0.44); 2.7313 (1.69); 2.5226 (0.40); 2.5196 (0.50); 2.5164 (0.55); 2.5046 (24.76); 2.5016 (33.47); 2.4987 (24.64); 2.1971 (0.62); 2.1869 (11.90); 2.1769 (0.73); 2.1141 (0.58); 2.0870 (0.88); 2.0616 (0.61); 1.9888 (4.15); 1.7792 (0.49); 1.7767 (0.49); 1.7618 (0.46); 1.7564 (0.43); 1.5543 (0.49); 1.5344 (0.46); 1.3971 (1.43); 1.1867 (1.12); 1.1748 (2.20); 1.1629 (1.09); 1.1303 (0.48); 1.1266 (0.45); 1.1186 (0.74); 1.1106 (0.48); 1.1069 (0.50); 0.4787 (0.33); 0.4766 (0.35); 0.4704 (0.57); 0.4684 (0.53); 0.4629 (0.74); 0.4573 (0.64); 0.4508 (0.44); 0.4483 (0.49); 0.4445 (0.38); 0.3860 (0.37); 0.3824 (0.50); 0.3806 (0.50); 0.3766 (0.47); 0.3735 (0.54); 0.3672 (0.75); 0.3604 (0.58); 0.3524 (0.38); 0.3467 (0.37); 0.2926 (0.41); 0.2853 (0.67); 0.2771 (1.19); 0.2721 (1.47); 0.2688 (1.34); 0.2649 (1.55); 0.2602 (1.06); 0.2519 (0.61); 0.2448 (0.36); 0.0053 (0.32); −0.0001 (7.89);

Ex. 28, Solvent: DMSO, Spectrometer: 399.95 MHz 7.9638 (7.36); 7.3700 (0.76); 7.3492 (1.67); 7.3319 (1.71); 7.3111 (0.82); 7.0001 (1.52); 6.8633 (4.36); 6.8462 (2.41); 6.8378 (1.50); 6.8131 (1.71); 6.7911 (1.22); 6.7259 (1.68); 6.2950 (3.99); 6.0878 (1.17); 6.0666 (1.43); 6.0570 (1.34); 6.0360 (1.20); 5.2707 (0.96); 5.2284 (2.60); 5.1725 (2.60); 5.1300 (0.96); 4.3861 (0.85); 4.3540 (0.91); 4.0552 (0.55); 4.0373 (1.66); 4.0195 (2.13); 4.0018 (1.14); 3.9758 (0.92); 3.9028 (1.21); 3.8858 (1.35); 3.8773 (1.72); 3.8606 (1.63); 3.7919 (0.92); 3.7547 (1.94); 3.7504 (1.87); 3.7364 (1.68); 3.7301 (1.42); 3.7187 (1.47); 3.7115 (1.31); 3.6042 (1.39); 3.5831 (1.39); 3.5620 (0.94); 3.5412 (1.00); 3.4136 (0.63); 3.4040 (0.49); 3.3938 (0.78); 3.3847 (1.22); 3.3754 (0.83); 3.3650 (0.65); 3.3556 (0.93); 3.3272 (76.50); 3.3019 (0.92); 3.2641 (1.16); 3.2353 (0.64); 2.8622 (0.60); 2.8337 (1.08); 2.8044 (0.62); 2.6754 (0.57); 2.6707 (0.75); 2.6665 (0.57); 2.5061 (82.21); 2.5017 (106.35); 2.4974 (80.71); 2.3331 (0.68); 2.3285 (0.80); 2.3241 (0.62); 2.1873 (16.00); 2.1616 (0.34); 2.1234 (0.87); 2.0923 (1.72); 2.0629 (0.98); 1.9890 (6.69); 1.8252 (0.35); 1.8156 (0.36); 1.7896 (0.95); 1.7628 (0.71); 1.7556 (0.67); 1.7450 (0.44); 1.5902 (0.34); 1.5619 (0.70); 1.5334 (0.66); 1.1924 (1.85); 1.1746 (3.58); 1.1567 (1.78); 1.0251 (0.36); 1.0100 (0.71); 0.9934 (0.97); 0.9767 (0.83); 0.9598 (0.43); 0.3804 (0.36); 0.3721 (0.52); 0.3545 (0.94); 0.3450 (1.17); 0.3397 (0.98); 0.3306 (0.59); 0.3261 (0.66); 0.3208 (0.53); 0.2060 (0.47); 0.1965 (0.59); 0.1787 (2.77); 0.1712 (2.46); 0.1613 (4.41); 0.1471 (1.81); 0.1306 (0.69); 0.1239 (0.52); −0.0002 (18.65);

Ex. 29, Solvent: DMSO, Spectrometer: 399.95 MHz 8.0135 (7.84); 7.3476 (0.67); 7.3434 (0.92); 7.3236 (4.06); 7.3047 (3.74); 7.2072 (1.33); 7.1516 (2.20); 7.1317 (1.88); 7.0725 (2.95); 7.0206 (1.25); 7.0019 (2.21); 6.9833 (1.03); 6.9380 (1.52); 6.3834 (3.20); 5.8869 (1.10); 5.8691 (1.27); 5.8593 (1.24); 5.8414 (1.13); 5.7569 (7.59); 5.2407 (0.62); 5.1983 (2.49); 5.1598 (2.44); 5.1435 (0.40); 5.1174 (0.61); 4.8819 (6.04); 4.8760 (5.98); 4.3626 (0.64); 4.3296 (0.68); 4.0378 (0.65); 4.0200 (0.68); 4.0021 (0.48); 3.9904 (0.61); 3.9553 (0.67); 3.8993 (1.18); 3.8714 (1.36); 3.8563 (1.52); 3.8286 (1.27); 3.5890 (1.60); 3.5831 (3.49); 3.5772 (1.54); 3.3906 (3.30); 3.3733 (1.28); 3.3630 (1.26); 3.3537 (0.71); 3.3437 (0.44); 3.3342 (0.58); 3.2694 (1.85); 3.2515 (1.58); 3.2327 (0.95); 3.2266 (1.72); 3.2086 (1.62); 2.8326 (0.45); 2.8049 (0.82); 2.7747 (0.46); 2.5235 (0.47); 2.5103 (10.63); 2.5059 (21.60); 2.5013 (28.45); 2.4968 (20.20); 2.4923 (9.50); 2.1611 (16.00); 2.1079 (0.61); 2.0790 (1.27); 2.0498 (0.70); 1.9888 (2.84); 1.7766 (0.52); 1.7681 (0.55); 1.7455 (0.52); 1.7377 (0.48); 1.5600 (0.52); 1.5504 (0.56); 1.5287 (0.52); 1.5202 (0.50); 1.1922 (0.79); 1.1744 (1.56); 1.1566 (0.77); −0.0002 (2.27);

Ex. 30, Solvent: DMSO, Spectrometer: 399.95 MHz 8.0106 (9.66); 7.3122 (1.38); 7.3070 (1.86); 7.3034 (1.80); 7.2943 (2.51); 7.2886 (2.37); 7.2843 (2.01); 7.2764 (1.66); 7.2723 (0.83); 7.0618 (2.49); 7.0508 (0.46); 7.0417 (1.89); 6.9745 (1.36); 6.9548 (2.36); 6.9377 (1.12); 6.4962 (4.47); 6.0804 (0.43); 6.0677 (0.97); 6.0547 (0.71); 6.0413 (1.09); 6.0370 (0.58); 6.0288 (0.60); 6.0245 (1.18); 6.0115 (0.82); 5.9980 (1.18); 5.9855 (0.55); 5.9178 (1.18); 5.8999 (1.37); 5.8903 (1.39); 5.8721 (1.23); 5.7554 (3.77); 5.4426

(0.62); 5.4384 (1.88); 5.4341 (1.98); 5.4300 (0.73); 5.3993 (0.58); 5.3952 (1.62); 5.3909 (1.68); 5.3871 (0.62); 5.3490 (0.87); 5.3064 (2.59); 5.2534 (2.66); 5.2461 (2.16); 5.2420 (2.00); 5.2195 (1.83); 5.2153 (2.05); 5.2117 (1.56); 4.6321 (2.51); 4.6276 (2.73); 4.6198 (2.65); 4.6153 (2.44); 4.3814 (0.71); 4.3488 (0.71); 4.0557 (0.89); 4.0380 (2.66); 4.0202 (2.74); 4.0024 (1.04); 3.9835 (0.69); 3.9517 (0.73); 3.8909 (1.34); 3.8629 (1.47); 3.8482 (1.72); 3.8203 (1.43); 3.3995 (0.56); 3.3894 (0.39); 3.3797 (0.67); 3.3702 (1.17); 3.3609 (0.78); 3.3268 (115.28); 3.3247 (244.25); 3.3015 (0.91); 3.2864 (2.05); 3.2682 (2.05); 3.2607 (1.05); 3.2435 (1.55); 3.2256 (1.84); 2.8595 (0.57); 2.8298 (0.90); 2.7999 (0.55); 2.6748 (0.44); 2.6703 (0.54); 2.6664 (0.41); 2.5237 (0.95); 2.5058 (64.08); 2.5015 (86.96); 2.4974 (61.07); 2.3329 (0.35); 2.3282 (0.54); 2.2059 (16.00); 2.1941 (0.82); 2.1281 (0.63); 2.0918 (1.32); 2.0736 (0.76); 2.0642 (0.77); 1.9885 (11.91); 1.8144 (0.55); 1.8073 (0.61); 1.7843 (0.55); 1.7789 (0.51); 1.5723 (0.55); 1.5625 (0.61); 1.5404 (0.55); 1.5319 (0.53); 1.2345 (0.56); 1.1924 (3.16); 1.1746 (6.25); 1.1568 (3.04); 0.0079 (0.33); −0.0002 (11.83); −0.0085 (0.37);

Ex. 31, Solvent: DMSO, Spectrometer: 399.95 MHz 8.3169 (0.34); 7.9747 (8.93); 7.9522 (0.97); 7.4350 (0.80); 7.4180 (1.07); 7.4139 (1.72); 7.3971 (1.75); 7.3930 (1.11); 7.3762 (0.89); 7.0110 (2.57); 7.0008 (1.74); 6.9899 (2.33); 6.9122 (1.26); 6.8907 (1.42); 6.8870 (1.50); 6.8637 (4.65); 6.7266 (1.72); 6.2950 (3.82); 6.0724 (1.10); 6.0500 (1.32); 6.0419 (1.26); 6.0194 (1.13); 5.2657 (0.82); 5.2232 (2.61); 5.1774 (2.57); 5.1348 (0.81); 4.8525 (3.55); 4.8470 (6.21); 4.8414 (3.66); 4.3937 (0.74); 4.3602 (0.80); 4.0551 (0.76); 4.0373 (2.39); 4.0195 (2.94); 4.0018 (1.14); 3.9812 (0.77); 3.8099 (0.72); 3.7790 (0.84); 3.7698 (0.99); 3.7669 (1.02); 3.7372 (0.91); 3.5476 (1.82); 3.5417 (4.04); 3.5358 (1.85); 3.5253 (1.31); 3.5026 (1.25); 3.4824 (0.95); 3.4600 (0.95); 3.4161 (0.53); 3.4070 (0.38); 3.3965 (0.62); 3.3873 (1.11); 3.3783 (0.68); 3.3685 (0.47); 3.3585 (0.75); 3.3498 (0.69); 3.3283 (104.73); 3.2962 (0.61); 3.2647 (0.99); 3.2365 (0.56); 2.8903 (8.29); 2.8628 (0.53); 2.8318 (0.94); 2.8049 (0.53); 2.7307 (6.62); 2.6753 (0.50); 2.6709 (0.72); 2.6662 (0.52); 2.5406 (0.38); 2.5384 (0.40); 2.5241 (2.78); 2.5193 (4.33); 2.5107 (39.51); 2.5063 (79.45); 2.5018 (104.79); 2.4972 (76.32); 2.4928 (37.44); 2.3332 (0.55); 2.3286 (0.74); 2.3241 (0.57); 2.1883 (16.00); 2.1484 (0.75); 2.1130 (1.45); 2.0836 (0.83); 1.9888 (10.32); 1.8011 (0.62); 1.7797 (0.58); 1.5861 (0.59); 1.5773 (0.65); 1.5554 (0.62); 1.5467 (0.60); 1.3974 (2.06); 1.1925 (2.75); 1.1747 (5.55); 1.1569 (2.69); 0.0079 (0.70); −0.0002 (20.09); −0.0085 (0.85);

Ex. 32, Solvent: DMSO, Spectrometer: 399.95 MHz 8.0176 (3.53); 7.6012 (1.82); 7.3438 (0.44); 7.3239 (1.89); 7.3050 (1.73); 7.1513 (1.01); 7.1313 (0.86); 7.0203 (0.58); 7.0018 (1.01); 6.9830 (0.46); 5.8875 (0.50); 5.8696 (0.59); 5.8598 (0.57); 5.8420 (0.53); 5.6352 (0.42); 5.5923 (0.93); 5.5228 (0.92); 5.4798 (0.41); 4.8815 (2.80); 4.8756 (2.78); 4.3512 (0.34); 4.3165 (0.35); 3.9344 (0.35); 3.9003 (0.52); 3.8724 (0.60); 3.8573 (0.67); 3.8295 (0.57); 3.5881 (0.71); 3.5822 (1.50); 3.5764 (0.68); 3.3790 (0.49); 3.3500 (0.35); 3.3277 (40.02); 3.2700 (1.02); 3.2523 (0.72); 3.2272 (0.67); 3.2094 (0.60); 2.8910 (2.35); 2.8506 (0.43); 2.7317 (1.82); 2.6713 (0.43); 2.5246 (1.46); 2.5198 (2.36); 2.5112 (24.23); 2.5068 (48.55); 2.5023 (63.46); 2.4977 (45.99); 2.4933 (22.44); 2.3289 (0.43); 2.0945 (0.63); 2.0639 (0.35); 1.3977 (16.00); −0.0002 (1.78);

Ex. 33, Solvent: DMSO, Spectrometer: 399.95 MHz 8.3173 (0.68); 8.0139 (16.00); 7.6009 (9.09); 7.3088 (4.66); 7.3047 (4.26); 7.2943 (5.83); 7.2901 (6.33); 7.2765 (3.38); 7.0614 (5.55); 7.0397 (4.29); 6.9733 (3.12); 6.9546 (5.42); 6.9358 (2.50); 6.0796 (0.81); 6.0671 (1.68); 6.0536 (1.40); 6.0405 (1.96); 6.0366 (1.26); 6.0280 (1.17); 6.0238 (2.13); 6.0105 (1.61); 5.9973 (2.06); 5.9849 (1.00); 5.9180 (2.65); 5.9001 (3.04); 5.8902 (3.03); 5.8722 (2.72); 5.6336 (2.15); 5.5908 (4.85); 5.5228 (4.85); 5.4798 (2.17); 5.4387 (3.78); 5.4344 (3.96); 5.4155 (0.38); 5.3954 (3.29); 5.3911 (3.43); 5.3759 (0.33); 5.2445 (3.75); 5.2407 (3.86); 5.2180 (3.49); 5.2142 (3.58); 4.6664 (0.38); 4.6541 (0.44); 4.6318 (5.77); 4.6274 (6.54); 4.6202 (6.39); 4.6156 (5.84); 4.5935 (0.50); 4.5812 (0.41); 4.3499 (1.84); 4.3167 (1.94); 3.9705 (1.72); 3.9352 (1.91); 3.8923 (2.66); 3.8643 (2.99); 3.8494 (3.43); 3.8215 (2.94); 3.4082 (1.20); 3.3989 (0.91); 3.3887 (1.47); 3.3795 (2.48); 3.3704 (1.57); 3.3599 (1.12); 3.3504 (1.69); 3.3269 (87.89); 3.3030 (7.09); 3.2871 (3.80); 3.2691 (5.63); 3.2441 (3.72); 3.2264 (3.21); 2.8786 (1.28); 2.8514 (2.32); 2.8211 (1.31); 2.6757 (0.86); 2.6713 (1.15); 2.6670 (0.87); 2.5414 (0.76); 2.5066 (123.19); 2.5022 (163.13); 2.4979 (124.07); 2.3335 (0.90); 2.3290 (1.20); 2.3248 (0.94); 2.1240 (1.68); 2.0916 (3.54); 2.0619 (1.97); 1.9891 (0.84); 1.8341 (0.60); 1.8240 (0.72); 1.8030 (1.46); 1.7945 (1.59); 1.7721 (1.44); 1.7641 (1.35); 1.7424 (0.61); 1.7329 (0.47); 1.5797 (0.59); 1.5699 (0.72); 1.5492 (1.44); 1.5399 (1.58); 1.5186 (1.47); 1.5092 (1.41); 1.4889 (0.62); 1.4785 (0.50); 1.3976 (8.31); 1.3512 (0.60); 1.3361 (1.33); 1.2587 (0.34); 1.2495 (0.99); 1.2251 (1.13); 1.1750 (0.46); 0.1460 (0.57); 0.0079 (5.94); −0.0002 (128.33); −0.0083 (6.23); −0.1496 (0.60);

Ex. 34, Solvent: CD3CN, Spectrometer: 399.95 MHz 7.7083 (6.06); 7.5436 (1.24); 7.5244 (2.00); 7.4725 (0.75); 7.4677 (0.83); 7.4555 (1.21); 7.4509 (1.48); 7.4360 (0.76); 7.4314 (1.48); 7.4274 (1.02); 7.4129 (2.75); 7.4081 (1.86); 7.4023 (2.05); 7.3989 (1.79); 7.3852 (1.24); 7.3825 (1.31); 7.3662 (0.41); 7.3628 (0.37); 6.3912 (3.38); 6.0855 (1.21); 6.0633 (1.45); 6.0581 (1.40); 6.0359 (1.26); 5.4478 (5.74); 5.1282 (0.63); 5.0861 (3.18); 5.0549 (3.16); 5.0129 (0.64); 4.5808 (1.36); 4.5455 (2.82); 4.4959 (0.73); 4.4847 (3.37); 4.4639 (0.73); 4.4494 (1.65); 3.9738 (1.43); 3.9462 (2.02); 3.9303 (1.85); 3.9137 (0.75); 3.9028 (1.91); 3.3696 (0.71); 3.3643 (1.81); 3.3508 (0.73); 3.3420 (2.72); 3.3317 (0.72); 3.3208 (1.99); 3.3123 (1.18); 3.2988 (1.58); 3.2815 (0.95); 3.2526 (0.53); 3.2460 (0.49); 2.9728 (0.42); 2.9425 (16.00); 2.8825 (0.46); 2.8759 (0.51); 2.8498 (0.86); 2.8452 (0.88);

2.8188 (0.51); 2.8123 (0.47); 2.2256 (16.31); 2.1817 (12.52); 2.1786 (12.84); 2.1203 (0.72); 1.9638 (0.83); 1.9575 (0.80); 1.9519 (5.16); 1.9457 (9.51); 1.9396 (13.00); 1.9333 (8.89); 1.9272 (4.50); 1.8732 (0.60); 1.8635 (0.62); 1.8421 (0.57); 1.8324 (0.55); 1.7053 (0.63); 1.6953 (0.64); 1.6740 (0.59); 1.6643 (0.56); −0.0002 (3.21);

Ex. 35, Solvent: CD3CN, Spectrometer: 399.95 MHz 7.7009 (3.52); 7.6949 (4.85); 7.5121 (1.27); 7.5082 (1.60); 7.4918 (2.04); 7.4223 (0.34); 7.4175 (0.72); 7.4104 (0.57); 7.4006 (1.27); 7.3950 (1.13); 7.3861 (1.41); 7.3812 (1.44); 7.3763 (1.15); 7.3677 (2.28); 7.3640 (2.54); 7.3617 (1.79); 7.3585 (2.13); 7.3522 (2.26); 7.3487 (2.27); 7.3418 (1.45); 7.3377 (1.01); 7.3235 (0.47); 6.3904 (4.15); 6.0731 (0.94); 6.0512 (1.11); 6.0456 (1.19); 6.0237 (1.08); 6.0196 (0.87); 6.0142 (0.75); 5.9917 (0.66); 5.4467 (3.81); 5.1259 (0.73); 5.0839 (3.90); 5.0530 (3.81); 5.0317 (0.67); 5.0109 (0.74); 4.4964 (0.77); 4.4626 (0.80); 4.2284 (1.10); 4.1947 (1.44); 4.1428 (0.66); 4.1094 (3.41); 4.0957 (3.50); 4.0623 (0.68); 3.9871 (1.62); 3.9533 (1.80); 3.9362 (1.72); 3.9104 (1.93); 3.9087 (2.05); 3.8950 (1.38); 3.8929 (1.62); 3.8654 (1.49); 3.3778 (0.36); 3.3664 (1.37); 3.3556 (1.62); 3.3489 (0.89); 3.3437 (1.36); 3.3395 (1.57); 3.3337 (1.73); 3.3228 (1.26); 3.3121 (2.35); 3.3008 (1.28); 3.2903 (1.64); 3.2817 (1.12); 3.2527 (0.60); 3.2462 (0.56); 2.8823 (0.50); 2.8759 (0.55); 2.8456 (0.98); 2.8188 (0.56); 2.8124 (0.52); 2.5676 (16.00); 2.5203 (10.63); 2.2257 (18.95); 2.2113 (1.50); 2.2100 (1.47); 2.1508 (8.92); 2.1450 (7.66); 2.1193 (0.89); 2.1068 (0.44); 1.9635 (1.26); 1.9573 (1.46); 1.9516 (10.81); 1.9454 (20.09); 1.9392 (27.69); 1.9330 (18.99); 1.9268 (9.78); 1.9026 (0.38); 1.8925 (0.39); 1.8717 (0.71); 1.8624 (0.72); 1.8409 (0.66); 1.8313 (0.65); 1.7249 (0.36); 1.7047 (0.71); 1.6945 (0.74); 1.6736 (0.67); 1.6638 (0.65); −0.0002 (6.43);

Ex. 36, Solvent: CD3CN, Spectrometer: 399.95 MHz 7.6978 (9.56); 7.6946 (9.81); 7.5034 (2.47); 7.4953 (1.98); 7.4871 (3.22); 7.4786 (2.25); 7.4120 (1.37); 7.4058 (1.29); 7.4041 (1.31); 7.3961 (2.49); 7.3894 (3.75); 7.3832 (1.79); 7.3780 (2.98); 7.3709 (3.94); 7.3642 (5.25); 7.3592 (7.40); 7.3502 (4.68); 7.3463 (4.48); 7.3432 (4.31); 7.3389 (3.50); 7.3255 (0.77); 7.3199 (0.36); 6.3904 (9.09); 6.0559 (2.04); 6.0490 (1.54); 6.0337 (2.46); 6.0279 (3.38); 6.0213 (1.74); 6.0064 (2.11); 5.9989 (1.53); 5.4461 (6.12); 5.1259 (1.72); 5.0837 (8.68); 5.0527 (8.53); 5.0108 (1.70); 4.4966 (1.86); 4.4630 (1.92); 4.1672 (2.48); 4.1336 (3.50); 4.0704 (16.00); 3.9820 (3.65); 3.9483 (4.37); 3.9368 (3.21); 3.9335 (3.07); 3.9090 (4.03); 3.9059 (3.83); 3.8938 (2.76); 3.8900 (2.90); 3.8659 (2.47); 3.8624 (2.68); 3.3719 (4.90); 3.3580 (1.20); 3.3497 (5.82); 3.3392 (3.46); 3.3289 (5.33); 3.3192 (2.12); 3.3068 (4.84); 3.2814 (2.60); 3.2524 (1.42); 3.2458 (1.31); 2.8770 (1.70); 2.8581 (2.13); 2.8442 (3.34); 2.8396 (3.03); 2.8252 (3.07); 2.8203 (2.47); 2.8172 (2.63); 2.8064 (3.31); 2.8032 (2.20); 2.7871 (1.40); 2.7842 (1.81); 2.7653 (0.57); 2.7494 (0.72); 2.7307 (2.29); 2.7121 (2.41); 2.6978 (1.98); 2.6937 (0.98); 2.6795 (2.88); 2.6611 (2.11); 2.6468 (1.21); 2.6427 (0.66); 2.6283 (1.11); 2.6097 (0.36); 2.2254 (41.56); 2.2087 (1.66); 2.2029 (1.75); 2.1611 (2.89); 2.1390 (18.09); 2.1203 (2.04); 1.9630 (1.87); 1.9511 (16.20); 1.9450 (29.63); 1.9388 (40.14); 1.9327 (27.43); 1.9265 (14.03); 1.9023 (0.82); 1.8919 (0.82); 1.8718 (1.68); 1.8617 (1.74); 1.8404 (1.58); 1.8309 (1.54); 1.8101 (0.64); 1.7999 (0.57); 1.7351 (0.72); 1.7243 (0.80); 1.7045 (1.69); 1.6944 (1.75); 1.6737 (1.59); 1.6637 (1.55); 1.6429 (0.64); 1.6325 (0.58); 1.3112 (7.82); 1.2978 (7.09); 1.2924 (15.87); 1.2792 (12.26); 1.2737 (8.02); 1.2605 (5.50); 0.0078 (0.36); −0.0002 (8.65); −0.0086 (0.33);

Ex. 37, Solvent: DMSO, Spectrometer: 399.95 MHz 8.0640 (0.47); 7.9724 (5.06); 7.9511 (0.92); 7.3757 (0.61); 7.3547 (1.09); 7.3396 (1.18); 7.3184 (0.67); 7.0292 (1.63); 7.0201 (0.65); 7.0080 (1.47); 7.0004 (1.26); 6.8829 (1.40); 6.8633 (2.63); 6.8505 (0.94); 6.8289 (0.81); 6.7465 (0.55); 6.7262 (1.23); 6.3413 (1.14); 6.3002 (3.02); 5.3924 (0.49); 5.2614 (0.62); 5.2194 (1.88); 5.1719 (1.92); 5.1299 (0.63); 5.1053 (3.31); 4.9229 (3.83); 4.9172 (3.95); 4.3945 (0.59); 4.3594 (0.64); 4.2667 (0.94); 4.2556 (1.08); 4.2437 (1.05); 4.0560 (0.58); 4.0383 (1.66); 4.0204 (2.05); 4.0029 (0.99); 3.9777 (0.72); 3.7070 (1.48); 3.7025 (1.60); 3.6939 (2.25); 3.6801 (3.32); 3.6706 (2.57); 3.6521 (5.30); 3.5928 (2.49); 3.5858 (2.97); 3.3779 (5389.76); 2.8920 (7.63); 2.8662 (0.93); 2.8312 (1.23); 2.8031 (0.88); 2.7325 (6.18); 2.6785 (3.59); 2.6739 (4.83); 2.6694 (3.59); 2.5409 (3.16); 2.5272 (16.53); 2.5224 (24.16); 2.5137 (251.32); 2.5094 (502.31); 2.5049 (656.43); 2.5003 (472.57); 2.4960 (230.06); 2.3692 (1.31); 2.3360 (3.51); 2.3315 (4.73); 2.3269 (3.82); 2.2414 (5.87); 2.2071 (0.91); 2.1905 (12.67); 2.1730 (1.01); 2.1055 (1.36); 2.0721 (16.00); 1.9889 (6.86); 1.9101 (1.98); 1.7874 (0.66); 1.7687 (0.63); 1.6120 (1.12); 1.5918 (6.80); 1.5472 (0.60); 1.4104 (0.83); 1.2356 (0.72); 1.1928 (1.94); 1.1750 (3.75); 1.1572 (1.90); −0.0002 (2.02);

Ex. 38, Solvent: DMSO, Spectrometer: 399.95 MHz 8.0193 (3.81); 7.9536 (9.31); 7.9287 (0.71); 7.4111 (1.90); 7.3903 (3.70); 7.3699 (2.77); 7.1618 (3.41); 7.1554 (4.01); 7.1404 (2.83); 7.1355 (3.52); 7.0500 (2.52); 7.0308 (3.07); 6.9990 (3.46); 6.8590 (1.95); 6.8395 (1.66); 6.2332 (1.49); 6.2085 (1.94); 6.2024 (1.88); 6.1777 (1.58); 5.7531 (5.37); 4.8383 (0.39); 4.8325 (0.42); 4.7981 (3.37); 4.7912 (5.19); 4.7841 (3.81); 4.7499 (0.40); 4.7439 (0.43); 4.1809 (1.91); 4.1469 (2.02); 4.0379 (0.72); 4.0201 (0.75); 3.7672 (1.17); 3.7363 (1.43); 3.7251 (2.07); 3.6943 (1.70); 3.5841 (1.95); 3.5593 (1.99); 3.5420 (1.43); 3.5173 (1.40); 3.5040 (0.41); 3.4453 (2.54); 3.4396 (4.79); 3.4338 (2.75); 3.3583 (517.73); 3.3548 (636.88); 3.3514 (650.80); 3.3476 (856.85); 3.1850 (0.58); 3.1755 (0.57); 3.1584 (0.59); 3.1523 (0.69); 3.0153 (1.49); 2.9857 (2.67); 2.9568 (1.50); 2.9081 (0.89); 2.6766 (1.32); 2.6721 (1.80); 2.6676 (1.36); 2.5393 (1.01); 2.5254 (5.57); 2.5206 (8.48); 2.5119 (93.76); 2.5075 (189.89); 2.5030 (252.19); 2.4984 (187.91); 2.4941 (94.93); 2.3343 (1.28); 2.3297 (1.75); 2.3252 (1.31); 2.2726 (0.33); 2.2336 (15.38); 2.1124 (16.00); 2.0727 (3.08); 1.9886 (3.35); 1.7027 (0.68); 1.6747

(1.49); 1.6473 (1.35); 1.6187 (0.51); 1.2360 (0.51); 1.1925 (0.89); 1.1747 (1.77); 1.1569 (0.86); −0.0002 (4.40);

Ex. 39, Solvent: DMSO, Spectrometer: 399.95 MHz 8.1588 (3.15); 7.9410 (9.29); 7.3715 (1.93); 7.3509 (4.10); 7.3300 (4.13); 7.3227 (3.11); 7.2026 (2.15); 7.1817 (3.00); 7.1038 (2.36); 7.1016 (3.27); 7.0883 (2.72); 7.0832 (6.50); 7.0681 (1.94); 7.0626 (3.65); 6.2591 (1.36); 6.2356 (1.73); 6.2282 (1.60); 6.2046 (1.40); 5.8317 (0.37); 5.8181 (0.77); 5.8051 (0.72); 5.7917 (0.90); 5.7888 (0.58); 5.7782 (0.52); 5.7748 (0.98); 5.7617 (0.88); 5.7533 (7.80); 5.7488 (1.23); 5.7350 (0.48); 5.2725 (0.61); 5.2686 (1.79); 5.2645 (1.88); 5.2607 (0.73); 5.2291 (0.52); 5.2253 (1.53); 5.2212 (1.58); 5.2173 (0.60); 5.0153 (1.67); 5.0116 (1.68); 4.9889 (1.55); 4.9852 (1.59); 4.5819 (0.45); 4.5687 (0.48); 4.5502 (1.39); 4.5369 (1.39); 4.5231 (1.42); 4.5090 (1.36); 4.4913 (0.49); 4.4809 (0.36); 4.4771 (0.45); 4.1741 (1.49); 4.1408 (1.58); 4.0559 (0.39); 4.0381 (1.22); 4.0202 (1.23); 4.0025 (0.42); 3.7617 (1.06); 3.7306 (1.30); 3.7197 (1.87); 3.6887 (1.52); 3.5785 (1.71); 3.5549 (1.74); 3.5365 (1.20); 3.5130 (1.25); 3.3616 (206.47); 3.3582 (217.30); 3.3552 (181.25); 3.3479 (336.94); 3.0516 (1.16); 3.0221 (2.01); 2.9935 (1.15); 2.9264 (0.94); 2.6768 (0.56); 2.6722 (0.78); 2.6677 (0.55); 2.5257 (2.16); 2.5210 (3.11); 2.5123 (41.85); 2.5078 (87.47); 2.5032 (117.61); 2.4986 (86.11); 2.4940 (42.20); 2.3344 (0.60); 2.3299 (0.82); 2.3253 (0.61); 2.1553 (16.00); 2.1044 (1.29); 2.0730 (1.96); 1.9887 (5.62); 1.7272 (0.42); 1.7174 (0.54); 1.6955 (1.13); 1.6874 (1.27); 1.6656 (1.19); 1.6575 (1.10); 1.6361 (0.48); 1.6262 (0.40); 1.2350 (0.36); 1.1926 (1.55); 1.1748 (3.07); 1.1570 (1.50); −0.0002 (2.02);

Ex. 40, Solvent: DMSO, Spectrometer: 399.95 MHz 8.0340 (9.26); 7.4541 (1.53); 7.4344 (3.45); 7.4147 (2.25); 7.2915 (1.97); 7.2722 (1.59); 7.1628 (1.73); 7.1577 (2.93); 7.1533 (2.10); 7.1184 (1.43); 7.1162 (1.62); 7.1127 (1.30); 7.1104 (1.26); 7.0983 (1.34); 7.0961 (1.38); 7.0927 (1.25); 7.0903 (1.15); 6.4980 (4.43); 5.7802 (1.13); 5.7604 (1.37); 5.7531 (1.33); 5.7332 (1.17); 5.3497 (0.88); 5.3073 (2.72); 5.2577 (2.67); 5.2151 (0.88); 5.1965 (0.85); 4.3847 (0.72); 4.3507 (0.77); 4.0557 (0.72); 4.0379 (2.19); 4.0201 (2.25); 4.0023 (0.93); 3.9883 (0.68); 3.9532 (0.75); 3.9232 (1.23); 3.8957 (1.41); 3.8800 (1.64); 3.8527 (1.33); 3.4089 (1.99); 3.3998 (0.57); 3.3890 (2.04); 3.3807 (1.25); 3.3707 (0.96); 3.3655 (1.83); 3.3456 (3.26); 3.3292 (241.15); 3.3261 (302.53); 3.2659 (1.26); 3.2371 (0.70); 3.0429 (1.96); 2.8659 (0.52); 2.8546 (1.70); 2.8352 (0.92); 2.8076 (0.53); 2.6753 (0.51); 2.6707 (0.71); 2.6662 (0.53); 2.5409 (0.35); 2.5241 (1.21); 2.5192 (1.89); 2.5106 (36.46); 2.5061 (78.71); 2.5015 (111.02); 2.4969 (83.92); 2.4925 (41.55); 2.3329 (0.55); 2.3283 (0.77); 2.3238 (0.58); 2.2070 (16.00); 2.1924 (1.81); 2.1325 (0.67); 2.1004 (1.39); 2.0735 (1.03); 1.9885 (9.76); 1.9183 (0.43); 1.9063 (0.85); 1.8989 (0.95); 1.8956 (0.73); 1.8870 (1.65); 1.8813 (0.75); 1.8750 (0.97); 1.8676 (1.00); 1.8557 (0.74); 1.8447 (0.33); 1.8248 (0.61); 1.8157 (0.64); 1.7930 (0.58); 1.7849 (0.55); 1.5824 (0.56);

1.5734 (0.62); 1.5523 (0.58); 1.5439 (0.58); 1.3976 (0.58); 1.2355 (0.40); 1.1923 (2.67); 1.1745 (5.40); 1.1567 (2.63); 1.0807 (0.55); 1.0670 (1.78); 1.0595 (3.41); 1.0558 (1.68); 1.0530 (1.79); 1.0470 (1.69); 1.0392 (3.51); 1.0334 (2.18); 1.0311 (2.14); 1.0249 (3.40); 1.0179 (3.09); 1.0139 (3.90); 1.0060 (1.80); 0.9919 (0.44); 0.0080 (1.09); −0.0002 (35.44); −0.0085 (1.38);

Ex. 41, Solvent: DMSO, Spectrometer: 399.95 MHz 8.0259 (9.47); 7.3231 (1.61); 7.3190 (0.50); 7.3027 (3.67); 7.2952 (0.37); 7.2825 (2.20); 6.9632 (4.18); 6.9580 (3.28); 6.9534 (2.20); 6.9445 (1.95); 6.9304 (1.59); 6.9278 (1.49); 6.9245 (1.19); 6.9221 (1.11); 6.9097 (1.41); 6.9079 (1.39); 6.9036 (1.22); 6.4980 (4.40); 6.0822 (0.43); 6.0692 (0.96); 6.0560 (0.94); 6.0428 (1.11); 6.0390 (0.59); 6.0298 (0.60); 6.0259 (1.19); 6.0128 (1.05); 5.9996 (1.20); 5.9866 (0.57); 5.7179 (1.17); 5.6978 (1.40); 5.6911 (1.37); 5.6706 (1.21); 5.4168 (0.67); 5.4126 (1.94); 5.4082 (2.03); 5.4039 (0.75); 5.3737 (0.62); 5.3694 (1.73); 5.3650 (1.80); 5.3607 (0.77); 5.3504 (0.89); 5.3076 (2.74); 5.2632 (2.49); 5.2590 (4.21); 5.2407 (0.78); 5.2370 (1.73); 5.2328 (1.74); 5.2294 (0.81); 5.2153 (0.92); 5.1968 (0.86); 4.5810 (2.25); 4.5772 (4.03); 4.5735 (2.51); 4.5680 (2.46); 4.5642 (4.01); 4.5606 (2.36); 4.3853 (0.73); 4.3525 (0.77); 4.0377 (0.73); 4.0200 (0.78); 4.0021 (0.45); 3.9890 (0.69); 3.9532 (0.73); 3.8941 (1.27); 3.8670 (1.46); 3.8512 (1.69); 3.8239 (1.42); 3.4095 (0.54); 3.3929 (1.96); 3.3809 (1.27); 3.3725 (2.16); 3.3619 (0.42); 3.3500 (2.09); 3.3262 (194.10); 3.3243 (226.61); 3.3220 (303.73); 3.2983 (3.23); 3.2653 (1.26); 3.2367 (0.64); 3.2314 (0.57); 3.0428 (2.05); 2.8659 (0.53); 2.8544 (1.75); 2.8381 (0.92); 2.8086 (0.52); 2.6792 (0.39); 2.6748 (0.88); 2.6702 (1.21); 2.6657 (0.89); 2.6612 (0.41); 2.5406 (0.42); 2.5237 (2.26); 2.5188 (3.67); 2.5102 (61.32); 2.5057 (131.73); 2.5011 (185.44); 2.4966 (139.12); 2.4921 (67.67); 2.3326 (0.93); 2.3280 (1.24); 2.3234 (0.94); 2.3188 (0.50); 2.2068 (16.00); 2.1923 (1.83); 2.1313 (0.66); 2.1023 (1.37); 2.0736 (1.16); 1.9884 (3.47); 1.8230 (0.57); 1.8150 (0.63); 1.7916 (0.57); 1.7835 (0.54); 1.5831 (0.57); 1.5736 (0.63); 1.5521 (0.59); 1.5421 (0.57); 1.3976 (0.32); 1.2583 (0.39); 1.2493 (0.59); 1.2354 (0.71); 1.1922 (0.94); 1.1744 (1.90); 1.1566 (0.93); 0.0080 (2.08); −0.0002 (68.81); −0.0085 (2.53);

Ex. 42, Solvent: DMSO, Spectrometer: 601.6 MHz 8.0198 (3.29); 7.9396 (10.59); 7.3640 (2.27); 7.3503 (4.58); 7.3366 (2.94); 7.1002 (2.64); 7.0987 (3.30); 7.0868 (2.70); 7.0852 (2.96); 7.0813 (2.45); 7.0671 (2.24); 7.0451 (2.24); 7.0324 (2.55); 6.9980 (2.70); 6.8566 (1.49); 6.8547 (1.50); 6.8439 (1.31); 6.8421 (1.31); 6.2494 (1.52); 6.2337 (1.82); 6.2287 (1.73); 6.2131 (1.56); 5.8156 (0.47); 5.8065 (0.92); 5.7978 (0.85); 5.7890 (1.03); 5.7869 (0.64); 5.7799 (0.59); 5.7777 (1.10); 5.7690 (0.94); 5.7602 (1.06); 5.7555 (1.13); 5.7512 (0.57); 5.2645 (0.67); 5.2618 (2.03); 5.2591 (2.05); 5.2564 (0.74); 5.2357 (0.62); 5.2331 (1.79); 5.2303 (1.85); 5.2277 (0.64); 5.0126 (0.70); 5.0104 (1.86); 5.0079 (1.83); 5.0057 (0.74); 4.9951 (0.68); 4.9929 (1.76); 4.9904 (1.76); 4.9882 (0.71); 4.5755 (0.35); 4.5732 (0.62); 4.5708 (0.38); 4.5667

(0.38); 4.5644 (0.63); 4.5621 (0.37); 4.5544 (0.78); 4.5521 (1.36); 4.5497 (0.85); 4.5456 (0.80); 4.5433 (1.33); 4.5410 (0.78); 4.5214 (0.78); 4.5192 (1.35); 4.5170 (0.83); 4.5120 (0.80); 4.5098 (1.34); 4.5077 (0.79); 4.5004 (0.38); 4.4981 (0.66); 4.4958 (0.40); 4.4910 (0.37); 4.4887 (0.63); 4.4865 (0.37); 4.1690 (1.42); 4.1468 (1.48); 4.0466 (1.14); 4.0348 (3.48); 4.0229 (3.47); 4.0111 (1.16); 3.7493 (1.28); 3.7286 (1.61); 3.7214 (1.98); 3.7008 (1.62); 3.5691 (1.84); 3.5535 (1.86); 3.5413 (1.45); 3.5257 (1.45); 3.3579 (0.37); 3.3517 (0.85); 3.3481 (0.61); 3.3454 (0.84); 3.3251 (591.42); 3.3079 (1.11); 3.3012 (4.55); 3.0160 (0.87); 3.0123 (1.06); 2.9927 (1.95); 2.9738 (1.08); 2.9701 (0.92); 2.6190 (0.40); 2.6160 (0.88); 2.6130 (1.25); 2.6099 (0.90); 2.6069 (0.41); 2.5405 (0.37); 2.5223 (3.07); 2.5192 (3.82); 2.5161 (3.46); 2.5074 (64.00); 2.5043 (141.18); 2.5012 (196.75); 2.4981 (141.80); 2.4951 (65.39); 2.3915 (0.37); 2.3885 (0.85); 2.3854 (1.21); 2.3823 (0.86); 2.3793 (0.38); 2.2327 (12.96); 2.1103 (13.21); 2.0890 (1.16); 2.0837 (1.23); 2.0734 (1.26); 2.0670 (1.33); 1.9884 (16.00); 1.6966 (0.39); 1.6905 (0.47); 1.6763 (1.08); 1.6704 (1.18); 1.6561 (1.12); 1.6504 (1.09); 1.6365 (0.44); 1.6299 (0.37); 1.3976 (0.40); 1.1862 (4.45); 1.1744 (9.23); 1.1626 (4.25); 0.0053 (0.64); −0.0002 (24.12); −0.0057 (0.68);

Ex. 43, Solvent: CD3CN, Spectrometer: 399.95 MHz 7.7017 (16.00); 7.5291 (2.62); 7.5095 (4.66); 7.4599 (1.87); 7.4556 (2.02); 7.4419 (3.09); 7.4379 (4.17); 7.4302 (2.69); 7.4189 (4.14); 7.4148 (6.16); 7.3934 (4.06); 7.3899 (3.96); 7.3753 (3.19); 7.3569 (1.29); 7.3536 (1.16); 6.4212 (7.95); 6.0279 (2.81); 6.0066 (3.23); 6.0002 (3.19); 5.9789 (2.93); 5.1548 (1.55); 5.1129 (7.73); 5.0841 (7.77); 5.0630 (0.76); 5.0419 (1.47); 4.8696 (4.32); 4.8408 (6.69); 4.7412 (7.05); 4.7123 (4.54); 4.5215 (1.52); 4.4876 (1.67); 4.1147 (1.76); 4.0968 (5.36); 4.0790 (5.57); 4.0678 (1.89); 4.0612 (2.11); 4.0560 (2.15); 4.0534 (1.43); 4.0451 (5.27); 4.0334 (5.47); 4.0225 (5.45); 4.0107 (5.47); 4.0023 (1.59); 3.9998 (2.14); 3.9880 (2.51); 3.9798 (2.25); 3.9570 (0.81); 3.9327 (4.54); 3.9049 (3.73); 3.8896 (4.22); 3.8619 (4.00); 3.4070 (0.67); 3.3974 (1.35); 3.3878 (0.87); 3.3783 (1.53); 3.3687 (2.87); 3.3591 (1.67); 3.3494 (2.09); 3.3407 (2.44); 3.3303 (1.21); 3.3227 (4.99); 3.3136 (2.36); 3.3017 (4.36); 3.2797 (4.61); 3.2586 (3.78); 2.9157 (1.05); 2.9093 (1.15); 2.8782 (2.03); 2.8520 (1.17); 2.8454 (1.08); 2.4976 (0.34); 2.2545 (40.20); 2.2208 (828.11); 2.2177 (745.43); 2.1497 (2.66); 2.1436 (2.69); 2.1374 (2.27); 2.1312 (1.52); 2.1250 (0.99); 2.0912 (0.59); 2.0015 (24.43); 1.9943 (7.48); 1.9880 (7.97); 1.9823 (68.62); 1.9762 (130.30); 1.9700 (182.81); 1.9638 (126.48); 1.9576 (65.15); 1.9303 (1.19); 1.9197 (1.10); 1.8997 (1.68); 1.8900 (1.75); 1.8680 (1.55); 1.8584 (1.52); 1.8382 (0.87); 1.8278 (0.69); 1.8108 (0.60); 1.8046 (0.94); 1.7984 (1.25); 1.7922 (0.94); 1.7861 (0.56); 1.7660 (0.75); 1.7553 (0.82); 1.7355 (1.55); 1.7253 (1.60); 1.7042 (1.49); 1.6942 (1.45); 1.6744 (0.70); 1.6635 (0.66); 1.4653 (1.05); 1.3891 (0.33); 1.2986 (1.87); 1.2504 (6.62); 1.2326 (12.99); 1.2147 (6.49);

Ex. 44, Solvent: CD3CN, Spectrometer: 399.95 MHz 7.6732 (4.41); 7.4745 (0.94); 7.4565 (1.13); 7.4523 (1.04); 7.3852 (0.53); 7.3812 (0.64); 7.3687 (1.08); 7.3640 (1.38); 7.3565 (1.61); 7.3526 (1.54); 7.3477 (1.18); 7.3262 (1.14); 7.3226 (1.11); 7.3066 (0.84); 6.3930 (2.25); 6.0032 (0.78); 5.9814 (0.93); 5.9756 (0.90); 5.9538 (0.80); 5.1262 (0.46); 5.0841 (2.18); 5.0558 (2.16); 5.0139 (0.41); 4.6676 (1.34); 4.6387 (2.06); 4.5397 (2.16); 4.5108 (1.47); 4.4929 (0.48); 4.4592 (0.51); 4.0683 (0.55); 4.0504 (0.54); 3.9493 (1.39); 3.9217 (1.31); 3.9062 (1.51); 3.8785 (1.11); 3.6257 (0.85); 3.6130 (1.73); 3.6025 (3.17); 3.5924 (1.34); 3.5316 (2.71); 3.5217 (2.79); 3.5177 (1.62); 3.5106 (1.21); 3.5076 (1.14); 3.3701 (0.38); 3.3510 (0.45); 3.3413 (0.82); 3.3317 (0.51); 3.3194 (0.56); 3.3126 (0.88); 3.2965 (16.00); 3.2833 (1.32); 3.2790 (1.78); 3.2675 (0.34); 3.2573 (1.34); 3.2482 (0.40); 3.2357 (1.04); 3.2141 (1.01); 2.8782 (0.34); 2.8476 (0.60); 2.8214 (0.34); 2.8155 (0.32); 2.4691 (0.44); 2.2258 (12.47); 2.2245 (12.61); 2.2048 (274.24); 2.1995 (217.79); 2.1214 (0.81); 2.1153 (0.79); 2.1091 (0.70); 2.1029 (0.44); 1.9729 (2.73); 1.9659 (2.55); 1.9540 (26.83); 1.9478 (51.05); 1.9417 (70.86); 1.9355 (49.44); 1.9293 (25.39); 1.9048 (0.46); 1.8942 (0.37); 1.8736 (0.51); 1.8642 (0.53); 1.8424 (0.46); 1.8331 (0.47); 1.7763 (0.36); 1.7701 (0.48); 1.7639 (0.36); 1.7087 (0.45); 1.6988 (0.48); 1.6775 (0.44); 1.6675 (0.44); 1.2699 (0.61); 1.2218 (0.68); 1.2040 (1.33); 1.1862 (0.67); −0.0002 (0.39);

Ex. 45, Solvent: DMSO, Spectrometer: 399.95 MHz 8.0061 (9.48); 7.9826 (0.77); 7.6598 (0.38); 7.3440 (1.15); 7.3246 (5.02); 7.3058 (4.59); 7.1517 (2.63); 7.1318 (2.19); 7.0473 (2.59); 7.0283 (2.99); 7.0207 (2.26); 7.0000 (4.37); 6.9832 (1.47); 6.8561 (1.85); 6.8393 (1.79); 5.8864 (1.24); 5.8686 (1.50); 5.8588 (1.54); 5.8407 (1.30); 5.7552 (11.14); 4.8813 (6.84); 4.8756 (7.31); 4.1688 (1.86); 4.1351 (1.96); 4.0375 (0.44); 4.0198 (0.43); 3.9005 (1.28); 3.8727 (1.45); 3.8576 (1.70); 3.8298 (1.38); 3.5843 (1.93); 3.5785 (3.88); 3.5727 (1.85); 3.3549 (49.56); 3.3360 (230.21); 3.3284 (217.08); 3.3256 (287.42); 3.2867 (2.54); 3.2724 (2.74); 3.2544 (2.19); 3.2403 (0.76); 3.2293 (1.76); 3.2115 (1.70); 3.1978 (0.45); 3.1549 (0.35); 3.1491 (0.47); 2.9978 (1.36); 2.9676 (2.48); 2.9391 (1.36); 2.9078 (7.08); 2.6750 (0.71); 2.6706 (0.96); 2.6662 (0.71); 2.5408 (0.63); 2.5060 (108.78); 2.5015 (142.02); 2.4971 (107.62); 2.3326 (0.81); 2.3282 (1.05); 2.3239 (0.84); 2.2620 (0.49); 2.2319 (14.26); 2.1266 (0.83); 2.1063 (16.00); 2.0734 (2.22); 2.0429 (2.16); 1.9884 (1.83); 1.6864 (0.67); 1.6787 (0.78); 1.6565 (1.51); 1.6485 (1.61); 1.6261 (1.49); 1.6187 (1.39); 1.5966 (0.58); 1.5873 (0.47); 1.2581 (0.37); 1.2346 (1.05); 1.1923 (0.52); 1.1745 (0.99); 1.1567 (0.51); 0.0079 (1.58); −0.0002 (26.90); −0.0083 (1.28);

Ex. 46, Solvent: DMSO, Spectrometer: 399.95 MHz 8.0114 (3.98); 8.0029 (11.23); 7.3168 (0.64); 7.3102 (2.52); 7.3057 (2.06); 7.2948 (3.13); 7.2911 (3.67); 7.2869 (2.38); 7.2770 (1.89); 7.2727 (1.12); 7.0621 (2.97); 7.0470 (3.07); 7.0424 (2.86); 7.0400 (2.62); 7.0278 (3.25); 6.9937 (3.44); 6.9741 (1.81); 6.9554 (2.92); 6.9385 (1.31); 6.9367 (1.32); 6.8563 (1.94); 6.8404 (1.62); 6.8372 (1.60); 6.0807 (0.50); 6.0682 (1.08); 6.0546 (0.80); 6.0417 (1.23); 6.0374 (0.69); 6.0293 (0.63); 6.0249 (1.34); 6.0114 (0.91); 5.9984

(1.32); 5.9860 (0.64); 5.9166 (1.45); 5.8987 (1.67); 5.8889 (1.66); 5.8708 (1.52); 5.4429 (0.74); 5.4386 (2.25); 5.4343 (2.36); 5.4300 (0.91); 5.3996 (0.64); 5.3953 (1.95); 5.3910 (2.07); 5.3867 (0.80); 5.2483 (0.83); 5.2445 (2.18); 5.2405 (2.21); 5.2369 (0.89); 5.2218 (0.75); 5.2180 (2.01); 5.2140 (2.08); 5.2104 (0.84); 4.6375 (1.28); 4.6331 (2.95); 4.6284 (3.27); 4.6249 (2.68); 4.6210 (3.20); 4.6161 (3.05); 4.1680 (1.90); 4.1345 (1.99); 4.0556 (1.04); 4.0378 (3.12); 4.0200 (3.15); 4.0022 (1.05); 3.8925 (1.59); 3.8645 (1.82); 3.8497 (2.08); 3.8218 (1.73); 3.3907 (0.37); 3.3748 (0.51); 3.3267 (710.58); 3.2892 (3.58); 3.2791 (1.56); 3.2711 (2.91); 3.2574 (0.53); 3.2464 (2.07); 3.2284 (2.00); 3.0001 (1.35); 2.9703 (2.48); 2.9418 (1.39); 2.6795 (0.44); 2.6752 (0.98); 2.6706 (1.42); 2.6660 (1.05); 2.6614 (0.52); 2.5408 (0.73); 2.5240 (2.28); 2.5193 (3.48); 2.5105 (71.10); 2.5060 (152.70); 2.5014 (209.79); 2.4969 (155.79); 2.4924 (77.49); 2.3373 (0.50); 2.3328 (1.07); 2.3282 (1.49); 2.3237 (1.12); 2.3191 (0.57); 2.2321 (15.82); 2.1056 (16.00); 2.0735 (3.20); 2.0413 (1.86); 1.9885 (13.82); 1.6890 (0.55); 1.6799 (0.66); 1.6586 (1.41); 1.6501 (1.59); 1.6278 (1.45); 1.6193 (1.40); 1.5978 (0.57); 1.5879 (0.48); 1.3976 (1.15); 1.2978 (0.39); 1.2583 (0.59); 1.2348 (1.38); 1.1923 (3.77); 1.1745 (7.51); 1.1567 (3.71); −0.0002 (6.96);

Ex. 47, Solvent: DMSO, Spectrometer: 399.95 MHz 8.7845 (0.35); 8.0356 (1.18); 8.0319 (7.37); 8.0173 (0.49); 7.5869 (0.42); 7.4420 (0.59); 7.4347 (3.88); 7.4182 (1.40); 7.4133 (4.68); 7.3994 (0.34); 7.3507 (0.44); 7.1707 (0.68); 7.1642 (5.09); 7.1593 (1.82); 7.1477 (1.45); 7.1427 (4.51); 7.1361 (0.67); 6.4984 (4.27); 5.7729 (1.07); 5.7530 (1.32); 5.7460 (1.23); 5.7256 (1.00); 5.3488 (0.82); 5.3061 (2.51); 5.2560 (2.62); 5.2135 (0.86); 4.3851 (0.72); 4.3514 (0.78); 4.0558 (0.62); 4.0380 (1.84); 4.0202 (1.89); 4.0024 (0.80); 3.9879 (0.71); 3.9524 (0.75); 3.9109 (1.03); 3.8837 (1.26); 3.8679 (1.39); 3.8406 (1.14); 3.4604 (0.37); 3.4400 (0.63); 3.4132 (2.35); 3.3927 (3.49); 3.3525 (353.69); 3.3485 (459.15); 3.3461 (516.01); 3.3421 (735.82); 3.2661 (2.04); 3.2380 (1.15); 3.2318 (1.10); 3.1922 (0.43); 2.8668 (0.59); 2.8363 (0.98); 2.8095 (0.58); 2.6807 (0.41); 2.6763 (0.84); 2.6717 (1.18); 2.6672 (0.88); 2.6628 (0.45); 2.5419 (0.62); 2.5251 (2.21); 2.5204 (3.20); 2.5117 (56.02); 2.5072 (119.61); 2.5027 (163.85); 2.4981 (121.68); 2.4936 (60.83); 2.3385 (0.42); 2.3340 (0.83); 2.3294 (1.15); 2.3249 (0.87); 2.3202 (0.44); 2.2069 (16.00); 2.1340 (0.75); 2.1017 (1.45); 2.0861 (1.25); 2.0729 (1.73); 1.9886 (8.30); 1.9241 (0.45); 1.9123 (0.85); 1.9045 (0.99); 1.9016 (0.74); 1.8929 (1.48); 1.8887 (0.92); 1.8812 (0.96); 1.8732 (0.96); 1.8615 (0.56); 1.8252 (0.61); 1.8148 (0.66); 1.7924 (0.59); 1.7839 (0.57); 1.7603 (0.33); 1.6043 (0.33); 1.5838 (0.59); 1.5743 (0.65); 1.5525 (0.63); 1.5443 (0.61); 1.3976 (1.15); 1.2349 (0.77); 1.1925 (2.26); 1.1747 (4.49); 1.1569 (2.23); 1.1158 (0.39); 1.0957 (0.36); 1.0830 (0.77); 1.0704 (1.81); 1.0631 (3.57); 1.0553 (2.15); 1.0505 (1.85); 1.0431 (2.83); 1.0368 (1.75); 1.0246 (1.74); 1.0175 (3.08); 1.0106 (3.01); 1.0063 (3.12); 0.9984 (2.10); 0.9854 (0.50); 0.0080 (0.33); −0.0002 (11.67); −0.0084 (0.46);

Ex. 48, Solvent: DMSO, Spectrometer: 399.95 MHz 8.0329 (7.22); 7.4658 (0.49); 7.4552 (8.31); 7.4454 (4.85); 7.4417 (4.76); 7.4214 (0.51); 7.2027 (0.35); 7.1921 (2.05); 7.1817 (1.81); 7.1789 (1.98); 7.1687 (1.79); 6.5052 (4.35); 6.1109 (1.31); 6.0867 (1.67); 6.0798 (1.60); 6.0555 (1.36); 5.7630 (9.67); 5.3651 (0.98); 5.3226 (2.46); 5.2634 (2.42); 5.2208 (0.98); 4.3907 (0.71); 4.3580 (0.75); 4.0544 (0.35); 4.0367 (1.07); 4.0189 (1.11); 4.0010 (0.69); 3.9922 (0.67); 3.9571 (0.72); 3.9209 (1.11); 3.8896 (1.34); 3.8776 (1.54); 3.8464 (1.23); 3.4331 (1.62); 3.4211 (0.73); 3.4089 (1.99); 3.4016 (1.17); 3.3900 (3.25); 3.3692 (105.50); 3.3662 (108.97); 3.3627 (125.98); 3.3573 (125.25); 3.3535 (153.94); 3.3133 (0.59); 3.2996 (0.80); 3.2691 (1.11); 3.2411 (0.58); 3.0424 (0.57); 2.8682 (0.53); 2.8540 (0.58); 2.8380 (0.90); 2.8106 (0.52); 2.6772 (0.44); 2.6726 (0.62); 2.6680 (0.44); 2.5261 (1.16); 2.5214 (1.66); 2.5126 (31.65); 2.5081 (69.43); 2.5035 (94.42); 2.4989 (67.38); 2.4944 (31.70); 2.3347 (0.46); 2.3303 (0.64); 2.3257 (0.48); 2.2067 (16.00); 2.1915 (0.73); 2.1337 (0.69); 2.1264 (0.52); 2.1033 (1.36); 2.0774 (1.16); 1.9902 (4.94); 1.8206 (0.56); 1.8121 (0.62); 1.7897 (0.56); 1.7816 (0.52); 1.6306 (0.37); 1.6183 (0.69); 1.6112 (0.91); 1.6056 (0.71); 1.5993 (1.52); 1.5876 (1.00); 1.5796 (1.26); 1.5678 (1.05); 1.5464 (0.60); 1.5370 (0.58); 1.1920 (1.38); 1.1742 (2.75); 1.1564 (1.35); 0.9614 (0.64); 0.9531 (0.62); 0.9425 (2.08); 0.9294 (1.10); 0.9219 (2.04); 0.9102 (0.90); 0.9030 (0.72); 0.8210 (0.39); 0.8110 (0.77); 0.8005 (0.70); 0.7932 (0.89); 0.7835 (0.72); 0.7686 (0.74); 0.7586 (0.60); 0.7470 (0.93); 0.7375 (0.80); 0.7268 (0.86); 0.7176 (0.60); 0.0080 (0.72); −0.0002 (27.69); −0.0085 (1.03);

Ex. 49, Solvent: DMSO, Spectrometer: 399.95 MHz 7.9775 (7.21); 7.9529 (0.74); 7.3985 (0.59); 7.3812 (0.71); 7.3775 (1.25); 7.3604 (1.27); 7.3567 (0.82); 7.3395 (0.66); 6.9326 (1.66); 6.9116 (1.52); 6.8657 (0.89); 6.8415 (1.10); 6.8200 (0.86); 6.5035 (3.21); 6.0604 (0.81); 6.0378 (1.02); 6.0299 (0.96); 6.0070 (0.85); 5.3679 (0.77); 5.3253 (1.93); 5.2637 (1.85); 5.2211 (0.75); 4.3962 (0.51); 4.3632 (0.54); 4.1114 (1.81); 4.1006 (2.89); 4.0887 (1.95); 4.0548 (0.57); 4.0370 (1.71); 4.0192 (1.75); 4.0013 (0.96); 3.9626 (0.51); 3.7633 (0.56); 3.7322 (0.67); 3.7208 (0.99); 3.6903 (0.88); 3.5957 (1.03); 3.5730 (1.06); 3.5536 (0.67); 3.5309 (0.66); 3.4820 (1.31); 3.4783 (1.25); 3.4727 (2.14); 3.4652 (2.14); 3.4542 (1.04); 3.4264 (0.43); 3.4069 (0.40); 3.3973 (0.75); 3.3870 (0.38); 3.3688 (0.48); 3.3607 (0.74); 3.3419 (218.73); 3.3183 (1.43); 3.3079 (0.72); 3.3033 (0.71); 3.2721 (0.80); 3.2654 (0.64); 3.2445 (0.46); 3.0407 (0.36); 3.0169 (16.00); 2.8906 (6.62); 2.8700 (0.39); 2.8386 (0.74); 2.8125 (0.39); 2.7310 (5.14); 2.6763 (0.36); 2.6718 (0.52); 2.6673 (0.37); 2.5252 (0.78); 2.5206 (1.20); 2.5118 (26.94); 2.5073 (58.44); 2.5028 (78.90); 2.4982 (55.83); 2.4937 (26.07); 2.3342 (0.39); 2.3295 (0.54); 2.3249 (0.40); 2.2087 (12.09); 2.1393 (0.48); 2.1331 (0.49); 2.1257 (0.45); 2.1104 (0.99); 2.0768 (0.66); 1.9899 (7.95); 1.9076 (0.84); 1.8267 (0.44); 1.8211 (0.47); 1.7982 (0.43); 1.7900 (0.40); 1.5843 (0.41); 1.5753 (0.46); 1.5538 (0.44); 1.5450 (0.43); 1.1920

(2.10); 1.1742 (4.23); 1.1564 (2.04); 0.0080 (0.40); −0.0002 (14.85); −0.0085 (0.51);

Ex. 50, Solvent: DMSO, Spectrometer: 399.95 MHz 7.9530 (8.91); 7.3744 (1.93); 7.3538 (4.10); 7.3332 (2.69); 7.1062 (2.47); 7.1041 (3.28); 7.0859 (4.76); 7.0839 (4.63); 7.0648 (2.13); 6.5062 (4.45); 6.2598 (1.34); 6.2363 (1.75); 6.2289 (1.61); 6.2053 (1.41); 5.8253 (0.33); 5.8117 (0.67); 5.7985 (0.66); 5.7852 (0.82); 5.7684 (0.90); 5.7616 (0.80); 5.7552 (0.78); 5.7420 (0.86); 5.7285 (0.44); 5.3676 (1.03); 5.3250 (2.60); 5.2642 (3.94); 5.2243 (2.34); 5.2207 (2.27); 5.0140 (1.59); 5.0105 (1.62); 4.9877 (1.50); 4.9843 (1.52); 4.5816 (0.47); 4.5687 (0.49); 4.5500 (1.39); 4.5367 (1.37); 4.5208 (1.37); 4.5066 (1.34); 4.4889 (0.48); 4.4748 (0.47); 4.3923 (0.71); 4.3596 (0.76); 4.0547 (0.87); 4.0369 (2.63); 4.0191 (2.70); 4.0012 (1.40); 3.9622 (0.72); 3.7620 (1.05); 3.7309 (1.29); 3.7201 (1.84); 3.6890 (1.47); 3.5752 (1.59); 3.5516 (1.58); 3.5332 (1.13); 3.5097 (1.10); 3.4242 (0.83); 3.3788 (255.26); 3.3768 (255.06); 3.3727 (209.45); 3.3699 (232.41); 3.3125 (1.04); 3.3074 (1.07); 3.2773 (1.18); 3.2489 (0.69); 3.2435 (0.63); 2.8774 (0.54); 2.8465 (0.94); 2.8206 (0.55); 2.6783 (0.38); 2.6737 (0.53); 2.6691 (0.39); 2.5271 (0.84); 2.5224 (1.36); 2.5136 (27.60); 2.5092 (60.18); 2.5046 (80.99); 2.5000 (57.47); 2.4955 (26.85); 2.3358 (0.40); 2.3313 (0.55); 2.3267 (0.40); 2.2088 (16.00); 2.1502 (0.67); 2.1123 (1.37); 2.0865 (0.77); 2.0771 (0.87); 1.9903 (12.30); 1.8314 (0.58); 1.8229 (0.64); 1.8004 (0.59); 1.7919 (0.55); 1.5907 (0.55); 1.5814 (0.64); 1.5603 (0.59); 1.5511 (0.58); 1.1921 (3.28); 1.1743 (6.54); 1.1565 (3.22); −0.0002 (4.51);

Ex. 51, Solvent: DMSO, Spectrometer: 399.95 MHz 7.9706 (8.74); 7.3989 (0.78); 7.3817 (0.97); 7.3779 (1.64); 7.3609 (1.66); 7.3571 (1.04); 7.3400 (0.84); 6.9372 (2.31); 6.9160 (2.12); 6.8675 (1.21); 6.8422 (1.42); 6.8207 (1.13); 6.5037 (4.21); 6.1077 (1.07); 6.0857 (1.30); 6.0770 (1.24); 6.0548 (1.13); 5.9293 (0.34); 5.9160 (0.74); 5.9029 (0.73); 5.8895 (0.86); 5.8864 (0.53); 5.8729 (0.95); 5.8596 (0.86); 5.8465 (0.92); 5.8334 (0.45); 5.3659 (1.00); 5.3406 (1.76); 5.3366 (1.84); 5.3327 (0.85); 5.3235 (2.65); 5.3012 (0.59); 5.2974 (1.51); 5.2933 (1.53); 5.2895 (0.62); 5.2665 (2.53); 5.2239 (0.98); 5.2032 (0.61); 5.1221 (1.65); 5.1185 (1.63); 5.0957 (1.55); 5.0922 (1.53); 4.5906 (1.63); 4.5869 (1.21); 4.5786 (2.74); 4.5662 (1.56); 4.3942 (0.70); 4.3609 (0.75); 4.0550 (1.00); 4.0372 (3.03); 4.0194 (3.09); 4.0015 (1.49); 3.9625 (0.71); 3.8005 (0.77); 3.7702 (0.88); 3.7578 (1.10); 3.7280 (1.01); 3.5352 (1.27); 3.5132 (1.28); 3.4928 (0.96); 3.4709 (0.98); 3.4237 (0.44); 3.4120 (0.35); 3.4037 (0.62); 3.3943 (1.11); 3.3854 (0.68); 3.3772 (0.39); 3.3744 (0.40); 3.3657 (0.78); 3.3620 (0.95); 3.3602 (0.99); 3.3556 (1.40); 3.3418 (302.46); 3.3264 (1.23); 3.3180 (1.55); 3.3079 (0.78); 3.3038 (0.71); 3.2744 (0.93); 3.2461 (0.52); 3.2401 (0.47); 3.0429 (1.33); 2.8736 (0.50); 2.8543 (1.43); 2.8467 (0.90); 2.8166 (0.51); 2.6763 (0.42); 2.6719 (0.59); 2.6673 (0.42); 2.5253 (0.96); 2.5206 (1.55); 2.5119 (31.01); 2.5074 (66.11); 2.5029 (88.42); 2.4984 (62.76); 2.4940 (29.40); 2.3344 (0.41); 2.3297 (0.58); 2.3251 (0.42);

2.2091 (16.00); 2.1913 (1.25); 2.1498 (0.67); 2.1466 (0.63); 2.1125 (1.31); 2.0862 (0.71); 2.0776 (0.71); 1.9900 (13.71); 1.8331 (0.55); 1.8264 (0.66); 1.8031 (0.54); 1.7952 (0.52); 1.5914 (0.55); 1.5826 (0.61); 1.5608 (0.58); 1.5508 (0.56); 1.2349 (0.34); 1.1921 (3.53); 1.1743 (7.13); 1.1564 (3.43); 0.0081 (0.47); −0.0002 (15.63); −0.0084 (0.51);

Ex. 52, Solvent: DMSO, Spectrometer: 601.6 MHz 8.0358 (7.61); 7.2774 (0.74); 7.2742 (0.77); 7.2644 (0.94); 7.2612 (1.03); 7.2580 (0.86); 7.2551 (0.81); 7.2446 (0.93); 7.2418 (0.95); 7.1645 (0.94); 7.1617 (1.01); 7.1515 (2.51); 7.1487 (1.98); 7.1409 (1.34); 7.1331 (1.26); 7.1279 (1.36); 7.1200 (1.37); 7.1150 (0.49); 7.1069 (0.50); 6.5053 (4.35); 6.0851 (0.60); 6.0763 (0.47); 6.0669 (0.85); 6.0568 (0.89); 6.0476 (0.52); 6.0393 (0.68); 6.0293 (0.35); 5.9261 (1.26); 5.9136 (1.43); 5.9074 (1.36); 5.8949 (1.27); 5.3966 (1.73); 5.3940 (1.69); 5.3915 (0.67); 5.3681 (1.60); 5.3654 (1.56); 5.3630 (0.64); 5.3509 (1.29); 5.3225 (2.53); 5.2618 (2.61); 5.2407 (1.82); 5.2382 (1.83); 5.2361 (1.33); 5.2336 (1.44); 5.2235 (1.62); 4.6113 (2.93); 4.6016 (2.75); 4.3806 (0.76); 4.3588 (0.79); 4.0335 (0.46); 4.0217 (0.46); 3.9801 (0.75); 3.9567 (0.77); 3.9224 (1.21); 3.9035 (1.38); 3.8938 (1.51); 3.8750 (1.27); 3.3986 (0.64); 3.3926 (0.49); 3.3855 (0.79); 3.3793 (1.41); 3.3493 (580.12); 3.3257 (12.73); 3.3089 (1.64); 3.2826 (0.66); 3.2634 (1.08); 3.2439 (0.62); 3.2396 (0.52); 2.8516 (0.54); 2.8309 (0.97); 2.8134 (0.56); 2.6178 (1.20); 2.6149 (1.62); 2.6119 (1.14); 2.5426 (0.65); 2.5241 (2.96); 2.5211 (4.06); 2.5179 (4.89); 2.5087 (96.04); 2.5061 (192.28); 2.5031 (255.09); 2.5002 (185.23); 2.4804 (1.02); 2.4773 (0.92); 2.3903 (1.26); 2.3873 (1.66); 2.3843 (1.20); 2.2055 (16.00); 2.1928 (0.47); 2.1259 (0.69); 2.0981 (1.15); 2.0783 (2.81); 1.9905 (2.01); 1.8291 (0.33); 1.8150 (0.64); 1.8090 (0.69); 1.7944 (0.66); 1.7890 (0.62); 1.5684 (0.65); 1.5622 (0.69); 1.5482 (0.67); 1.5419 (0.64); 1.3969 (0.47); 1.2337 (1.34); 1.1860 (0.57); 1.1741 (1.09); 1.1623 (0.56); 1.1365 (0.56); 0.0052 (2.96); −0.0002 (72.51); −0.0057 (2.46);

Ex. 53, Solvent: DMSO, Spectrometer: 601.6 MHz 10.2595 (5.04); 8.0507 (7.33); 7.7701 (1.91); 7.7685 (2.00); 7.7574 (2.47); 7.7558 (2.50); 7.6824 (0.70); 7.6738 (0.84); 7.6690 (1.38); 7.6607 (1.40); 7.6562 (0.94); 7.6476 (0.77); 7.6120 (1.19); 7.5949 (1.38); 7.5811 (0.83); 6.5807 (1.13); 6.5629 (1.65); 6.5441 (1.15); 6.5072 (4.42); 5.3547 (1.33); 5.3263 (2.70); 5.2687 (2.59); 5.2404 (1.30); 4.3893 (0.87); 4.3673 (0.90); 3.9893 (0.85); 3.9787 (1.05); 3.9761 (1.10); 3.9663 (0.96); 3.9589 (1.23); 3.9501 (1.01); 3.9476 (0.99); 3.9280 (0.85); 3.5858 (1.07); 3.5688 (1.10); 3.5567 (0.95); 3.5400 (0.94); 3.4250 (0.34); 3.4189 (0.62); 3.4124 (0.47); 3.4059 (0.76); 3.3998 (1.23); 3.3935 (0.82); 3.3865 (0.63); 3.3799 (1.01); 3.3550 (256.99); 3.3314 (3.80); 3.2926 (0.68); 3.2728 (1.16); 3.2537 (0.62); 3.2502 (0.55); 2.8615 (0.60); 2.8411 (1.10); 2.8235 (0.61); 2.6182 (0.47); 2.6154 (0.64); 2.6125 (0.50); 2.5244 (1.20); 2.5214 (1.70); 2.5065 (75.93); 2.5036 (101.45); 2.5007 (79.23); 2.3906 (0.48); 2.3877 (0.64); 2.3850 (0.50); 2.2082 (16.00); 2.1456 (0.76); 2.1201 (1.12); 2.0913 (0.88); 2.0788

(6.21); 1.8307 (0.72); 1.8107 (0.69); 1.5836 (0.67); 1.5643 (0.66); 0.0049 (0.68); −0.0002 (13.17);

Ex. 54, Solvent: DMSO, Spectrometer: 601.6 MHz 8.7986 (0.80); 8.0657 (0.34); 8.0560 (7.35); 7.3883 (0.52); 7.3857 (0.58); 7.3745 (1.21); 7.3720 (1.50); 7.3582 (1.39); 7.3556 (1.99); 7.3466 (1.11); 7.3429 (1.41); 7.3341 (1.38); 7.3293 (0.67); 7.3204 (0.56); 7.2762 (1.73); 7.2643 (1.25); 6.5057 (4.67); 5.8076 (1.23); 5.7950 (1.39); 5.7886 (1.33); 5.7758 (1.19); 5.3525 (1.24); 5.3241 (2.42); 5.2606 (2.46); 5.2323 (1.29); 4.3835 (0.74); 4.3617 (0.79); 4.0454 (0.50); 4.0336 (1.54); 4.0217 (1.56); 4.0099 (0.53); 3.9806 (0.75); 3.9577 (0.78); 3.9189 (1.07); 3.8997 (1.30); 3.8902 (1.38); 3.8711 (1.15); 3.4091 (0.41); 3.4028 (0.65); 3.3964 (0.51); 3.3898 (0.91); 3.3834 (1.46); 3.3753 (1.49); 3.3504 (474.54); 3.3268 (8.13); 3.3000 (1.54); 3.2873 (1.89); 3.2713 (1.56); 3.2588 (1.98); 3.2438 (0.60); 3.2396 (0.53); 2.8542 (0.55); 2.8505 (0.58); 2.8296 (1.00); 2.8122 (0.55); 2.8083 (0.49); 2.6209 (0.40); 2.6179 (0.83); 2.6150 (1.11); 2.6120 (0.79); 2.6090 (0.36); 2.5427 (0.68); 2.5242 (2.84); 2.5212 (3.66); 2.5180 (4.29); 2.5092 (64.10); 2.5062 (130.48); 2.5032 (174.29); 2.5002 (125.86); 2.4973 (57.51); 2.4799 (0.46); 2.4766 (0.46); 2.4738 (0.44); 2.3933 (0.43); 2.3904 (0.86); 2.3874 (1.12); 2.3844 (0.81); 2.3814 (0.39); 2.2201 (0.42); 2.2057 (16.00); 2.1901 (0.44); 2.1246 (0.69); 2.0965 (1.20); 2.0782 (2.29); 2.0713 (0.77); 1.9905 (6.90); 1.8821 (0.38); 1.8742 (0.72); 1.8695 (0.72); 1.8640 (0.95); 1.8612 (1.12); 1.8566 (0.62); 1.8537 (0.68); 1.8502 (0.75); 1.8406 (0.54); 1.8104 (0.60); 1.8039 (0.62); 1.7922 (0.72); 1.7867 (0.78); 1.7849 (0.70); 1.7792 (0.77); 1.7736 (0.34); 1.7716 (0.49); 1.7660 (0.46); 1.7354 (1.68); 1.5793 (0.35); 1.5662 (0.72); 1.5589 (0.80); 1.5456 (0.75); 1.5391 (0.65); 1.3969 (0.44); 1.2338 (0.92); 1.1860 (1.90); 1.1741 (3.78); 1.1623 (1.83); 1.0889 (0.49); 1.0841 (0.52); 1.0818 (1.11); 1.0767 (1.64); 1.0716 (0.99); 1.0687 (1.20); 1.0636 (1.59); 1.0587 (1.07); 1.0513 (0.99); 1.0481 (0.88); 1.0438 (1.23); 1.0381 (1.09); 1.0305 (0.91); 1.0247 (0.56); 1.0183 (0.45); 1.0128 (1.07); 1.0103 (0.64); 1.0053 (2.12); 1.0003 (1.42); 0.9975 (0.90); 0.9918 (2.06); 0.9789 (1.26); 0.9693 (0.47); 0.9641 (0.41); 0.0052 (1.72); −0.0002 (43.02); −0.0057 (1.34);

Ex. 55, Solvent: DMSO, Spectrometer: 399.95 MHz 7.9900 (5.11); 7.9528 (0.50); 7.3211 (0.55); 7.3176 (0.67); 7.2998 (3.31); 7.2812 (2.93); 7.0705 (1.58); 7.0499 (1.35); 6.9729 (0.99); 6.9546 (1.73); 6.9355 (0.83); 6.4972 (3.18); 5.8503 (0.83); 5.8310 (0.97); 5.8223 (0.94); 5.8027 (0.85); 5.7551 (4.32); 5.3500 (0.66); 5.3070 (1.88); 5.2535 (1.78); 5.2112 (0.63); 4.3837 (0.53); 4.3514 (0.57); 4.1549 (1.74); 4.1435 (2.88); 4.1318 (1.83); 3.9877 (0.51); 3.9499 (0.57); 3.8507 (0.85); 3.8225 (0.88); 3.8079 (1.06); 3.7800 (0.93); 3.6311 (1.80); 3.6195 (2.15); 3.6085 (1.44); 3.4026 (0.53); 3.3942 (0.34); 3.3750 (0.87); 3.3652 (0.66); 3.3274 (220.17); 3.2923 (1.45); 3.2735 (1.17); 3.2628 (0.82); 3.2288 (16.00); 2.8907 (2.87); 2.8654 (0.38); 2.8617 (0.39); 2.8323 (0.69); 2.8040 (0.40); 2.7315 (2.65); 2.6709 (0.42); 2.5018 (70.79); 2.3284 (0.42); 2.2064 (11.12); 2.1227 (0.49); 2.0958 (1.01); 2.0736 (0.61); 2.0630 (0.58); 1.9887 (0.52); 1.8156 (0.47); 1.8063 (0.47); 1.7840 (0.43); 1.7776 (0.42); 1.5733 (0.45); 1.5657 (0.46); 1.5433 (0.45); 1.5368 (0.43); 1.2357 (0.62); −0.0002 (10.11); −0.0082 (0.34);

Ex. 56, Solvent: DMSO, Spectrometer: 399.95 MHz 8.7868 (0.75); 8.0463 (0.81); 8.0388 (8.80); 7.4462 (1.28); 7.4419 (1.52); 7.4270 (1.61); 7.4229 (2.06); 7.4147 (0.94); 7.4104 (0.83); 7.3957 (1.69); 7.3911 (1.41); 7.3761 (1.48); 7.3717 (1.20); 7.3397 (0.34); 7.3110 (1.23); 7.3082 (1.42); 7.2922 (1.83); 7.2893 (1.97); 7.2736 (0.78); 7.2706 (0.76); 7.1763 (2.17); 7.1735 (2.19); 7.1562 (1.87); 7.1534 (1.78); 6.4972 (4.64); 5.7554 (11.20); 5.7402 (1.29); 5.7311 (1.31); 5.7115 (1.10); 5.3515 (0.79); 5.3091 (2.37); 5.2551 (2.53); 5.2130 (0.86); 4.3857 (0.69); 4.3536 (0.72); 4.0558 (0.33); 4.0379 (1.00); 4.0201 (1.05); 4.0023 (0.53); 3.9867 (0.68); 3.9522 (0.71); 3.8958 (1.11); 3.8672 (1.30); 3.8526 (1.44); 3.8241 (1.19); 3.4178 (0.34); 3.4083 (0.53); 3.3985 (0.40); 3.3893 (0.64); 3.3796 (1.07); 3.3705 (0.66); 3.3608 (0.54); 3.3515 (0.79); 3.3267 (95.06); 3.3230 (198.62); 3.2903 (1.88); 3.2705 (1.95); 3.2471 (1.43); 3.2359 (0.69); 3.2276 (1.64); 2.8628 (0.55); 2.8356 (0.90); 2.8060 (0.51); 2.6750 (0.40); 2.6705 (0.54); 2.6658 (0.41); 2.5406 (0.34); 2.5238 (0.95); 2.5191 (1.43); 2.5098 (30.88); 2.5057 (60.00); 2.5013 (83.80); 2.4971 (58.45); 2.4928 (29.21); 2.3329 (0.41); 2.3281 (0.52); 2.3236 (0.39); 2.2066 (16.00); 2.1936 (0.85); 2.1291 (0.65); 2.0990 (1.32); 2.0734 (1.01); 1.9884 (4.67); 1.8725 (0.41); 1.8566 (0.73); 1.8468 (0.87); 1.8412 (1.36); 1.8356 (0.87); 1.8301 (0.85); 1.8223 (0.97); 1.8105 (0.93); 1.7848 (0.54); 1.5759 (0.57); 1.5668 (0.59); 1.5442 (0.58); 1.5355 (0.54); 1.2344 (0.35); 1.1923 (1.29); 1.1745 (2.61); 1.1567 (1.28); 1.0728 (0.54); 1.0647 (0.67); 1.0578 (0.73); 1.0521 (1.19); 1.0467 (1.39); 1.0304 (2.30); 1.0194 (1.51); 1.0140 (2.46); 1.0076 (1.75); 1.0021 (1.05); 0.9962 (0.99); 0.9871 (1.16); 0.9824 (0.83); 0.9742 (0.89); 0.9631 (1.22); 0.9488 (0.63); 0.9430 (0.61); −0.0002 (3.06);

The intensity of sharp signals correlates with the height of the signals in a printed example of an NMR spectrum in cm and shows the true ratios of the signal intensities. In the case of broad signals, several peaks or the middle of the signal and their relative intensities may be shown in comparison to the most intense signal in the spectrum.

For calibration of the chemical shift of the 1H NMR spectra we use tetramethylsilane and/or the chemical shift of the solvent, particularly in the case of spectra measured in DMSO. Therefore, the tetramethylsilane peak may but need not occur in the NMR peak lists.

The lists of the 1H NMR peaks are similar to the conventional 1H NMR printouts and thus usually contain all peaks listed in conventional NMR interpretations.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-$d_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in Research Disclosure Database Number 564025.

Use Examples

Example A

Phytophthora Test (Tomato)/Protective

Solvent: 49 parts by weight of N,N-dimethylformamide
Emulsifier: 1 part by weight of alkylaryl polyglycol ether To produce a suitable active ingredient formulation, 1 part by weight of active ingredient is mixed with the stated amounts of solvent and emulsifier, and the concentrate is diluted with water to the desired concentration.

To test for protective efficacy, young tomato plants are sprayed with the active ingredient formulation at the stated application rate. 1 day after the treatment, the plants are inoculated with a spore suspension of Phytophthora infestans, and then left to stand at 100% rel. humidity and 22° C. for 24 h. Subsequently, the plants are placed in a climate chamber at approx. 96% relative air humidity and a temperature of approx. 20° C.

Evaluation follows 7 days after the inoculation. 0% means an efficacy which corresponds to that of the control, whereas an efficacy of 100% means that no infection is observed.

In this test, the following inventive compounds show, at an active ingredient concentration of 100 ppm, an efficacy of 70% or more:

TABLE 2

| Ex_no. | Eff. % |
|---|---|
| 1 | 100 |
| 2 | 100 |
| 3 | 100 |
| 4 | 95 |
| 5 | 95 |
| 6 | 95 |
| 7 | 100 |
| 8 | 100 |
| 9 | 94 |
| 11 | 85 |
| 12 | 75 |
| 13 | 89 |
| 18 | 100 |
| 19 | 98 |
| 25 | 100 |
| 26 | 100 |
| 29 | 100 |
| 30 | 97 |
| 34 | 100 |
| 35 | 100 |
| 36 | 100 |
| 37 | 94 |
| 38 | 94 |

TABLE 2-continued

| Ex_no. | Eff. % |
|---|---|
| 39 | 94 |
| 40 | 100 |
| 41 | 98 |
| 41 | 97 |
| 42 | 94 |
| 43 | 97 |
| 44 | 94 |
| 45 | 100 |
| 46 | 100 |
| 47 | 100 |
| 48 | 70 |
| 49 | 90 |
| 50 | 70 |
| 51 | 85 |
| 52 | 97 |
| 53 | 98 |
| 54 | 94 |
| 55 | 92 |
| 56 | 89 |

Example B

Plasmopara Test (Grapevine)/Protective

| Solvent: | 24.5 parts by weight of acetone |
| | 24.5 parts by weight of dimethylacetamide |
| Emulsifier: | 1 part by weight of alkylaryl polyglycol ether |

To produce a suitable active ingredient formulation, 1 part by weight of active ingredient is mixed with the stated amounts of solvent and emulsifier, and the concentrate is diluted with water to the desired concentration.

To test for protective efficacy, young plants are sprayed with the active ingredient formulation at the stated application rate. After the spray coating has dried on, the plants are inoculated with an aqueous spore suspension of Plasmopara viticola and then remain in an incubation cabin at approx. 20° C. and 100% relative air humidity for 1 day. Subsequently, the plants are placed in a greenhouse at approx. 21° C. and approx. 90% air humidity for 4 days. The plants are then moistened and placed in an incubation cabin for 1 day.

Evaluation follows 6 days after the inoculation. 0% means an efficacy which corresponds to that of the control, whereas an efficacy of 100% means that no infection is observed.

In this test, the following inventive compounds show, at an active ingredient concentration of 10 ppm, an efficacy of 70% or more:

TABLE 3

| Ex_no. | Eff. % |
|---|---|
| 1 | 98 |
| 2 | 100 |
| 3 | 100 |
| 4 | 95 |
| 5 | 84 |
| 6 | 98 |
| 7 | 100 |
| 8 | 100 |
| 9 | 100 |
| 11 | 100 |
| 12 | 100 |
| 13 | 100 |
| 16 | 96 |
| 17 | 92 |
| 18 | 95 |
| 19 | 98 |

TABLE 3-continued

| Ex_no. | Eff. % |
|---|---|
| 25 | 100 |
| 29 | 100 |
| 30 | 100 |
| 34 | 84 |
| 37 | 96 |
| 38 | 100 |
| 39 | 100 |
| 40 | 85 |
| 41 | 78 |
| 42 | 96 |
| 43 | 83 |
| 45 | 96 |
| 46 | 98 |
| 47 | 86 |
| 48 | 95 |
| 49 | 100 |
| 50 | 100 |
| 51 | 100 |
| 52 | 98 |
| 53 | 100 |
| 54 | 91 |
| 55 | 93 |
| 56 | 98 |

The invention claimed is:

1. A compound of the formula (I)

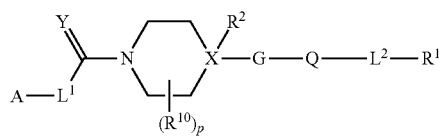
(I)

in which the radicals are each defined as follows:

A is pyrazol-1-yl which may contain up to two substituents, where the substituents are each independently selected from the following list:
   methyl, ethyl, chlorine, bromine, fluorine or trifluoromethyl, $L^1$ is —$CH_2$—, Y is oxygen, X is carbon, $R^2$ is hydrogen, p is 0, G is

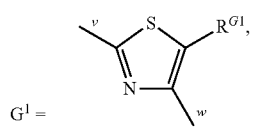

where the bond identified by "v" is bonded directly to X and where the bond identified by "w" is bonded directly to Q, $R^{G1}$ is hydrogen, Q is

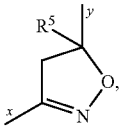

$R^5$ is hydrogen,
   where the bond identified by "x" is bonded directly to G, and the bond identified by "y" is bonded directly to $L^2$, $L^2$ is a direct bond, $R^1$ is phenyl which is substituted once by a $Z^4$ substituent and may additionally optionally have further substitution, where the additional substituents are each independently selected from $Z^4$ and $Z^{1-1}$, $Z^4$ is allyloxy, $Z^{1-1}$ is halogen, $C_1$-$C_6$-alkyl, or $C_1$-$C_6$-haloalkyl, and/or a salt, metal complex and/or an N-oxide thereof.

2. The compound of the formula (I) and/or a salt, metal complex and/or an N-oxide thereof according to claim 1, wherein
   A is 5-methyl-3-(trifluoromethyl)-1H-pyrazol-1-yl, or 3,5-bis(trifluoromethyl)-1H-pyrazol-1-yl.

3. The compound of the formula (I) and/or a salt, metal complex and/or an N-oxide thereof according to claim 1, wherein
   $Z^{1-1}$ is present in the compound and is selected from halogen and $C_1$-$C_6$-alkyl.

4. The compound of the formula (I) and/or a salt, metal complex and/or an N-oxide thereof according to claim 1, wherein
   $R^1$ is 2-(allyloxy)phenyl, 3-(allyloxy)phenyl, 3-(allyloxy)-2,6-difluorophenyl, 2-(allyloxy)-4-methylphenyl, 2-(allyloxy)-4,6-dichlorophenyl, 2-(allyloxy)-6-fluorophenyl, 2-(allyloxy)-6-chlorophenyl, or 2-(allyloxy)-3-fluorophenyl.

5. A compound of the formula (VII)

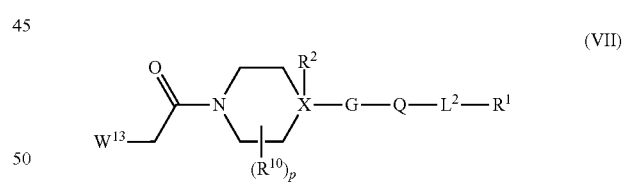
(VII)

and/or a salt, metal complex and/or an N-oxide thereof, in which the radicals are each defined as follows:

X is carbon, $R^2$ is hydrogen, p is 0,

G is

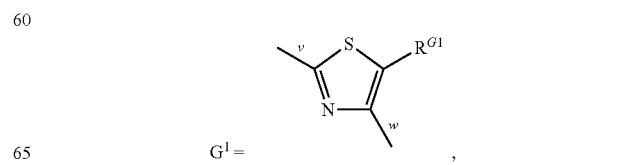

where the bond identified by "v" is bonded directly to X and where the bond identified by "w" is bonded directly to Q, $R^{G1}$ is hydrogen, Q is

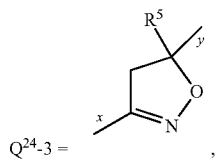

$R^5$ is hydrogen, where the bond identified by "x" is bonded directly to G, and the bond identified by "y" is bonded directly to $L^2$, $L^2$ is a direct bond, $R^1$ is phenyl which is substituted once by a $Z^4$ substituent and may additionally optionally have further substitution, where the additional substituents are each independently selected from $Z^4$ and $Z^{1-1}$, $Z^4$ is allyloxy, $Z^{1-1}$ is halogen, $C_1$-$C_6$-alkyl, or $C_1$-$C_6$-haloalkyl, and $W^{13}$ is a leaving group.

6. A compound of the formula (XVIId)

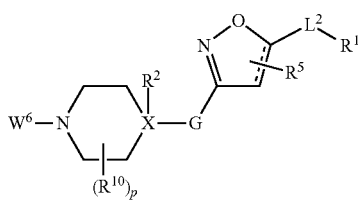

and/or a salt, metal complex and/or an N-oxide thereof, in which the symbol $W^6$ is acetyl, $C_1$-$C_4$ alkoxycarbonyl, benzyl or benzyloxycarbonyl and the remaining radicals are each defined as follows:

X is carbon, $R^2$ is hydrogen, p is 0,

G is

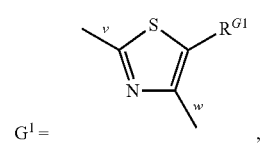

where the bond identified by "v" is bonded directly to X and where the bond identified by "w" is bonded directly to Q, $R^{G1}$ is hydrogen, Q is

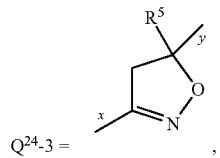

$R^5$ is hydrogen, where the bond identified by "x" is bonded directly to G, and the bond identified by "y" is bonded directly to $L^2$, $L^2$ is a direct bond, $R^1$ is phenyl which is substituted once by a $Z^4$ substituent and may additionally optionally have further substitution, where the additional substituents are each independently selected from $Z^4$ and $Z^{1-1}$, $Z^4$ is allyloxy, $Z^{1-1}$ is halogen, $C_1$-$C_6$-alkyl, or $C_1$-$C_6$-haloalkyl.

7. A compound of the formula (XIIIa)

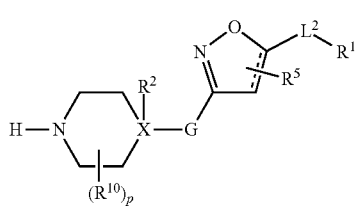

and/or a salt, metal complex and/or an N-oxide thereof, in which the radicals are each defined as follows:

X is carbon, $R^2$ is hydrogen, p is 0,

G is

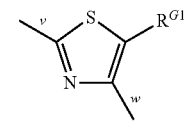

where the bond identified by "v" is bonded directly to X and where the bond identified by "w" is bonded directly to Q, $R^{G1}$ is hydrogen, Q is

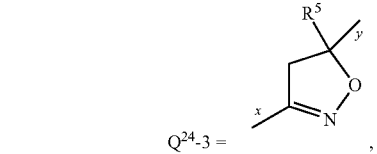

$R^5$ is hydrogen, where the bond identified by "x" is bonded directly to G, and the bond identified by "y" is bonded directly to $L^2$, L² is a direct bond, R¹ is phenyl which is substituted once by a $Z^4$ substituent and may additionally optionally have further substitution, where the additional substituents are each independently selected from $Z^4$ and $Z^{1-1}$, $Z^4$ is allyloxy, $Z^{1-1}$ is halogen, $C_1$-$C_6$-alkyl, or $C_1$-$C_6$-haloalkyl.

8. A composition for controlling phytopathogenic harmful fungi, comprising at least one compound according to claim 1 and one or more extenders and/or surfactants.

9. A method for controlling phytopathogenic harmful fungi, comprising applying a compound according to claim 1 to the phytopathogenic harmful fungi and/or a habitat thereof.

10. The method according to claim 9 comprising treatment of transgenic plants.

11. A process for producing a compositions for controlling phytopathogenic harmful fungi, comprising mixing a compound according to claim 1, with one or more extenders and/or surfactants.

\* \* \* \* \*